(12) United States Patent
Denolf et al.

(10) Patent No.: US 10,900,046 B2
(45) Date of Patent: Jan. 26, 2021

(54) SEED- AND FUNICULUS-PREFERENTIAL PROMOTERS AND USES THEREOF

(71) Applicant: BASF AGRICULTURAL SOLUTIONS SEED US LLC, Research Triangle Park, NC (US)

(72) Inventors: Peter Denolf, Velzeke (BE); Katrien Van Audenhove, Ghent (BE); John Teske, Ghent (BE)

(73) Assignee: BASF AGRICULTURAL SOLUTIONS SEED US LLC, Research Triangle Park, NC (US)

( * ) Notice: Subject to any disclaimer, the term of this patent is extended or adjusted under 35 U.S.C. 154(b) by 84 days.

(21) Appl. No.: 16/093,548

(22) PCT Filed: Apr. 7, 2017

(86) PCT No.: PCT/EP2017/058388
§ 371 (c)(1),
(2) Date: Oct. 12, 2018

(87) PCT Pub. No.: WO2017/178367
PCT Pub. Date: Oct. 19, 2017

(65) Prior Publication Data
US 2019/0127748 A1    May 2, 2019

(30) Foreign Application Priority Data
Apr. 13, 2016 (EP) .................................. 16165100

(51) Int. Cl.
*C12N 15/82* (2006.01)
*C12N 15/113* (2010.01)
(52) U.S. Cl.
CPC ........ *C12N 15/8234* (2013.01); *C12N 15/113* (2013.01); *C12N 15/8279* (2013.01)
(58) Field of Classification Search
None
See application file for complete search history.

(56) References Cited

U.S. PATENT DOCUMENTS

| | | | |
|---|---|---|---|
| 4,757,011 | A | 7/1988 | Chaleff et al. |
| 4,769,061 | A | 9/1988 | Comai |
| 4,940,835 | A | 7/1990 | Shah et al. |
| 4,971,908 | A | 11/1990 | Kishore et al. |
| 5,004,863 | A | 4/1991 | Umbeck |
| 5,593,874 | A | 1/1997 | Brown et al. |
| 5,641,876 | A | 6/1997 | McElroy et al. |
| 5,659,122 | A | 8/1997 | Austin |
| 5,767,363 | A | 6/1998 | De Silva et al. |
| 5,952,489 | A | 9/1999 | Okada et al. |
| 6,342,657 | B1 | 1/2002 | Thomas et al. |
| 6,423,885 | B1 | 7/2002 | Waterhouse et al. |
| 6,483,013 | B1 | 11/2002 | Reynaerts et al. |
| 6,759,570 | B1 | 7/2004 | Prieto-Dapena et al. |
| 7,642,346 | B2 | 1/2010 | Chaudhary et al. |
| 2005/0144667 | A1 | 6/2005 | Stanley et al. |
| 2009/0241230 | A1 | 9/2009 | Duwenig et al. |
| 2010/0154077 | A1* | 6/2010 | Emmanuel ......... C12N 15/8247 800/281 |
| 2010/0281570 | A1 | 11/2010 | Abbitt et al. |

FOREIGN PATENT DOCUMENTS

| | | |
|---|---|---|
| EP | 0242236 A1 | 10/1987 |
| EP | 0242246 A1 | 10/1987 |
| EP | 0507698 A1 | 10/1992 |
| EP | 0508909 A1 | 10/1992 |
| WO | 9012107 A1 | 10/1990 |
| WO | 9953050 A1 | 10/1999 |
| WO | 0071733 A1 | 11/2000 |
| WO | 0112824 A1 | 2/2001 |
| WO | 03052108 A2 | 6/2003 |
| WO | 03076619 A1 | 9/2003 |
| WO | 2004073390 A1 | 9/2004 |
| WO | 2005047505 A2 | 5/2005 |
| WO | 2005049842 A2 | 6/2005 |
| WO | 2005052170 A2 | 6/2005 |
| WO | 2005098004 A2 | 10/2005 |
| WO | 2006074400 A2 | 7/2006 |
| WO | 2008122980 A2 | 10/2008 |
| WO | 2013108017 A1 | 7/2013 |
| WO | 2015022192 A1 | 2/2015 |
| WO | 2015067943 A1 | 5/2015 |

OTHER PUBLICATIONS

Strangeland et al. (J expt. Bot., 54:279-290, 2003).*
Gattolin et al. (J expt. Bot., 57:4225-4233, 2006).*
Barta, et al., "DoOP: Databases of Orthologous Promoters, collections of clusters of orthologous upstream sequences from chordates and plants", Nucleic Acids Research, vol. 33, Issue 1, Jan. 1, 2005, pp. D86-D90.
Delehaunty, et al., "oei86f11.b1 B.oleracea002 *Brassica oleracea* genomic, genomic survey sequence", *Brassica oleracea*, GenBank Accession No. BH988060.1, 2002, 1 page.
International Search Report for PCT Patent Application No. PCT/EP2017/058388, dated Jun. 13, 2017, 5 pages.
Kim, et al., "News and views into the SNARE complexity in *Arabidopsis*", Frontiers in Plant Science, vol. 3, Feb. 10, 2012, 6 pages.
Li, et al., "Control of final seed and organ size by the DA1 gene family in *Arabidopsis thaliana*", Genes and Development, vol. 22, 2008, pp. 1331-1336.

(Continued)

*Primary Examiner* — Vinod Kumar
(74) *Attorney, Agent, or Firm* — Arent Fox LLP

(57) ABSTRACT

The present invention relates to *Brassica* sequences comprising seed- and funiculus-preferential promoter activity. Provided are recombinant genes comprising the seed- and funiculus-preferential promoter operably linked to a heterologous nucleic acid sequence, and cells, plants and seeds comprising the recombinant gene. The promoters can be used to alter gene expression preferentially in the seeds and in the funiculus and to alter biotic or abiotic stress tolerance, yield, seed quality or seed properties.

13 Claims, 9 Drawing Sheets
Specification includes a Sequence Listing.

(56) References Cited

OTHER PUBLICATIONS

Needleman, et al., "A general method applicable to the search for similarities in the amino acid sequence of two proteins", Journal of Molecular Biology, vol. 48, Issue 3, Mar. 1970, pp. 443-453.

Pearson, et al., "Improved tools for biological sequence comparison", Proceedings of the National Academy of Sciences, vol. 85, Issue 8, Apr. 1, 1988, pp. 2444-2448.

Uemura, et al., "Systematic Analysis of SNARE Molecules in *Arabidopsis*: Dissection of the post-Golgi Network in Plant Cells", Cell Structure and Function, vol. 29, Issue 2, 2004, pp. 49-65.

\* cited by examiner

```
SEQ ID NO: 8    1 melppkvkniIlldsegkriaakyysgdwptntakeafekavfsktqktnartevevtalenniivykfv
SEQ ID NO: 9    1 melppkvkniIlldsegkriaakyysgdwptntakeafekavfsktqktnartevevtalenniivykfv
SEQ ID NO: 10   1 melppkvkniIlldsegkriaakyysgdwptntakeafekavfsktqktnartevevtalenniivykfv
SEQ ID NO: 12   1 melppkvkniIlldsegkriaakyysgdwptntakeafekavfsktqktnartevevtalenniivykfv
SEQ ID NO: 11   1 melppkvkniIlldsegkriaakyysgdwptntakeafekavfsktqktnahtevevtalenniivykfv
                  *****************************************************:****************

SEQ ID NO: 8   71 qdlhffvtggeeenelilasvlqglfdavnlllrgnadkrealdnldlificfdeiidggivletdanvi
SEQ ID NO: 9   71 qdlhffvtggeeenelviasvlqglfdavnlllrgnadkrealdnldlificfdeiidggivletdanvi
SEQ ID NO: 10  71 qdlhffvtggeeenelviasil--lfdavnlllrgnadkrealdnldlificfdeiidggivletdanvi
SEQ ID NO: 12  71 qdlhffvtggeeenelviasvlqglfdavnlllrgnvdkrealdnldlificfdeiidggivletdanvi
SEQ ID NO: 11  71 qdlhffvsggeeenelviasvlqglfdavnlllrgnvdkrealdnldlificfdeiidggivletdanvi
                  *******:******:.:****:.****************.******************************

SEQ ID NO: 8  141 aekaginsidpnaplseqtisqalatarehltrslmk
SEQ ID NO: 9  139 aekaginsidpnaplseqtisqalatarehltrslmk
SEQ ID NO: 10 141 aekaginsidpnaplseqtisqalatarehltrslmk
SEQ ID NO: 12 141 aekaginsidpnaplseqtisqalatarehltrslmk
SEQ ID NO: 11 141 aekaginsidpnaplseqtisqalatarehltrslmk
                  *************************************
```

Figure 4

```
SEQ ID NO: 3   1042  gtgctagagtccgtttatgagagactgtgatgtggcatctatccattggtgtgcatcttgcttgcttgctgac
SEQ ID NO: 4    998  tagttagagtccgtttatgagagattgtgatgtgtgcgtctatccgttggtgtggaagaatatttgcttgctgac
SEQ ID NO: 5    993  gtgctagagtccgtttatgagagactgtgatgtgatgtggcatctatccattggtgtggaagaatattgctttgctgac
SEQ ID NO: 6    989  tagttagagtccgtttatgagagattgtgatgtggcgtctatccgttggtggtgaagaatattgcttgctgac
SEQ ID NO: 7    979  gtgttagagtccgtttatgagagattgtgatgtgatgtggcatctatccattgatggaagaagattgctttgctgac SEQ ID NO: 3   1112  aactaacaagatttggtgttatcacaacaaattggagtcggc tatatataa cgctctagagaaggctcaa
SEQ ID NO: 4   1068  aactaacaagatttggtgttatcacaacaaattggagtcggat atatataa cgctctagagaaggcccaa
SEQ ID NO: 5   1063  aactaacaagatttggtgttatcacaacaaattggagtcggc tatatataa cgctctagagaaggctcaa
SEQ ID NO: 6   1059  aactaacaagattcggtgttatcacaacaaattggagtcggat atatataa cgctctagagaaggcccaa
SEQ ID NO: 7   1049  aactaacaagatttggtgttatcacaacaaattggagtcgaat atatataa cgctctagggaaggcccaa
                                            Promoter consensus sequence SEQ ID NO: 3   1182  gtatcagtctaataactggttcaggatccggtttagagagaaaccggagagtgtgacgtgtggaagtagc
SEQ ID NO: 4   1138  gtatcagtctaataactggttcaggatccggtttagagagaaaaccggagagtgtgacgtgtggaagtagc
SEQ ID NO: 5   1133  gtatcagtctaataactggttcaggatccggtttagagagaaaccggagagtgtgacgtgtggaagtagc
SEQ ID NO: 6   1129  gtatcagtctaataactggttcaggatccggtttagagagaaaaccggagagtgtgacgtgtgaaagtagc
SEQ ID NO: 7   1119  gtatcagtctaataactggttcaggatccggtttagagagaaaaccggagagtgtgacgtgtggaagtagc
                                            UTR consensus sequence 1

SEQ ID NO: 3   1252  gctctggattctttgagtcatcatagctcaaagtggacaaaaacaatatttgtaac-----------
SEQ ID NO: 4   1208  actctggattctttgagtcatcatagctcaaagtggacaaaaacaatatttgtaac-----------
SEQ ID NO: 5   1203  actctggattctttgagtcatcatagctcaaagtggacaaaaacaatatttgtaac-----------
SEQ ID NO: 6   1199  actctggattctttgagtcatcatagcttaaagtggacaaaaacaatatttgtaac-----------
SEQ ID NO: 7   1189  actctggattctttgagtcatcatagctcaaagtggacaaaaacaatatttgtaacttcaatattttg
```

Figure 6

```
SEQ ID NO: 3   1310  -----gtatcaaagaatttcctcttcgatatttttacttagagagagagagagagagatctctctttcaa
SEQ ID NO: 4   1266  -----gtatcaaagaatttcctcttcgatatttttacttagagagagagagagagagatctctctttcaa
SEQ ID NO: 5   1261  -----gtatcaaagaatttcctcttcgatatttttacttagagagagagagagagagatctctctttcaa
SEQ ID NO: 6   1257  -----gtatcaaagaatttcctcttcgatatttttactta-----agagagagagagagatctctgtttcaa
SEQ ID NO: 7   1259  taacgtatcaaagaatttcctcttcgatatttttactt------agagagagagagagatctctcttcaa
                     UTR consensus sequence 2

SEQ ID NO: 3   1376  gttctagagctttctccgccgattcatctcctttagcc
SEQ ID NO: 4   1326  gttctagagctttctccgccgattcatctcctttagcc
SEQ ID NO: 5   1327  gttctagagctttctccgccgattcatctcctttagcc
SEQ ID NO: 6   1320  gttctagagctttctccgccgattcatctcctttagcc
SEQ ID NO: 7   1325  gttctagagctttctccgccgattcatctcctttagcc
                     UTR consensus sequence 3
```

Figure 6 (continued)

| | | |
|---|---|---|
| SEQ ID NO: 3 | 1415 | atggtaattaaaaaaaaaaa----ctatttcagtctttcttgccttcatatttcacgtctctctgatt |
| SEQ ID NO: 4 | 1365 | atggtaattaaaaaaaaaaaat----ctgtttcagtctttcttgccttcatatttcacgtttctctggatt |
| SEQ ID NO: 5 | 1366 | atggtaattaaaaaaaaa-------ctatttcagtctttcttgccttcatatttcacgtctctctgatt |
| SEQ ID NO: 6 | 1359 | atggtaattaaaaaaaaaaaaatctatttcagtctttcttgccttcattttcacgtttctctgatt |
| SEQ ID NO: 7 | 1364 | atggtaattaaaaagaaaat-----ctatttcagtctcttcttgccttcatatttcacgtttctctgatt |
| | | Intron consensus sequence 1 |
| SEQ ID NO: 3 | 1481 | ctctgctaattttggattgtggtatggctttacgttgtctaggaaaatcgatggaacaaagaaaact |
| SEQ ID NO: 4 | 1432 | ctctgctaattttggattgtgtggtatggctttacgttgtctaggaaaatcgatggaacaaagaaaact |
| SEQ ID NO: 5 | 1430 | ctctgctaattttggattgtgtggtatggctttacgttgtctaggaaaatcgatggaacaaagaaaact |
| SEQ ID NO: 6 | 1429 | ctctgctaattttggattgtgtggtatggctttacgttgtctaggaaaatcgatggaacaaagaaaact |
| SEQ ID NO: 7 | 1430 | ctctgctaattttggattgtgtggtatggctttacgttgtctaggaaaatcgatggaacaaagaaaaat |
| SEQ ID NO: 3 | 1551 | gaaatgcatgcgatatgttagatttgtaattgtttaaaattaataagaaaattagcagtagtttcaagta |
| SEQ ID NO: 4 | 1502 | gaaatgcatgcgatatgttagatttgtaattgtttatattaaaataatagaaaattagcagtagtttcaagta |
| SEQ ID NO: 5 | 1500 | gaaatgcatgcgatatgttagatttgtaattgtttaaattaatattaaaagaaaattagcagtagtttcaagta |
| SEQ ID NO: 6 | 1499 | gaaatgcatgcgatatgttagatttgtaattgtttatattgttataattaaaagaaaattagcagtagtttcaagta |
| SEQ ID NO: 7 | 1500 | taaatgcatgcgatatgttagatttgtaattgtttatattgttataattaaaagaaaattagcagtagtttcaagta |
| | | Intron consensus sequence 2 |
| SEQ ID NO: 3 | 1621 | agtggttaaaaccaaatagatttatgtaaaacttgcatgtgaaattccaacttaaagtttgttcatgat |
| SEQ ID NO: 4 | 1572 | agtggttaaaaccaaatagatttatgtaaaacttgcatgtgaaattccaacttcaaagtttgttcat--- |
| SEQ ID NO: 5 | 1570 | agtggttaaaaccaaatagatttatgtaaaacttgcatgtgaaattccaacttaaagtttgttcatgat |
| SEQ ID NO: 6 | 1569 | agtggttaaaaccaaatagatttatgtaaaacttgcatgtgaaattccaacttcaaagtttgttcat--- |
| SEQ ID NO: 7 | 1570 | agtggttaaaaccaaatagatttatgtaaaacttgcatgtgaaattccaacttcaaagtttgttcatgat |

Figure 7

SEQ ID NO: 3    1691 gatcttgatagcgtg-aaaatcaagaatttagctttaaaagtcattggaggaggtgctagtgtgagttg
SEQ ID NO: 4    1639 tatcttgatagc----------------------------------------------------------
SEQ ID NO: 5    1640 gatcttgatagcgtg-aaaatcaagaatttagctttaaaagtcattggaggaggtgctagtgtgagttg
SEQ ID NO: 6    1636 tatcttgatagc----------------------------------------------------------
SEQ ID NO: 7    1640 gatcttgatagcgtggaaaatcaagaatttagctttaaaagtcattggaggaggtgctagtgtgagttg
                          Intron consensus 3

Figure 7 (continued)

SEQUENCE LISTING

```
<160> NUMBER OF SEQ ID NOS: 24

<210> SEQ ID NO 1
<211> LENGTH: 6611
<212> TYPE: DNA
<213> ORGANISM: Artificial Sequence
<220> FEATURE:
<223> OTHER INFORMATION: T-DNA PsIp1 BnA::GUS

<400> SEQUENCE: 1
aattacaacg gtatatatcc tgccagtact ttgtggcgct ctatcatagc tataaaccta      60
ttcagcacaa tatcgattaa gggcccctc gagggcgatc gctacgtacc tgcaggcccg     120
ggttaattaa gcggccgctt tggctcgtat atcctctgga aagaatttaa tatctttcgg     180
aatgtaataa tatcttttgg aatgtaaaca aaatggattt aatatctttt ggaatgtaaa     240
agatattatt acattcacac catttttgttt cttttcgcta cgatgaaaga tattaaatcc     300
```

```
aatttggtta ccagtcacac cattttgttt cttttcgcta cgatgaaata attttgaaaa    360
agtaacttct cttattttga ttatgttcgt ttcgatgttc atgtaacctg cgatcgcgac    420
cttaaataaa atattgttct tttgtttgtt gaaagaacaa ttgttttta agttgtttaa     480
attgtcagca aaatgaaatt ttgagtatga ttggtcaacg aagaccaatt ggctgaattt    540
atccatgcat atatatatgt tgagaatcga cgccttcgat tgactttaaa ctcaatcata    600
gaacacactt cgatttagtc cggtacatgt attaaaatcg gtacatcggt taggacctgt    660
cggtccctaa gtttcgatag aagacgttgg aaaacacctt catgaccta aaatacatac     720
gtaatagtaa agccatgttc gtttcgttat cgccgattcc agcggcagcg ttcaaaaata    780
taaggcaaca gagacaaaaa aaaacagaat caaaggtaaa agcaatcgct catcaactgc    840
cagagacact agaaaacgag acgcagtgac gctgaaattt tccgcgtcgt ttagttcatt    900
gttaactgcc gcagcgtctg gaaaacaagt cattaatgcg tcaccggtgc tgtacgatgc    960
catgatgaaa ggcttaatta tctgacgctg acgctgcgtc cagcgttgat aaaacgaaca    1020
ggccttaagt cggtgctgaa gtttaattgc ctctttactt tgtaaccttc ttctttaaat    1080
aggatgttta ccaatcttct agtggattgt acttttcaat gcacttccaa agagtttgaa    1140
attttgtgaa ccagagagtg ttacacaaga acaattgagg tgctagagtc cgttatgaga    1200
ctgtgatgtg gcatctatcc attggtggaa gaagatttgc tttgctgaca actaacaaga    1260
tttggtgtta tcacaacaaa ttggagtcgg ctatatataa cgctctagag aaggctcaag    1320
tatcagtcta ataactggtt caggatccgg tttagagaaa accgggagag tgtgacgtgt    1380
ggaagtagcg ctctggattc tttgagtcat catagctcaa agtggacaaa aaacaatatt    1440
ttgtaacgta tcaaagaatt tcctcttcga tattttact tagagagaga gagagagaga     1500
tcttctcttt caagttctag agctttctcc gccgatttca tctcctttag ccatggtccg    1560
tcctgtagaa accccaaccc gtgaaatcaa aaaactcgac ggcctgtggg cattcagtct    1620
ggatcgcgaa aactgtggaa ttgatcagcg ttggtgggaa agcgcgttac aagaaagccg    1680
ggcaattgct gtgccaggca gttttaacga tcagttcgcc gatgcagata ttcgtaatta    1740
tgcgggcaac gtctggtatc agcgcgaagt ctttataccg aaaggttggg caggccagcg    1800
tatcgtgctg cgtttcgatg cggtcactca ttacggcaaa gtgtgggtca ataatcagga    1860
agtgatggag catcagggcg gctatacgcc atttgaagcc gatgtcacgc cgtatgttat    1920
tgccgggaaa agtgtacgta agtttctgct tctacctttg atatatatat aataattatc    1980
attaattagt agtaatataa tatttcaaat attttttca aaataaaaga atgtagtata     2040
tagcaattgc ttttctgtag tttataagtg tgtatatttt aatttataac ttttctaata    2100
tatgaccaaa atttgttgat gtgcaggtat caccgtttgt gtgaacaacg aactgaactg    2160
gcagactatc ccgccgggaa tggtgattac cgacgaaaac ggcaagaaaa agcagtctta    2220
cttccatgat ttctttaact atgccggaat ccatcgcagc gtaatgctct acaccacgcc    2280
gaacacctgg gtggacgata tcaccgtggt gacgcatgtc gcgcaagact gtaaccacgc    2340
gtctgttgac tggcaggtgg tggccaatgg tgatgtcagc gttgaactgc gtgatgcgga    2400
tcaacaggtg gttgcaactg gacaaggcac tagcgggact ttgcaagtgg tgaatccgca    2460
cctctggcaa ccgggtgaag gttatctcta tgaactgtgc gtcacagcca aagccagac     2520
agagtgtgat atctacccgc ttcgcgtcgg catccggtca gtggcagtga agggcgaaca    2580
gttcctgatt aaccacaaac cgttctactt tactggcttt ggtcgtcatg aagatgcgga    2640
cttgcgtggc aaaggattcg ataacgtgct gatggtgcac gaccacgcat taatggactg    2700
```

```
gattggggcc aactcctacc gtacctcgca ttacccttac gctgaagaga tgctcgactg   2760
ggcagatgaa catggcatcg tggtgattga tgaaactgct gctgtcggct ttaacctctc   2820
tttaggcatt ggtttcgaag cgggcaacaa gccgaaagaa ctgtacagcg aagaggcagt   2880
caacggggaa actcagcaag cgcacttaca ggcgattaaa gagctgatag cgcgtgacaa   2940
aaaccaccca agcgtggtga tgtggagtat tgccaacgaa ccggataccc gtccgcaagg   3000
tgcacgggaa tatttcgcgc cactggcgga agcaacgcgt aaactcgacc cgacgcgtcc   3060
gatcacctgc gtcaatgtaa tgttctgcga cgctcacacc gataccatca gcgatctctt   3120
tgatgtgctg tgcctgaacc gttattacgg atggtatgtc caaagcggcg atttggaaac   3180
ggcagagaag gtactggaaa aagaacttct ggcctggcag agaaactgc atcagccgat   3240 tatcatcacc gaatacggcg tggatacgtt agccgggctg cactcaatgt acaccgacat   3300
gtggagtgaa gagtatcagt gtgcatggct ggatatgtat caccgcgtct tgatcgcgt   3360 cagcgccgtc gtcggtgaac aggtatgaa tttcgccgat tttgcgacct cgcaaggcat   3420
attgcgcgtt ggcggtaaca agaaagggat cttcactcgc gaccgcaaac cgaagtcggc   3480
ggcttttctg ctgcaaaaac gctggactgg catgaacttc ggtgaaaaac cgcagcaggg   3540
aggcaaacaa tgaatcaaca actctcctgg cgcaccatcg tcggctacag cctcggcgcg   3600
tggcgcgcct aagctagcta tatcatcaat ttatgtatta cacataatat cgcactcagt   3660
ctttcatcta cggcaatgta ccagctgata taatcagtta ttgaaatatt tctgaattta   3720
aacttgcatc aataaattta tgttttgct tggactataa tacctgactt gttattttat   3780
caataaatat ttaaactata tttctttcaa gatgaattcg atatcattac cctgttatcc   3840
ctaaagctta ttaatataac ttcgtatagc atacattata cgaagttatg tttcaaattt   3900
attatgtgtt tttttccgt ggtcgagatt gtgtattatt ctttagttat tacaagactt   3960
ttagctaaaa tttgaaagaa tttactttaa gaaaatctta acatctgaga taatttcagc   4020
aatagattat attttcatt actctagcag tattttgca gatcaatcgc aacatatatg   4080
gttgttagaa aaaatgcact atatatata tattatttt tcaattaaa agtgcatgat   4140 atataatata tatatata tatatatgtg tgtgtgtata tggtcaaaga aattcttata   4200
caaatataca cgaacacata tatttgcaa aatcaaagta ttacactaaa caatgagttg   4260
gtgcatggcc aaaacaaata tgtagattaa aaattccagc ctccaaaaaa aaatccaagt   4320
gttgtaaagc attatatata tatagtagat cccaaatttt tgtacaattc cacactgatc   4380 gaattttaa agttgaatat ctgacgtagg attttttta tgtcttacct gaccatttac   4440
taataacatt catacgtttt catttgaaat atcctctata attatattga atttggcaca   4500
taataagaaa cctaattggt gatttatttt actagtaaat ttctggtgat gggctttcta   4560
ctagaaagct ctcggaaaat cttggaccaa atccatattc catgacttcg attgttaacc   4620
ctattagttt tcacaaacat actatcaata tcattgcaac ggaaaaggta caagtaaaac   4680
attcaatccg atagggaagt gatgtaggag gttgggaaga caggcccaga aagagattta   4740
tctgacttgt ttttgtgtata gttttcaatg ttcataaagg aagatggaga cttgagaagt   4800 ttttttttgga ctttgtttag ctttgttggg cgttttttt tttgatcaa aactttgtt   4860 gggcttatga tttgtaatat tttcgtggac tctttagttt atttagacgt gctaactttg   4920
ttgggcttat gacttgttgt aacatattgt aacagatgac ttgatgtgcg actaatcttt   4980
acacattaaa catagttctg ttttttgaaa gttcttattt tcattttat ttgaatgtta   5040
```

```
tatattttc   tatatttata   attctagtaa   aaggcaaatt   ttgcttttaa   atgaaaaaaa    5100
tatatattcc   acagtttcac   ctaatcttat   gcatttagca   gtacaaattc   aaaaatttcc    5160 cattttatt   catgaatcat   accattatat   attaactaaa   tccaaggtaa   aaaaaaggta    5220
tgaaagctct   atagtaagta   aaatataaat   tccccataag   gaaagggcca   agtccaccag    5280
gcaagtaaaa   tgagcaagca   ccactccacc   atcacacaat   ttcactcata   gataacgata    5340
agattcatgg   aattatcttc   cacgtggcat   tattccagcg   gttcaagccg   ataagggtct    5400
caacacctct   ccttaggcct   tgtggccgt   taccaagtaa   aattaacctc   acacatatcc    5460
acactcaaaa   tccaacggtg   tagatcctag   tccacttgaa   tctcatgtat   cctagaccct    5520
ccgatcactc   caaagcttgt   tctcattgtt   gttatcatta   tatatagatg   accaaagcac    5580
tagaccaaac   ctcagtcaca   caaagagtaa   agaagaacaa   tggacccaga   acgacgcccg    5640
gccgacatcc   gccgtgccac   cgaggcggac   atgccggcgg   tctgcaccat   cgtcaaccac    5700
tacatcgaga   caagcacggt   caacttccgt   accgagccgc   aggaaccgca   ggagtggacg    5760
gacgacctcg   tccgtctgcg   ggagcgctat   ccctggctcg   tcgccgaggt   ggacggcgag    5820
gtcgccggca   tcgcctacgc   gggcccctgg   aaggcacgca   acgcctacga   ctggacggcc    5880
gagtcgaccg   tgtacgtctc   cccccgccac   cagcggacgg   gactgggctc   cacgctctac    5940
acccacctgc   tgaagtccct   ggaggcacag   ggcttcaaga   gcgtggtcgc   tgtcatcggg    6000
ctgcccaacg   acccgagcgt   gcgcatgcac   gaggcgctcg   gatatgcccc   ccgcggcatg    6060
ctgcgggcgg   ccggcttcaa   gcacgggaac   tggcatgacg   tgggtttctg   gcagctggac    6120
ttcagcctgc   cggtaccgcc   ccgtccggtc   ctgcccgtca   ccgagatctg   atctcacccg    6180
tctaggatcc   cccgatgagc   taagctagct   atatcatcaa   tttatgtatt   acacataata    6240
tcgcactcag   tctttcatct   acggcaatgt   accagctgat   ataatcagtt   attgaaatat    6300
ttctgaattt   aaacttgcat   caataaattt   atgttttgc   ttggactata   atacctgact    6360
tgttatttta   tcaataaata   tttaaactat   atttctttca   agataaacat   aacttcgtat    6420
agcatacatt   atacgaagtt   atcaaaacgt   cgtgagacag   tttggttaac   tataacggtc    6480
ctaaggtagc   gatcgaggca   ttacggcatt   acggcactcg   cgagggtccg   aatctatgtc    6540
gggtgcggag   aaagaggtaa   tgaaatggca   attcgagcat   ggagccattt   acaattgaat    6600
atatcctgcc   g                                                                6611

<210> SEQ ID NO 2
<211> LENGTH: 7249
<212> TYPE: DNA
<213> ORGANISM: Artificial Sequence
<220> FEATURE:
<223> OTHER INFORMATION: T-DNA Pslp1intron BnA::GUS

<400> SEQUENCE: 2
aattacaacg   gtatatatcc   tgccagtact   ttgtggcgct   ctatcatagc   tataaaccta      60
ttcagcacaa   tatcgattaa   gggcccctc   gagggcgatc   gctacgtacc   tgcaggcccg     120
ggttaattaa   gcggccgctt   tggctcgtat   atcctctgga   agaatttaa   tatctttcgg     180 aatgtaataa   tatcttttgg   aatgtaaaca   aaatggattt   aatatctttt   ggaatgtaaa     240
agatattatt   acattcacac   cattttgttt   cttttcgcta   cgatgaaaga   tattaaatcc     300
aatttggtta   ccagtcacac   cattttgttt   cttttcgcta   cgatgaaata   attttgaaaa     360
agtaacttct   cttattttga   ttatgttcgt   ttcgatgttc   atgtaacctg   cgatcgcgac     420
cttaaataaa   atattgttct   tttgtttgtt   gaaagaacaa   ttgttttta   agttgtttaa     480
```

```
attgtcagca aaatgaaatt ttgagtatga ttggtcaacg aagaccaatt ggctgaattt      540
atccatgcat atatatatgt tgagaatcga cgccttcgat tgactttaaa ctcaatcata      600
gaacacactt cgatttagtc cggtacatgt attaaaatcg gtacatcggt taggacctgt      660
cggtccctaa gtttcgatag aagacgttgg aaaacacctt catgaccota aaatacatac      720 gtaatagtaa agccatgttc gtttcgttat cgccgattcc agcggcagcg ttcaaaaata      780
taaggcaaca gagacaaaaa aaaacagaat caaaggtaaa agcaatcgct catcaactgc      840
cagagacact agaaaacgag acgcagtgac gctgaaattt ccgcgtcgt ttagttcatt       900 gttaactgcc gcagcgtctg gaaaacaagt cattaatgcg tcaccggtgc tgtacgatgc      960
catgatgaaa ggcttaatta tctgacgctg acgctgcgtc cagcgttgat aaaacgaaca     1020
ggccttaagt cggtgctgaa gtttaattgc ctctttactt tgtaaccttc ttctttaaat     1080
aggatgttta ccaatcttct agtggattgt acttttcaat gcacttccaa agagtttgaa     1140
attttgtgaa ccagagagtg ttacacaaga acaattgagg tgctagagtc cgttatgaga     1200
ctgtgatgtg gcatctatcc attggtggaa gaagatttgc tttgctgaca actaacaaga     1260
tttggtgtta tcacaacaaa ttggagtcgg ctatatataa cgctctagag aaggctcaag     1320
tatcagtcta ataactggtt caggatccgg tttagagaaa accgggagag tgtgacgtgt     1380
ggaagtagcg ctctggattc tttgagtcat catagctcaa agtggacaaa aacaatatt      1440 ttgtaacgta tcaaagaatt tcctcttcga tattttact tagagagaga gagagagaga      1500
tcttctcttt caagttctag agctttctcc gccgatttca tctcctttag ccatggtaat     1560
taaaaaaaaa aactattttc agtctttctt gccttcatat ttcacgtctc tctggattct     1620
ctgctaattt tggattgtgg tatggctttt acgttgtcta ggaaaatcga tggaaacaaa     1680
agaaaactga aatgcatgct atatgttaga ttttgtaatt gtttaaaatt aataagaaat     1740
tagcagtagt ttcaagtaag tggttaaaac caaatagatt tatgtaaaac ttgcatgtga     1800
aattccaact ttaaagtttg ttcatgatga tcttgatagc gtgaaaatca agaattttag     1860
ctttaaaagt cattggagga ggtgctagtg tgagttggtt gaatgttgtt aaactgatca     1920
caaagaagaa ttttttgttt tcattgattt tatttttaa gttagtttgt atttgtagta      1980
aggttggaat agcatgtggt gaagatgttg tttagcagtt tgacttccct ggatccatag     2040
gaaaaaggat aattaggcct tctcttaatg taaaaactga gactttgaag ttattctcaa     2100
acgttgttct atcattagat catatatcct tttatgattt gcaatatctc acaatcttta     2160
agctttcttg tgttttattt gttcacatag ggcgtccgtc ctgtagaaac cccaacccgt     2220
gaaatcaaaa aactcgacgg cctgtgggca ttcagtctgg atcgcgaaaa ctgtggaatt     2280
gatcagcgtt ggtgggaaag cgcgttacaa gaaagccggg caattgctgt gccaggcagt     2340
tttaacgatc agttcgccga tgcagatatt cgtaattatg cggcaacgt ctggtatcag      2400 cgcgaagtct ttataccgaa aggttgggca ggccagcgta tcgtgctgcg tttcgatgcg     2460
gtcactcatt acggcaaagt gtgggtcaat aatcaggaag tgatggagca tcagggcggc     2520
tatacgccat ttgaagccga tgtcacgccg tatgttattg ccgggaaaag tgtacgtaag     2580
tttctgcttc tacctttgat atatatataa taattatcat taattagtag taatataata     2640
tttcaaatat ttttttcaaa ataaagaat gtagtatata gcaattgctt ttctgtagtt      2700
tataagtgtg tatattttaa tttataactt ttctaatata tgaccaaaat ttgttgatgt     2760
gcaggtatca ccgtttgtgt gaacaacgaa ctgaactggc agactatccc gccgggaatg     2820
```

```
gtgattaccg acgaaaacgg caagaaaaag cagtcttact tccatgattt ctttaactat    2880
gccggaatcc atcgcagcgt aatgctctac accacgccga acacctgggt ggacgatatc    2940
accgtggtga cgcatgtcgc gcaagactgt aaccacgcgt ctgttgactg gcaggtggtg    3000
gccaatggtg atgtcagcgt tgaactgcgt gatgcggatc aacaggtggt tgcaactgga    3060
caaggcacta gcgggacttt gcaagtggtg aatccgcacc tctggcaacc gggtgaaggt    3120
tatctctatg aactgtgcgt cacagccaaa agccagacag agtgtgatat ctacccgctt    3180
cgcgtcggca tccggtcagt ggcagtgaag gcgaacagt tcctgattaa ccacaaaccg     3240
ttctacttta ctggctttgg tcgtcatgaa gatgcggact gcgtggcaa aggattcgat      3300 aacgtgctga tggtgcacga ccacgcatta atggactgga ttggggccaa ctcctaccgt    3360
acctcgcatt acccttacgc tgaagagatg ctcgactggg cagatgaaca tggcatcgtg    3420
gtgattgatg aaactgctgc tgtcggcttt aacctctctt taggcattgg tttcgaagcg    3480
ggcaacaagc cgaaagaact gtacagcgaa gaggcagtca acgggaaac tcagcaagcg     3540 cacttacagg cgattaaaga gctgatagcg cgtgacaaaa accacccaag cgtggtgatg    3600
tggagtattg ccaacgaacc ggataccgt ccgcaaggtg cacgggaata tttcgcgcca     3660
ctggcggaag caacgcgtaa actcgacccg acgcgtccga tcacctgcgt caatgtaatg    3720
ttctgcgacg ctcacaccga taccatcagc gatctctttg atgtgctgtg cctgaaccgt    3780
tattacggat ggtatgtcca aagcggcgat ttggaaacgg cagagaaggt actgaaaaaa    3840
gaacttctgg cctggcagga gaaactgcat cagccgatta tcatcaccga atacggcgtg    3900
gatacgttag ccgggctgca ctcaatgtac accgacatgt ggagtgaaga gtatcagtgt    3960
gcatggctgg atatgtatca ccgcgtcttt gatcgcgtca gcgccgtcgt cggtgaacag    4020
gtatggaatt tcgccgattt tgcgacctcg caaggcatat tgcgcgttgg cggtaacaag    4080
aaagggatct tcactcgcga ccgcaaaccg aagtcggcgg cttttctgct gcaaaaacgc    4140
tggactggca tgaacttcgg tgaaaaaccg cagcagggag gcaaacaatg aatcaacaac    4200
tctcctggcg caccatcgtc ggctacagcc tcggcgcgtg gcgcgcctaa gctagctata    4260
tcatcaattt atgtattaca cataatatcg cactcagtct ttcatctacg gcaatgtacc    4320
agctgatata atcagttatt gaaatatttc tgaatttaaa cttgcatcaa taaatttatg    4380
tttttgcttg gactataata cctgacttgt tattttatca ataaatattt aaactatatt    4440
tctttcaaga tgaattcgat atcattaccc tgttatccct aaagcttatt aatataactt    4500
cgtatagcat acattatacg aagttatgtt tcaaatttat tatgtgtttt ttttccgtgg    4560
tcgagattgt gtattattct ttagttatta caagactttt agctaaaatt tgaaagaatt    4620
tactttaaga aaatcttaac atctgagata atttcagcaa tagattatat ttttcattac    4680
tctagcagta tttttgcaga tcaatcgcaa catatatggt tgttagaaaa aatgcactat    4740
atatatatat attattttttt caattaaaag tgcatgatat ataatatata tatatatata    4800
tatatgtgtg tgtgtatatg gtcaaagaaa ttcttataca aatatacacg aacacatata    4860
tttgacaaaa tcaaagtatt acactaaaca atgagttggt gcatggccaa acaaatatg     4920 tagattaaaa attccagcct ccaaaaaaaa atccaagtgt tgtaaagcat tatatatata    4980
tagtagatcc caaattttg tacaattcca cactgatcga attttaaag ttgaatatct       5040 gacgtaggat tttttaatg tcttacctga ccatttacta ataacattca tacgttttca     5100
tttgaaatat cctctataat tatattgaat ttggcacata ataagaaacc taattggtga    5160 tttatttac tagtaaattt ctggtgatgg gctttctact agaaagctct cggaaaatct      5220
```

| | | | | | |
|---|---|---|---|---|---|
| tggaccaaat | ccatattcca | tgacttcgat | tgttaaccct | attagttttc | acaaacatac | 5280
| tatcaatatc | attgcaacgg | aaaaggtaca | agtaaaacat | tcaatccgat | agggaagtga | 5340
| tgtaggaggt | tgggaagaca | ggcccagaaa | gagatttatc | tgacttgttt | tgtgtatagt | 5400
| tttcaatgtt | cataaaggaa | gatggagact | tgagaagttt | tttttggact | tgtttagct | 5460
| ttgttgggcg | tttttttttt | ttgatcaata | actttgttgg | gcttatgatt | tgtaatattt | 5520
| tcgtggactc | tttagtttat | ttagacgtgc | taactttgtt | gggcttatga | cttgttgtaa | 5580
| catattgtaa | cagatgactt | gatgtgcgac | taatctttac | acattaaaca | tagttctgtt | 5640
| ttttgaaagt | tcttattttc | atttttattt | gaatgttata | tattttttcta | tatttataat | 5700
| tctagtaaaa | ggcaaatttt | gcttttaaat | gaaaaaaata | tatattccac | agtttcacct | 5760
| aatcttatgc | atttagcagt | acaaattcaa | aaatttccca | tttttattca | tgaatcatac | 5820
| cattatatat | taactaaatc | caaggtaaaa | aaaaggtatg | aaagctctat | agtaagtaaa | 5880
| atataaattc | cccataagga | aagggccaag | tccaccaggc | aagtaaaatg | agcaagcacc | 5940
| actccaccat | cacacaattt | cactcataga | taacgataag | attcatggaa | ttatcttcca | 6000
| cgtggcatta | ttccagcggt | tcaagccgat | aagggtctca | acacctctcc | ttaggccttt | 6060
| gtggccgtta | ccaagtaaaa | ttaacctcac | acatatccac | actcaaaatc | caacggtgta | 6120
| gatcctagtc | cacttgaatc | tcatgtatcc | tagaccctcc | gatcactcca | aagcttgttc | 6180
| tcattgttgt | tatcattata | tatagatgac | caaagcacta | gaccaaacct | cagtcacaca | 6240
| aagagtaaag | aagaacaatg | gacccagaac | gacgcccggc | cgacatccgc | cgtgccaccg | 6300
| aggcggacat | gccggcggtc | tgcaccatcg | tcaaccacta | catcgagaca | agcacggtca | 6360
| acttccgtac | cgagccgcag | gaaccgcagg | agtggacgga | cgacctcgtc | cgtctgcggg | 6420
| agcgctatcc | ctggctcgtc | gccgaggtgg | acggcgaggt | cgccggcatc | gcctacgcgg | 6480
| gccctggaa | ggcacgcaac | gcctacgact | ggacggccga | gtcgaccgtg | tacgtctccc | 6540
| cccgccacca | gcggacggga | ctgggctcca | cgctctacac | ccacctgctg | aagtccctgg | 6600
| aggcacaggg | cttcaagagc | gtggtcgctg | tcatcgggct | gcccaacgac | ccgagcgtgc | 6660
| gcatgcacga | ggcgctcgga | tatgccccc | gcggcatgct | gcgggcggcc | ggcttcaagc | 6720
| acgggaactg | gcatgacgtg | ggtttctggc | agctggactt | cagcctgccg | gtaccgcccc | 6780
| gtccggtcct | gcccgtcacc | gagatctgat | ctcacccgtc | taggatcccc | cgatgagcta | 6840
| agctagctat | atcatcaatt | tatgtattac | acataatatc | gcactcagtc | tttcatctac | 6900
| ggcaatgtac | cagctgatat | aatcagttat | tgaaatattt | ctgaatttaa | acttgcatca | 6960
| ataaatttat | gttttgctt | ggactataat | acctgacttg | ttattttatc | aataaatatt | 7020
| taactatat | ttctttcaag | ataaacataa | cttcgtatag | catacattat | acgaagttat | 7080
| caaaacgtcg | tgagacagtt | tggttaacta | taacggtcct | aaggtagcga | tcgaggcatt | 7140
| acggcattac | ggcactcgcg | agggtccgaa | tctatgtcgg | gtgcggagaa | agaggtaatg | 7200
| aaatggcaat | tcgagcatgg | agccatttac | aattgaatat | atcctgccg | | 7249

<210> SEQ ID NO 3
<211> LENGTH: 2055
<212> TYPE: DNA
<213> ORGANISM: Brassica napus

<400> SEQUENCE: 3

| | | | | | |
|---|---|---|---|---|---|
| tttggctcgt | atatcctctg | gaaagaattt | aatatctttc | ggaatgtaat | aatatctttt | 60

```
ggaatgtaaa caaaatggat ttaatatctt ttggaatgta aaagatatta ttacattcac      120
accattttgt ttcttttcgc tacgatgaaa gatattaaat ccaatttggt taccagtcac      180
accattttgt ttcttttcgc tacgatgaaa taattttgaa aaagtaactt ctcttatttt      240
gattatgttc gtttcgatgt tcatgtaacc tgcgatcgcg accttaaata aaatattgtt      300
cttttgtttg ttgaaagaac aattgttttt taagttgttt aaattgtcag caaaatgaaa      360
ttttgagtat gattggtcaa cgaagaccaa ttggctgaat ttatccatgc atatatatat      420
gttgagaatc gacgccttcg attgacttta aactcaatca tagaacacac ttcgatttag      480
tccggtacat gtattaaaat cggtacatcg gttaggacct gtcggtccct aagtttcgat      540
agaagacgtt ggaaaacacc ttcatgaccc taaaatacat acgtaatagt aaagccatgt      600
tcgtttcgtt atcgccgatt ccagcggcag cgttcaaaaa tataaggcaa cagagacaaa      660
aaaaaacaga atcaaaggta aaagcaatcg ctcatcaact gccagagaca ctagaaaacg      720
agacgcagtg acgctgaaat tttccgcgtc gtttagttca ttgttaactg ccgcagcgtc      780
tggaaaacaa gtcattaatg cgtcaccggt gctgtacgat gccatgatga aaggcttaat      840
tatctgacgc tgacgctgcg tccagcgttg ataaaacgaa caggccttaa gtcggtgctg      900
aagtttaatt gcctctttac tttgtaacct tcttctttaa ataggatgtt taccaatctt      960
ctagtggatt gtacttttca atgcacttcc aaagagtttg aaattttgtg aaccagagag     1020
tgttacacaa gaacaattga ggtgctagag tccgttatga gactgtgatg tggcatctat     1080
ccattggtgg aagaagattt gctttgctga caactaacaa gatttggtgt tatcacaaca     1140
aattggagtc ggctatatat aacgctctag agaaggctca agtatcagtc taataactgg     1200
ttcaggatcc ggtttagaga aaaccgggag agtgtgacgt gtggaagtag cgctctggat     1260
tctttgagtc atcatagctc aaagtggaca aaaaacaata ttttgtaacg tatcaaagaa     1320
tttcctcttc gatatttta cttagagaga gagagagaga gatcttctct ttcaagttct     1380
agagctttct ccgccgattt catctccttt agccatggta attaaaaaaa aaaactattt     1440
tcagtctttc ttgccttcat atttcacgtc tctctggatt ctctgctaat tttggattgt     1500
ggtatggctt ttacgttgtc taggaaaatc gatggaaaca aaagaaaact gaaatgcatg     1560
ctatatgtta gattttgtaa ttgtttaaaa ttaataagaa attagcagta gtttcaagta     1620
agtggttaaa accaaataga tttatgtaaa acttgcatgt gaaattccaa ctttaaagtt     1680
tgttcatgat gatcttgata gcgtgaaaat caagaatttt agctttaaaa gtcattggag     1740
gaggtgctag tgtgagttgg ttgaatgttg ttaaactgat cacaaagaag aattttttgt     1800
tttcattgat tttattttt aagttagttt gtatttgtag taaggttgga atagcatgtg     1860
gtgaagatgt tgtttagcag tttgacttcc ctggatccat aggaaaaagg ataattaggc     1920
cttctcttaa tgtaaaaact gagactttga agttattctc aaacgttgtt ctatcattag     1980
atcatatatc cttttatgat ttgcaatatc tcacaatctt taagctttct tgtgttttat     2040
ttgttcacat agggc                                                      2055
```

<210> SEQ ID NO 4
<211> LENGTH: 1650
<212> TYPE: DNA
<213> ORGANISM: Brassica napus

<400> SEQUENCE: 4

```
aacattttt ctgtcaaaac caaaaaaatg attttttcg ctaaaccgt aaaaaaaaa         60
attatctcac agaaaccaaa atatgcgttt ttccgccgaa acggaaaaac cgagttttct    120
```

```
cgccaaaaca ataaaaccaa gttttcccgt caaaaccgca aaaccgagtg ttctcgccaa      180
aaccgcaaaa ccaaaatttc ctgccaaaac cccaaaaccg cgaaaccgag tttttccgac      240
aaaaccttaa aattgagttt tccgactgaa aaccgcaaaa tcgagttttc ccgccaaaac      300
cgcaaaaccg agttttctca ccaaaaccgt aaaacaagtt ttttccgcca aaaccgcaaa      360
acccaattttt tccgccaaaa ccgcaaaacg agttttccag ccgaaaccaa aaaaccgagt      420
ttcccgccaa aactgaaaaa ccaagttttc cgccaaaaac cgcaaaaccg agttttctcg      480
ccaaaaccgc aaagcaaatt ttgttcgcca aaaccgcaaa accgaatttt cccgccaaaa      540
ccacaaagag tttcttcgcc gaaaccagaa accgagtttt tccgccaaaa atcgcaaaac      600
cgagttttttc cgtcaaaatc agaaaaatga gttttcccgc caaaaccgta aaatcgagtt      660
ttcctgccga aaccgcaaaa ccgagttttt ccgccaaaat cgaaaacaga atttcccgcc      720
aaaatcgtaa acgagttttt gcgctaaaac atgttttttct ataaaattgc gaaatcttgt      780
ttatatatta aagctcacat taatgatatt aatatttttac atgatctttt tagaataaat      840
aagataatat ttttggtatc tatgggtaaa catataccgt atttgggttt ggatttcaac      900
cttgatgttt ctgggttttt gcaggtcggg tataaactgg gttaggttgt ctgttggttg      960
gatttgggtg ggttattata ccctacgtta acatccctag ttagagtccg ttatgagatt     1020
gtgatgtggc gtctatccgt tggtggaaga atatttgctt tgctgacaac taacaagatt     1080
tggtgttatc acaacaaatt ggagtcggat atatataacg ctctagagaa ggcccaagta     1140
tcagtctaat aactggttca ggatccggtt tagagaaaac cgggagagtg tgacgtgtgg     1200
aagtagcact ctggattctt tgagtcatca tagctcaaag tggacaaaaa acaatatttt     1260
gtaacgtatc aaagaatttc ctcttcgata tttttactta gagagagaga gatcttctct     1320
ttcaagttct agagctttct ccgccgattt catctccttt agccatggta attaaaaaaa     1380
aaaatctgtt ttcagtcttt cttgccttca tatttcacgt ttctctggat tctctgctaa     1440
ttttggattg tggtatggct tttacgttgt ctaggaaaat cgatggaaac aaaagaaaac     1500
tgaaatgcat gcgatatgtt agattttgta attgtttata attaaaaaaa aattagcagt     1560
agtttcaagt aagtggttaa aaccaaatag atttatgtaa aacttgcatg tgaaattcca     1620
acttcaaagt tgttcattta tcttgatagc                                      1650
```

<210> SEQ ID NO 5
<211> LENGTH: 2001
<212> TYPE: DNA
<213> ORGANISM: Brassica rapa

<400> SEQUENCE: 5

```
tgaattttct gaatgactag gatgtactag attttttggc tcgtatatct tcgggaaaga       60
atttaatatc tttcggaatg taataatatc ttttggaatg taaacaaaag ggatttaata      120
tcttttggaa tgtaaaagat attattacat tcacaccatt ttgtttcttt tcgctacgat      180
gaaagatatt aaatccaatt tggttaccag tcacaccatt ttgtttcttt tcgctacgat      240
gaataatttt tgaaaagta acttctctta ttttgattat gttcgtttcg atgttcatgt      300
aacctgcgat cgcgacctta aataaaatat tgttcttttg tttgtttaaa gaacaattgt      360
ttttatgttg tttaaattgt cagcaaaatg aaatattgag tatgattggt caacgaagac      420
caattggctg aatttaacca tgcatatata tatatatata tatatattat atatgttgag      480
aatcgacgcc ttcgattgac tttaaactca atcatagaac acacttcgat ttagtccggt      540
```

| | |
|---|---|
| acatgtatta aaatcggtac atcggttagg acctgtcggt ccctaagttt cgatagaaga | 600 |
| cgttggaaaa cacctcttaa gaagaagaag aagaagaaga agaagaattc acaaagaaga | 660 |
| agaagaattc acaaagaaga gaagagaaca tcaagtcaaa gtcatgactc taaaatacat | 720 |
| acgtaatagt atcaagtcat cacgtcagaa tagattctct ctcagattaa tactcttctg | 780 |
| gttttgttga cgacgaggga aacgaagtct aagtcggtgc tgaagtttca ttgccttctg | 840 |
| tgacacatga atatcactaa aacctcttta ctttgtaacc ttcttcttta tataggatgt | 900 |
| ttaccaatct tctagtggat tgtactttc aatgcacttc caaagagttt gaaattttgt | 960 |
| gaaccagaga gtgttacaca agaaaaattg aggtgctaga gtccgttatg agactgtgat | 1020 |
| gtggcatcta tccattggtg gaagaagatt tgctttgctg acaactaaca agatttggtg | 1080 |
| ttatcacaac aaattggagt cggctatata aacgctcta gagaaggctc aagtatcagt | 1140 |
| ctaataactg gttcaggatc cggtttagag aaaaccggga gagtgtgacg tgtggaagta | 1200 |
| gcactctgga ttctttgagt catcatagct caaagtggac aaaaaacaat attttgtaac | 1260 |
| gtatcaagaa atttcctctt cgatattttt acttagagag agagagagag agatcttctc | 1320 |
| tttcaagttc tagagctttc tccgccgatt tcatctcctt tagccatggt aattaaaaaa | 1380 |
| aaactatttt cagtctttct tgccttcata tttcacgtct ctctggattc tctgctaatt | 1440 |
| ttggattgtg gtatggcttt tacgttctct aggaaaatcg atggaaacaa agaaaactg | 1500 |
| aaatgcatgc tatatgttag attttgtaat tgtttaaaat taataagaaa ttagcagtag | 1560 |
| tttcaagtaa gtggttaaaa ccaaatagat ttatgtaaaa cttgcatgtg aaattccaac | 1620 |
| tttaaagttt gttcatgatg atcttgatag cgtgaaaatc aagaattta gctttaaaag | 1680 |
| tcattggagg aggtgctagt gtgagttggt tgaatgttgt taaactgatc acaaagaaga | 1740 |
| attttttgtt ttcattgatt ttattttta agttagtttg tatttgtagt aaggttggaa | 1800 |
| tagcatgtgg tgaagatgtt gtttagcagt ttgacttccc tggatccata ggaaaaagga | 1860 |
| taattaggcc ttctcttaat gtaaaaactg agactttgaa gttattctca aacgttgttc | 1920 |
| tatcattaga tcatatatcc ttttatgatt tgcaatatct cacaatcttt aagctttctt | 1980 |
| gtgttttatt tgttcacata g | 2001 |

<210> SEQ ID NO 6
<211> LENGTH: 1647
<212> TYPE: DNA
<213> ORGANISM: Brassica oleracea

<400> SEQUENCE: 6

| | |
|---|---|
| aaaaatgatt ttttcgcta aaccgtaaa aaaataaatt atctcacaga aaccaaaata | 60 |
| tgagttttcc cgccgaaacc gaaaaccgg gttttctgc caaaccata aaccaagtt | 120 |
| ttcccgtcaa aaccgcaaaa ccgagtgttc tcgccaaaac cgcaaaacca aaatttcccg | 180 |
| ccaaaacccc aaaaccgcga aaccgagttt tccgacaaa accttaaaat tgagtttttc | 240 |
| cgactgaaaa ccgcaaaacc gagtttttcc gccaaaagcg cgaaaccgag tttctcacc | 300 |
| aaaccgtta aataagttt tccgccaaaa ccgcaaaacc cattttttc gccaaaaccg | 360 |
| caaaacgagt tttcctgccg aaaccgaaaa atcgagtttt cccgccaaaa ccgaaaaatc | 420 |
| gagttttccc gccaaaaccg caaaaccgag tttctagcc aaaaccgcaa agcaaatttt | 480 |
| gttcgccaaa accgcaaaac cgaatttcc cgccaaaacc acaagagtt cttcgccga | 540 |
| aaccagaaaa ccgagttttc ccgccaaaat cgcaaaaccg agtttttccg tcgaaaccac | 600 |
| aaaaggagt tttcccgcca aaaccgtaaa atcgagtttt tctgccgaaa ccgcaaaacc | 660 |

```
gagttttccc gccaaaatcg aaaacggaat ttcccgccaa aatcgtaaac gagttttttgc     720 gctaaaacaa gttttctat aaaattacga atcttgttt atatattaaa gctcacatta       780
atgatattaa tattttacat gatatttta gaataaataa gataatattt tgggtatcga      840
tgggtaaacc tataccgtat ttgggttatt ttttgggttt ggatttcaac cttgatgttt     900
ctgggttttt gcatggttgg gtataaactg ggttaggtta tatgttggtt gggctggggt    960
gggttatttt accctacgtt aacatcccta gttagagtcc gttatgagat tgtgatgtgg    1020
cgtctatccg ttggtggaag aatatttgct ttgctgacaa ctaacaagat tcggtgttat   1080
cacaacaaat tggagtcgga tatatataac gctctagaga aggcccaagt atcagtctaa   1140
taactggttc aggatccggt ttagagaaaa ccgagagagt gtgacgtgtg aaagtagcac   1200
tctggattct ttgagtcatc atagcttaaa gtggacaaaa aacaatattt tgtaacgtat   1260
caaagaattt cctcttcgat attttttactt aagagagaga gagagatctt ctgtttcaag   1320
ttctagagct ttctccgccg atttcatctc ctttagccat ggtaattaaa aaaaaaaaaa   1380
atctattttc agtctttctt gccttcattt ttcacgtttc tctggattct ctgctaattt    1440
tggattgtgg tatggctttt acgttgtcta ggaaaatcga tggaaacaaa agaaaactga   1500
aatgcatgcg atatgttaga ttttgtaatt gtttataatt aaaagaaat tagcagtagt    1560 ttcaagtaag tggttaaaac caaatagatt tatgtaaaac ttgcatgtga aattccaact   1620
tcaaagtttg ttcattatct tgatagc                                        1647

<210> SEQ ID NO 7
<211> LENGTH: 2001
<212> TYPE: DNA
<213> ORGANISM: Brassica juncea

<400> SEQUENCE: 7
aatgtggaca tgttctgttt tataaaaaaa gaaacaaaat gaattttctg aatgactacg     60
atttactaga tttttttggct cgtatatctt ctggaaagaa tttaatatct ttcggaatgt   120
aataatatct tttggaatgt aaacaaaagg gatttaatat cttttggaat gtaaaagata    180
ttattattca caccattttg tttcttttcg ctacgatgaa agatattaaa tccaatttgg    240
ttaccagtca caccattttg tttcttttcg ctacgatgaa ataattttga aaaagtaact    300
tctcttattt tgattatgtt cgtttcgatg ttcatgtaac ctgcgatcgc gaccttaaat    360
aaaatattgt tcttttgttt gtttaaagaa caattgtttt taaattgtt taaattgtca    420 gcaaaatgaa attttgagta tgattggtca acgaagacca attggctgaa tttatccatg    480
catatatata tgttgagaat cgacgccttc gattgacttt aaactcaatc atagaacaca    540
cttcgattta gtccggtaca tgtattaaaa tcggtacatc ggttaggacc cctaagtttc    600
gatagaagac gttggaaaac acctcttaag aagaagaaga agaagaattc acaaagaaga    660
gaagagaaca ccaagtcaaa gtcatgactc taaaatacat acgtaatagt atcaagtcat    720
cacgtcagaa tagattctct ctcagattaa tactcttctg gttttgttga cgacgaggga    780
aacgaagtct aagtcggtgc tgaagtttca ttgccttctt ctcatgtgac acatgaatat    840
cactaaaacg tctttacttt gtaaccttct tcttaaata ggatgtttac caatcttcta   900
gtggattgta cttttcaatg cacttccaaa gagtttgaaa ttttgtgagc cagagagtgt    960
tacacaagaa aaattgaggt gttagagtcc gttatgagat tgtgatgtgg catctatcca   1020
ttgatggaag aagatttgct ttgctgacaa ctaacaagat ttggtgttat cacaacaaat   1080
```

-continued

```
tggagtcgaa tatatataac gctctaggga aggcccaagt atcagtctaa taactggttc    1140
aggatccggt ttagagaaaa ccgggagagt gtgacgtgtg gaagtagcac tctggattct    1200
ttgagtcatc atagctcaaa gtggacaaaa acaatatttt tgtaacttca atattttgta    1260
acgtatcaaa gaatttcctc ttcgatattt ttacttagag agagagagag atcttctctt    1320
tcaagttcta gagctttctc cgccgatttc atctccttta gccatggtaa ttaaaaagaa    1380
aatctatttt cagtctttct tgccttcata tttcacgttt ctctggattc tctgctaatt    1440
ttggattgtg gtatggcttt tacgttgtct aggaaaatcg atggaaacaa agaaaaatt    1500 aaatgcatgc gatatgttag attttgtaat tgtttataat taaaaagaaa ttagcagtag    1560
tttcaagtaa gtggttaaaa ccaaatagat ttatgtaaaa cttgcatgtg aaattccaac    1620
ttcaaagttt gttcatgatg atcttgatag cgtggaaaat caagaatttt agctttaaaa    1680
gtcattggag gaggtgctag tgtgagttgg ttgaatgttg ttaaactgat cacaaagaag    1740 aattttttgtt ttcattgatt ttattttgta agttagtttg tatttgtagt aaggttggaa    1800
tagcatgtgg tgaagatgtt gtttagcagt ttaacttccc tggatccata ggaaaaagga    1860
taattaggcc ttctcttaat gtaaaaactg agactttgaa gttattctca acgttgttc    1920 tatcattgga tcatatatcc ttttatgata tgcaatatct cacaatcttt aagctttctt    1980
gtgttttatt tgttcacata g                                             2001
```

<210> SEQ ID NO 8
<211> LENGTH: 177
<212> TYPE: PRT
<213> ORGANISM: Brassica napus

<400> SEQUENCE: 8

```
Met Glu Leu Pro Pro Lys Val Lys Asn Ile Leu Leu Asp Ser Glu
1               5                   10                  15

Gly Lys Arg Ile Ala Ala Lys Tyr Tyr Ser Gly Asp Trp Pro Thr Asn
            20                  25                  30

Thr Ala Lys Glu Ala Phe Glu Lys Ala Val Phe Ser Lys Thr Gln Lys
        35                  40                  45

Thr Asn Ala Arg Thr Glu Val Glu Val Thr Ala Leu Glu Asn Asn Ile
    50                  55                  60

Ile Val Tyr Lys Phe Val Gln Asp Leu His Phe Phe Val Thr Gly Gly
65                  70                  75                  80

Glu Glu Glu Asn Glu Leu Ile Leu Ala Ser Val Leu Gln Gly Leu Phe
                85                  90                  95

Asp Ala Val Asn Leu Leu Arg Gly Asn Ala Asp Lys Arg Glu Ala
            100                 105                 110

Leu Asp Asn Leu Asp Leu Ile Phe Leu Cys Phe Asp Glu Ile Ile Asp
        115                 120                 125

Gly Gly Ile Val Leu Glu Thr Asp Ala Asn Val Ile Ala Glu Lys Ala
    130                 135                 140

Gly Ile Asn Ser Ile Asp Pro Asn Ala Pro Leu Ser Glu Gln Thr Ile
145                 150                 155                 160

Ser Gln Ala Leu Ala Thr Ala Arg Glu His Leu Thr Arg Ser Leu Met
                165                 170                 175

Lys
```

<210> SEQ ID NO 9
<211> LENGTH: 175
<212> TYPE: PRT

<213> ORGANISM: Brassica napus

<400> SEQUENCE: 9

Met Glu Leu Pro Pro Lys Val Lys Asn Ile Leu Leu Leu Asp Ser Glu
1               5                   10                  15

Gly Lys Arg Ile Ala Ala Lys Tyr Tyr Ser Gly Asp Trp Pro Thr Asn
            20                  25                  30

Thr Ala Lys Glu Ala Phe Glu Lys Ala Val Phe Ser Lys Thr Gln Lys
        35                  40                  45

Thr Asn Ala Arg Thr Glu Val Glu Val Thr Ala Leu Glu Asn Asn Ile
    50                  55                  60

Ile Val Tyr Lys Phe Val Gln Asp Leu His Phe Phe Val Thr Gly Gly
65                  70                  75                  80

Glu Glu Glu Asn Glu Leu Val Leu Ala Ser Leu Leu Leu Phe Asp Ala
                85                  90                  95

Val Asn Leu Leu Leu Arg Gly Asn Ala Asp Lys Arg Glu Ala Leu Asp
            100                 105                 110

Asn Leu Asp Leu Ile Phe Leu Cys Phe Asp Glu Ile Ile Asp Gly Gly
        115                 120                 125

Ile Val Leu Glu Thr Asp Ala Asn Val Ile Ala Glu Lys Ala Gly Ile
    130                 135                 140

Asn Ser Ile Asp Pro Asn Ala Pro Leu Ser Glu Gln Thr Ile Ser Gln
145                 150                 155                 160

Ala Leu Ala Thr Ala Arg Glu His Leu Thr Arg Ser Leu Met Lys
                165                 170                 175

<210> SEQ ID NO 10
<211> LENGTH: 177
<212> TYPE: PRT
<213> ORGANISM: Brassica rapa

<400> SEQUENCE: 10

Met Glu Leu Pro Pro Lys Val Lys Asn Ile Leu Leu Leu Asp Ser Glu
1               5                   10                  15

Gly Lys Arg Ile Ala Ala Lys Tyr Tyr Ser Gly Asp Trp Pro Thr Asn
            20                  25                  30

Thr Ala Lys Glu Ala Phe Glu Lys Ala Val Phe Ser Lys Thr Gln Lys
        35                  40                  45

Thr Asn Ala Arg Thr Glu Val Glu Val Thr Ala Leu Glu Asn Asn Ile
    50                  55                  60

Ile Val Tyr Lys Phe Val Gln Asp Leu His Phe Phe Val Thr Gly Gly
65                  70                  75                  80

Glu Glu Glu Asn Glu Leu Val Leu Ala Ser Val Leu Gln Gly Leu Phe
                85                  90                  95

Asp Ala Val Asn Leu Leu Leu Arg Gly Asn Val Asp Lys Arg Glu Ala
            100                 105                 110

Leu Asp Asn Leu Asp Leu Ile Phe Leu Cys Phe Asp Glu Ile Ile Asp
        115                 120                 125

Gly Gly Ile Val Leu Glu Thr Asp Ala Asn Val Ile Ala Glu Lys Ala
    130                 135                 140

Gly Ile Asn Ser Ile Asp Pro Asn Ala Pro Leu Ser Glu Gln Thr Ile
145                 150                 155                 160

Ser Gln Ala Leu Ala Thr Ala Arg Glu His Leu Thr Arg Ser Leu Met
                165                 170                 175

Lys

<210> SEQ ID NO 11
<211> LENGTH: 177
<212> TYPE: PRT
<213> ORGANISM: Brassica oleracea

<400> SEQUENCE: 11

Met Glu Leu Pro Pro Lys Val Lys Asn Ile Leu Leu Asp Ser Glu
1               5                   10                  15

Gly Lys Arg Ile Ala Ala Lys Tyr Tyr Ser Gly Asp Trp Pro Thr Asn
                20                  25                  30

Thr Ala Lys Glu Ala Phe Glu Lys Ala Val Phe Ser Lys Thr Gln Lys
            35                  40                  45

Thr Asn Ala His Thr Glu Val Glu Val Thr Ala Leu Glu Asn Asn Ile
    50                  55                  60

Ile Val Tyr Lys Phe Val Gln Asp Leu His Phe Phe Val Ser Gly Gly
65                  70                  75                  80

Glu Glu Glu Asn Glu Leu Val Leu Ala Ser Val Leu Gln Gly Leu Phe
                85                  90                  95

Asp Ala Val Asn Leu Leu Leu Arg Gly Asn Ala Asp Lys Arg Glu Ala
            100                 105                 110

Leu Asp Asn Leu Asp Leu Ile Phe Leu Cys Phe Asp Glu Ile Ile Asp
        115                 120                 125

Gly Gly Ile Val Leu Glu Thr Asp Ala Asn Val Ile Ala Glu Lys Ala
    130                 135                 140

Gly Ile Asn Ser Ile Asp Pro Asn Ala Pro Leu Ser Glu Gln Thr Ile
145                 150                 155                 160

Ser Gln Ala Leu Ala Thr Ala Arg Glu His Leu Thr Arg Ser Leu Met
                165                 170                 175

Lys

<210> SEQ ID NO 12
<211> LENGTH: 177
<212> TYPE: PRT
<213> ORGANISM: Brassica juncea

<400> SEQUENCE: 12

Met Glu Leu Pro Pro Lys Val Lys Asn Ile Leu Leu Asp Ser Glu
1               5                   10                  15

Gly Lys Arg Ile Ala Ala Lys Tyr Tyr Ser Gly Asp Trp Pro Thr Asn
                20                  25                  30

Thr Ala Lys Glu Ala Phe Glu Lys Ala Val Phe Ser Lys Thr Gln Lys
            35                  40                  45

Thr Asn Ala Arg Thr Glu Val Glu Val Thr Ala Leu Glu Asn Asn Ile
    50                  55                  60

Ile Val Tyr Lys Phe Val Gln Asp Leu His Phe Phe Val Thr Gly Gly
65                  70                  75                  80

Glu Glu Glu Asn Glu Leu Val Leu Ala Ser Val Leu Gln Gly Leu Phe
                85                  90                  95

Asp Ala Val Asn Leu Leu Leu Arg Gly Asn Val Asp Lys Arg Glu Ala
            100                 105                 110

Leu Asp Asn Leu Asp Leu Ile Phe Leu Cys Phe Asp Glu Ile Ile Asp
        115                 120                 125

Gly Gly Ile Val Leu Glu Thr Asp Ala Asn Val Ile Ala Glu Lys Ala
    130                 135                 140

Gly Ile Asn Ser Ile Asp Pro Asn Ala Pro Leu Ser Glu Gln Thr Ile
145                 150                 155                 160

Ser Gln Ala Leu Ala Thr Ala Arg Glu His Leu Thr Arg Ser Leu Met
                165                 170                 175

Lys

<210> SEQ ID NO 13
<211> LENGTH: 534
<212> TYPE: DNA
<213> ORGANISM: Brassica napus

<400> SEQUENCE: 13
atggagttac ccccaaaagt gaagaacatt ctgcttcttg attctgaagg aaagcgcata      60
gccgctaagt actactctgg cgactggcca acaaatacgg ctaaagaagc attcgaaaaa     120
gctgtcttct caaagactca aaaacaaac gctcgcaccg aagttgaagt gacggcactg      180
gagaacaaca tcattgtgta caaatttgtg caagatcttc atttctttgt tacgggaggt     240
gaagaagaaa acgagcttat cttagccagt gtgcttcagg gtctcttcga tgcagtgaat     300
ctcctcctca gaggcaatgc tgataagaga gaggcattgg acaatcttga tctcatctttt   360
ctatgctttg acgaaatcat cgatggcggt attgtcctgg acgcgatgc aaatgtgata     420
gcagaaaagg caggaatcaa tagcattgac cctaacgctc ctctatccga gcagacgata     480
agtcaggcac tggcgacggc aagagagcat ttgacaaggt cacttatgaa atga           534

<210> SEQ ID NO 14
<211> LENGTH: 528
<212> TYPE: DNA
<213> ORGANISM: Brassica napus

<400> SEQUENCE: 14
atggagttac ccccaaaagt gaagaacatt ctgcttcttg attctgaagg aaagcgcata      60
gccgctaagt actactctgg cgactggcca acaaatacgg ctaaagaagc attcgaaaaa     120
gctgtcttct caaagactca gaaaacaaac gctcgcaccg aagttgaagt gacggcactg     180
gagaacaaca tcattgtgta caaatttgtg caagatcttc atttctttgt tacgggaggt     240
gaagaagaaa acgagcttgt cttagccagt ttgcttctct tcgatgcagt gaatctcctc     300
ctcagaggca atgctgataa agagagaggca ttggacaatc ttgatctcat ctttctatgc    360
tttgacgaaa tcatcgatgg cggtattgtc ctggagacgg atgcaaatgt gatagcagaa    420
aaggcaggaa tcaatagcat tgaccctaac gctcctctat ccgagcagac gataagtcag    480
gcactggcaa cggcaagaga gcatttgaca aggtcactta tgaaatga                  528

<210> SEQ ID NO 15
<211> LENGTH: 534
<212> TYPE: DNA
<213> ORGANISM: Brassica rapa

<400> SEQUENCE: 15
atggagttac ccccaaaagt gaagaacatt ctgcttcttg attctgaagg aaagcgcata      60
gccgctaagt actactctgg cgactggcca acaaatacgg ctaaagaagc attcgaaaaa     120
gctgtcttct caaagactca aaaacaaac gctcgcaccg aagttgaagt gacggcactg      180
gagaacaaca tcattgtgta caaatttgtg caagatcttc atttctttgt tacgggaggt     240
gaagaagaaa acgagcttgt cttagccagt gtgcttcagg gtctcttcga tgcagtgaat    300
ctcctcctca gaggcaatgt tgataagaga gaggcattgg acaatcttga tctcatctttt   360

```
ctatgctttg acgaaatcat cgatggcggt attgtcctgg agacggatgc aaatgtgata       420
gcagaaaagg caggaatcaa tagcattgac cctaacgctc ctctatccga gcagacgata       480
agtcaggcac tggcgacggc aagagagcat ttgacaaggt cacttatgaa atga            534
```

<210> SEQ ID NO 16
<211> LENGTH: 534
<212> TYPE: DNA
<213> ORGANISM: Brassica oleracea

<400> SEQUENCE: 16

```
atggagttac ccccaaaagt gaagaacatt ctgcttcttg attctgaagg aaagcgcata       60
gccgctaagt actactctgg cgactggcca acaaatacgg ctaaagaagc attcgaaaaa      120
gctgtcttct caaagactca gaaaacaaac gctcacaccg aagttgaagt gacggcactg      180
gagaacaaca tcattgtgta caaatttgtg caagatcttc atttctttgt tcgggaggt       240 gaagaagaaa acgagcttgt cttagccagt gtgcttcagg gtctcttcga tgcagtgaat      300
ctcctcctca gaggcaatgc tgataagaga gaggcattgg acaatcttga tctcatcttt      360
ctatgctttg acgaaatcat tgatggcggt attgtcctgg agacggatgc aaatgtgata      420
gcagaaaagg caggaatcaa tagcattgac cctaacgctc ctctatccga gcagacgata      480
agtcaggcac tggcaacggc aagagagcat ttgacaaggt cacttatgaa atga            534
```

<210> SEQ ID NO 17
<211> LENGTH: 534
<212> TYPE: DNA
<213> ORGANISM: Brassica juncea

<400> SEQUENCE: 17

```
atggagttac ccccaaaagt gaagaacatt ctgcttcttg attctgaagg aaagcgcata       60
gccgctaagt actactctgg cgactggcca acaaatacgg ctaaagaagc attcgaaaaa      120
gctgtcttct caaagactca aaaaacaaac gctcgcaccg aagttgaagt gacggcactg      180
gagaacaaca tcattgtgta caaatttgtg caagatcttc atttctttgt tacgggaggt      240
gaagaagaaa acgagcttgt cttagccagt gtgcttcagg gtctcttcga tgcagtgaat      300
ctcctcctca gaggcaatgt tgataagaga gaggcattgg acaatcttga tctcatcttt      360
ctatgctttg acgaaatcat cgatggcggt attgtcctgg agacggatgc aaatgtgata      420
gcagaaaagg caggaatcaa tagcattgac cctaacgctc ctctatccga gcagacgata      480
agtcaggcac tggcgacggc aagagagcat ttgacaaggt cacttatgaa atga            534
```

<210> SEQ ID NO 18
<211> LENGTH: 143
<212> TYPE: DNA
<213> ORGANISM: Artificial Sequence
<220> FEATURE:
<223> OTHER INFORMATION: Promoter consensus sequence

<400> SEQUENCE: 18

```
gytagagtcc gttatgagay tgtgatgtgg crtctatccr ttgrtggaag aakatttgct       60
ttgctgacaa ctaacaagat tyggtgttat cacaacaaat tggagtcgrm tatatataac      120
gctctagrga aggcycaagt atc                                              143
```

<210> SEQ ID NO 19
<211> LENGTH: 123
<212> TYPE: DNA

<210> SEQ ID NO 19
<213> ORGANISM: Artificial Sequence
<220> FEATURE:
<223> OTHER INFORMATION: UTR consensus sequence 1

<400> SEQUENCE: 19
agtctaataa ctggttcagg atccggttta gagaaaaccg rgagagtgtg acgtgtgraa    60
gtagcrctct ggattctttg agtcatcata gctyaaagtg gacaaaaaac aatattttgt   120
aac                                                                 123

<210> SEQ ID NO 20
<211> LENGTH: 34
<212> TYPE: DNA
<213> ORGANISM: Artificial Sequence
<220> FEATURE:
<223> OTHER INFORMATION: UTR consensus sequence 2

<400> SEQUENCE: 20
gtatcaaaga atttcctctt cgatattttt actt                                34

<210> SEQ ID NO 21
<211> LENGTH: 65
<212> TYPE: DNA
<213> ORGANISM: Artificial Sequence
<220> FEATURE:
<223> OTHER INFORMATION: UTR consensus sequence 3

<400> SEQUENCE: 21
agagagagag agatcttcts tttcaagttc tagagctttc tccgccgatt tcatctcctt    60
tagcc                                                                65

<210> SEQ ID NO 22
<211> LENGTH: 11
<212> TYPE: DNA
<213> ORGANISM: Artificial Sequence
<220> FEATURE:
<223> OTHER INFORMATION: Intron consensus sequence 1

<400> SEQUENCE: 22
gtaattaaaa a                                                         11

<210> SEQ ID NO 23
<211> LENGTH: 253
<212> TYPE: DNA
<213> ORGANISM: Artificial Sequence
<220> FEATURE:
<223> OTHER INFORMATION: Intron consensus sequence 2

<400> SEQUENCE: 23
ctrttttcag tctttcttgc cttcatwttt cacgtytctc tggattctct gctaattttg    60
gattgtggta tggcttttac gttstctagg aaaatcgatg gaaacaaaag aaaamtkaaa   120
tgcatgckat atgttagatt ttgtaattgt ttawaattaa waaraaatta gcagtagttt   180
caagtaagtg gttaaaacca aatagattta tgtaaaactt gcatgtgaaa ttccaactty   240
aaagtttgtt cat                                                      253

```
<210> SEQ ID NO 24
<211> LENGTH: 11
<212> TYPE: DNA
<213> ORGANISM: Artificial Sequence
<220> FEATURE:
<223> OTHER INFORMATION: Intron consensus sequence 3

<400> SEQUENCE: 24
atcttgatag c                                                          11
```

SEED- AND FUNICULUS-PREFERENTIAL PROMOTERS AND USES THEREOF

CROSS REFERENCE TO RELATED APPLICATIONS

This application is a 35 U.S.C. § 371 National Phase of PCT Application No. PCT/EP2017/058388 filed Apr. 7, 2017, which claims priority to European Application No. EP 16165100.5 filed Apr. 13, 2016, the disclosures of each of which are hereby incorporated by reference in their entirety.

FIELD OF THE INVENTION

The present invention relates to materials and methods for the expression of a gene of interest preferentially in seeds and in the funiculus of plants. In particular, the invention provides an expression cassette for regulating seed- and funiculus-preferential expression in plants.

BACKGROUND

Modification of plants to alter and/or improve phenotypic characteristics (such as productivity or quality) requires the overexpression or down-regulation of endogenous genes or the expression of heterologous genes in plant tissues. Such genetic modification relies on the availability of a means to drive and to control gene expression as required. Indeed, genetic modification relies on the availability and use of suitable promoters which are effective in plants and which regulate gene expression so as to give the desired effect(s) in the transgenic plant.

For numerous applications in plant biotechnology a tissue-specific or a tissue-preferential expression profile is advantageous, since beneficial effects of expression in one tissue may have disadvantages in others.

Seed-preferential or seed-specific promoters are useful for expressing or down-regulating genes specifically in the seeds to get the desired function or effect, such as improving disease resistance, herbicide resistance, modifying seed or grain composition or quality, such as modifying starch quality or quantity, modifying oil quality or quantity, modifying amino-acid or protein composition, improving tolerance to biotic or abiotic stress, increasing yield, or altering metabolic pathways in the seeds.

Examples of seed-preferential or seed-specific promoters include the Tonoplast Intrinsic Protein alpha promoter from *Arabidopsis thaliana* (US patent application US2009/0241230), the KNAT411 promoter from *Arabidopsis thaliana* (U.S. Pat. No. 6,342,657), an oleosin promoter, a 2S storage protein promoter or a legumin-like seed storage protein promoter from *Linum usitatissimum* (U.S. Pat. No. 7,642,346), the acyl carrier protein promoter from *Brassica napus* (US Pat. Application No. 1994/0129129), the 3-amylase promoter of barley (US Pat. Application No. 1997/0793599), and the Ha ds10 G1 promoter of sunflower (U.S. Pat. No. 6,759,570).

There remains thus an interest in the isolation of novel seed- and funiculus-preferential promoters having moderate promoter activity. It is thus an objective of the present invention to provide *Brassica* promoters having moderate seed- and funiculus-preferential activity. This objective is solved by the present invention as herein further explained.

SUMMARY

In one aspect, the invention provides an isolated nucleic acid comprising seed- and funiculus-preferential promoter activity selected from the group consisting of (a) a nucleic acid comprising the nucleotide sequence selected from the group: (i) the nucleotide sequence from position 1 to position 1414 of SEQ ID NO: 3, or functional fragment thereof, (ii) the nucleotide sequence from position 1 to position 1364 of SEQ ID NO: 4, or functional fragment thereof, (iii) the nucleotide sequence from position 1 to position 1365 of SEQ ID NO: 5, or functional fragment thereof, (iv) the nucleotide sequence from position 1 to position 1358 of SEQ ID NO: 6, or functional fragment thereof, and (v) the nucleotide sequence from position 1 to position 1363 of SEQ ID NO: 7, or functional fragment thereof; and (b) a nucleic acid comprising a nucleotide sequence having at least 80% sequence identity to any one of (a), or a functional fragment thereof.

In a further embodiment, the nucleic acid described above comprises the nucleotide sequence of SEQ ID NO: 18; the nucleotide sequence of SEQ ID NO: 19; the nucleotide sequence of SEQ ID NO: 20; and the nucleotide sequence of SEQ ID NO: 21.

In another embodiment, said nucleic acid further comprises an intron, the nucleotide sequence of which is selected from the group of: (a) a nucleotide sequence selected from the group: (i) the nucleotide sequence from position 1418 to position 2055 of SEQ ID NO: 3, or a functional fragment thereof, (ii) the nucleotide sequence from position 1368 to position 1650 of SEQ ID NO: 4, or a functional fragment thereof, (iii) the nucleotide sequence from position 1369 to position 2001 of SEQ ID NO: 5, or a functional fragment thereof, (iv) the nucleotide sequence from position 1362 to position 1647 of SEQ ID NO: 6, or a functional fragment thereof, and (v) the nucleotide sequence from position 1367 to position 2001 of SEQ ID NO: 7, or a functional fragment thereof; and (b) a nucleic acid comprising a nucleotide sequence having at least 80% sequence identity to any one of (a), or a functional fragment thereof. The nucleic acid sequence of said intron comprises the nucleotide sequence of SEQ ID NO: 22, the nucleotide sequence of SEQ ID NO: 23, and the nucleotide sequence of SEQ ID NO: 24. In a further embodiment, said nucleic acid comprising the intron has higher seed- and funiculus-preferential promoter activity than the nucleic acid not comprising the intron.

In yet another embodiment the above described nucleic acid is selected from the group: (a) a nucleic acid comprising a nucleotide sequence of any one of SEQ ID NOs: 3 to 7 or a functional fragment thereof; and (b) a nucleic acid comprising a nucleotide sequence having at least 80% sequence identity to any one of SEQ ID NOs: 3 to 7 or a functional fragment thereof.

A further embodiment provides a recombinant gene comprising the nucleic acid according to the invention operably linked to a heterologous nucleic acid sequence encoding an expression product of interest, and optionally a transcription termination and polyadenylation sequence, preferably a transcription termination and polyadenylation region functional in plant cells. In a further embodiment, said expression product of interest is an RNA capable of modulating the expression of a gene or is a protein.

Yet another embodiment provides a host cell, such as an *E. coli* cell, an *Agrobacterium* cell, a yeast cell, an algal cell, or a plant cell, comprising the isolated nucleic acid according to the invention, or the recombinant gene according to the invention.

In further embodiments, a plant and a plant cell are provided comprising the recombinant gene according to the invention. Yet a further embodiment provides seeds obtainable from the plant according to the invention. In another embodiment, the plants or plant parts according to the invention are seed crop plants or seeds.

Yet another embodiment provides a method of producing a transgenic plant comprising the steps of (a) introducing or providing the recombinant gene according to the invention to a plant cell to create transgenic cells; and (b) regenerating transgenic plants from said transgenic cell.

Further provided is a method of effecting seed- and funiculus-preferential expression of a nucleic acid comprising introducing the recombinant gene according to the invention into the genome of a plant, or providing the plant according to the invention. Also provided is a method for altering seed properties of a plant or to produce a commercially relevant product in a plant, said method comprising introducing the recombinant gene according to the invention into the genome of a plant, or providing the plant according to the invention. In another embodiment, said plant is a seed crop plant.

Also provided is the use of the isolated nucleic acid according to the invention to regulate expression of an operably linked nucleic acid in a plant, and the use of the isolated nucleic acid according to the invention, or the recombinant gene according to the invention to alter seed properties of a plant or to produce a commercially relevant product in a plant. In a further embodiment, said plant is a seed crop plant.

Yet another embodiment provides a method of producing food, feed, or an industrial product comprising (a) obtaining the plant or a part thereof, according to the invention; and (b) preparing the food, feed or industrial product from the plant or part thereof. In another embodiment, said food or feed is oil, meal, grain, starch, flour or protein, or said industrial product is biofuel, fiber, industrial chemicals, a pharmaceutical or a nutraceutical.

BRIEF DESCRIPTION OF THE DRAWINGS

FIG. 4: Alignment of the amino acid sequence of different Brassica SLP1 proteins. Amino acid residues conserved in all proteins are indicated by an asterisk, conserved amino acid substitutions are indicated by a colon. The lowest sequence identity between any two SPL1 protein is about 97%.

FIG. 6: Alignment of the about 400 nucleotides upstream of the translation start of the nucleotide sequence of the Brassica PsIp1 promoters from Brassica napus, Brassica juncea, Brassica oleracea and Brassica rapa. The TATA Box is indicated by a frame. The transcription initiation start is indicated in bold. The consensus sequences are underlined and named. Promoter consensus sequence has the sequence of SEQ ID NO: 18, UTR consensus sequence 1 has the sequence of SEQ ID NO: 19, UTR consensus sequence 2 has the sequence of SEQ ID NO: 20, UTR consensus sequence 3 has the sequence of SEQ ID NO: 21.

FIG. 7: Alignment of the translation start codons and of the introns of the nucleotide sequence of the Brassica PsIp1 promoters from Brassica napus, Brassica juncea, Brassica oleracea and Brassica rapa. The translation start codon is indicated in bold. The consensus sequences are underlined and named. Intron consensus sequence 1 has the sequence of SEQ ID NO: 22, intron consensus sequence 2 has the sequence of SEQ ID NO: 23, intron consensus sequence 3 has the sequence of SEQ ID NO: 24.

DETAILED DESCRIPTION

Figure 1:
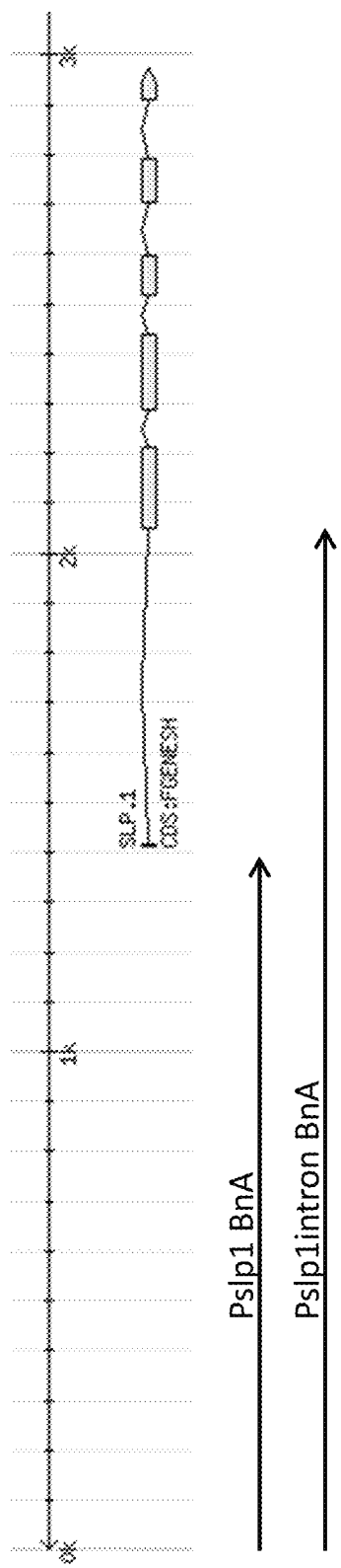
FIG. 1: Graphical display of the gene prediction for SLP1 BnA, using the FGeneSH prediction tool.

The present invention is based on the observation that SEQ ID NOs: 3 to 7 have seed- and funiculus-preferential promoter activity in Brassica.

SEQ ID NOs: 3 to 7 depicts the region upstream (i.e. located 5' upstream of) from the first ATG start codon plus the first intron following the ATG of the SLP1 BnA, SLP1 BnC, SLP1 Br, SLP1 Bo, SLP1 BjA genes respectively.

SLP1 BnA and SLP1 BnC are the two copies present in Brassica napus of the orthologous gene to the Arabidopsis thaliana SLP1 gene At1g60970, which encodes a SNARE-like superfamily protein. SLP1 Br represents the two identical copies present in Brassica rapa of the orthologous gene to the Arabidopsis thaliana SLP1 gene At1g60970. SLP1 Bo is the only copy present in Brassica oleracea of the orthologous gene to the Arabidopsis thaliana SLP1 gene At1g60970. SLP1 BjA is one of the two copies present in Brassica juncea of the orthologous gene to the Arabidopsis thaliana SLP1 gene At1g60970. The SNARE (N-ethylmaleimide-sensitive factor adaptor protein receptor) gene family is a large family of genes encoding membrane associated proteins identified as key players in vesicle trafficking and vesicle fusion. Different members of this family are involved in diverse biological processes in plants, like for example cytokinesis, stress response and shoot gravitropism. Little is known about the expression pattern of the different members of this super family; however, in silico expression analysis in Arabidopsis indicated that the different members have different profiles, with most being either ubiquitously expressed, or preferentially expressed in the pollen (reviewed in Lipka et al. 2007).

In one aspect, the invention provides an isolated nucleic acid comprising seed- and funiculus-preferential promoter activity selected from the group consisting of (a) a nucleic acid comprising the nucleotide sequence selected from the group: (i) the nucleotide sequence from position 1 to position 1414 of SEQ ID NO: 3, or functional fragment thereof, (ii) the nucleotide sequence from position 1 to position 1364 of SEQ ID NO: 4, or functional fragment thereof, (iii) the nucleotide sequence from position 1 to position 1365 of SEQ ID NO: 5, or functional fragment thereof, (iv) the nucleotide sequence from position 1 to position 1358 of SEQ ID NO: 6, or functional fragment thereof, and (v) the nucleotide sequence from position 1 to position 1363 of SEQ ID NO: 7, or functional fragment thereof; and (b) a nucleic acid comprising a nucleotide sequence having at least 80% sequence identity to any one of (a), or a functional fragment thereof.

In a further embodiment, the nucleic acid described above comprises the nucleotide sequence of SEQ ID NO: 18; the nucleotide sequence of SEQ ID NO: 19; the nucleotide sequence of SEQ ID NO: 20; and the nucleotide sequence of SEQ ID NO: 21.

In another embodiment, said nucleic acid further comprises an intron, the nucleotide sequence of which is selected from the group of: (a) a nucleotide sequence selected from the group: (i) the nucleotide sequence from position 1418 to position 2055 of SEQ ID NO: 3, or a functional fragment thereof, (ii) the nucleotide sequence from position 1368 to position 1650 of SEQ ID NO: 4, or a functional fragment thereof, (iii) the nucleotide sequence from position 1369 to position 2001 of SEQ ID NO: 5, or a functional fragment thereof, (iv) the nucleotide sequence from position 1362 to position 1647 of SEQ ID NO: 6, or a functional fragment thereof, and (v) the nucleotide sequence from position 1367 to position 2001 of SEQ ID NO: 7,or a functional fragment thereof; and (b) a nucleic acid comprising a nucleotide sequence having at least 80% sequence identity to any one of (a), or a functional fragment thereof. The nucleic acid sequence of said intron comprises the nucleotide sequence of SEQ ID NO: 22, the nucleotide sequence of SEQ ID NO: 23, and the nucleotide sequence of SEQ ID NO: 24. In a further embodiment, said nucleic acid comprising the intron has higher seed- and funiculus-preferential promoter activity than the nucleic acid not comprising the intron.

In yet another embodiment the above described nucleic acid is selected from the group: (a) a nucleic acid comprising a nucleotide sequence of any one of SEQ ID NOs: 3 to 7 or a functional fragment thereof; and (b) a nucleic acid comprising a nucleotide sequence having at least 80% sequence identity to any one of SEQ ID NOs: 3 to 7 or a functional fragment thereof.

The nucleic acid comprising the seed- and funiculus-preferential promoter activity according to the invention may also be comprised in a larger DNA molecule.

"Seed- and funiculus-preferential promoter activity" in the context of this invention means the promoter activity is at least 2 times, or at least 5 times, or at least 10 times, or at least 20 times, or at least 50 times, or even at least 100 times higher in seeds and in the funiculus than in other tissues. In other words, in seed- and funiculus-preferential promoter activity, transcription of the nucleic acid operably linked to the promoter of the invention in the seeds and the funiculus is at least 2 times, or at least 5 times, or at least 10 times, or at least 20 times, or at least 50 times or even at least 100 times higher than in other tissues. In other words, the seed- and funiculus-preferential promoter drives seed- and funiculus-preferential expression of the nucleic acid operably linked to the seed- and funiculus-preferential promoter.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence. "Functionally linked" is an equivalent term.

The phrases "DNA", "DNA sequence," "nucleic acid sequence," "nucleic acid molecule" "nucleotide sequence" and "nucleic acid" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

As used herein, "promoter" means a region of DNA sequence that is essential for the initiation of transcription of DNA, resulting in the generation of an RNA molecule that is complementary to the transcribed DNA; this region may also be referred to as a "5' regulatory region." Promoters are usually located upstream of the coding sequence to be transcribed and have regions that act as binding sites for RNA polymerase II and other proteins such as transcription factors (trans-acting protein factors that regulate transcription) to initiate transcription of an operably linked gene. Promoters may themselves contain sub-elements (i.e. promoter motifs) such as cis-elements or enhancer domains that regulate the transcription of operably linked genes. The promoters of this invention may be altered to contain "enhancer DNA" to assist in elevating gene expression. As is known in the art, certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (see U.S. Pat. No. 5,593,874), the maize shrunken 1 gene, the light sensitive 1 gene of *Solanum tuberosum*, the *Arabidopsis* histon 4 intron and the heat shock protein 70 gene of *Petunia hybrida* (see U.S. Pat. No. 5,659,122). Thus, as contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed or relative to a promoter driving the expression of a housekeeping gene.

A promoter as used herein may thus include sequences downstream of the transcription start, such as sequences coding the 5' untranslated region (5' UTR) of the RNA, introns located downstream of the transcription start, or even sequences encoding the protein. A functional promoter fragment according to the invention may comprise its own 5'UTR comprising the nucleotide sequence of SEQ ID NO:

3 from nucleotide 1187 to nucleotide 1414, or comprising the nucleotide sequence of SEQ ID No: 4 from nucleotide 1143 to nucleotide 1364, or comprising the nucleotide sequence of SEQ ID No: 5 from nucleotide 1138 to nucleotide 1365, or comprising the nucleotide sequence of SEQ ID No: 6 from nucleotide 1134 to nucleotide 1358, or comprising the nucleotide sequence of SEQ ID No: 7 from nucleotide 1124 to nucleotide 1363. Alternatively, 5'UTR fragments from other *Brassica* SLP1 genes may be used. For example, a promoter fragment of SEQ ID NO: 3 may have the nucleotide sequence of said sequence from position 1187 to 1414 replaced by the nucleotide sequence of SEQ ID NO: 4 from nucleotide 1143 to nucleotide 1364. A promoter fragment of SEQ ID NO: 3 may have the nucleotide sequence of said sequence from position 1187 to 1414 replaced by the nucleotide sequence of SEQ ID NO: 5 from nucleotide 1138 to nucleotide 1365. A promoter fragment of SEQ ID NO: 3 may have the nucleotide sequence of said sequence from position 1187 to 1414 replaced by the nucleotide sequence of SEQ ID NO: 6 from nucleotide 1134 to nucleotide 1358. A promoter fragment of SEQ ID NO: 3 may have the nucleotide sequence of said sequence from position 1187 to 1414 replaced by the nucleotide sequence of SEQ ID NO: 7 from nucleotide 1124 to nucleotide 1363. As another example, a promoter fragment of SEQ ID NO: 4 may have the nucleotide sequence of said sequence from position 1143 to position 1364 replaced by the nucleotide sequence of SEQ ID NO: 3 from nucleotide 1187 to nucleotide 1414. A promoter fragment of SEQ ID NO: 4 may have the nucleotide sequence of said sequence from position 1143 to position 1364 replaced by the nucleotide sequence of SEQ ID NO: 5 from nucleotide 1138 to nucleotide 1365. A promoter fragment of SEQ ID NO: 4 may have the nucleotide sequence of said sequence from position 1143 to position 1364 replaced by the nucleotide sequence of SEQ ID NO: 6 from nucleotide 1134 to nucleotide 1358. A promoter fragment of SEQ ID NO: 4 may have the nucleotide sequence of said sequence from position 1143 to position 1364 replaced by the nucleotide sequence of SEQ ID NO: 7 from nucleotide 1124 to nucleotide 1363. As yet another example, a promoter fragment of SEQ ID NO: 5 may have the nucleotide sequence of said sequence from position 1138 to position 1365 replaced by the nucleotide sequence of SEQ ID NO: 3 from nucleotide 1187 to nucleotide 1414. A promoter fragment of SEQ ID NO: 5 may have the nucleotide sequence of said sequence from position 1138 to position 1365 replaced by the nucleotide sequence of SEQ ID NO: 4 from nucleotide 1143 to nucleotide 1364. A promoter fragment of SEQ ID NO: 5 may have the nucleotide sequence of said sequence from position 1138 to position 1365 replaced by the nucleotide sequence of SEQ ID NO: 6 from nucleotide 1134 to nucleotide 1358. A promoter fragment of SEQ ID NO: 5 may have the nucleotide sequence of said sequence from position 1138 to position 1365 replaced by the nucleotide sequence of SEQ ID NO: 7 from nucleotide 1124 to nucleotide 1363. As another example, a promoter fragment of SEQ ID NO: 6 may have the nucleotide sequence of said sequence from position 1134 to position 1358 replaced by the nucleotide sequence of SEQ ID NO: 3 from nucleotide 1187 to nucleotide 1414. A promoter fragment of SEQ ID NO: 6 may have the nucleotide sequence of said sequence from position 1138 to position 1365 replaced by the nucleotide sequence of SEQ ID NO: 4 from nucleotide 1143 to nucleotide 1364. A promoter fragment of SEQ ID NO: 6 may have the nucleotide sequence of said sequence from position 1138 to position 1365 replaced by the nucleotide sequence of SEQ ID NO: 5 from nucleotide 1138 to nucleotide 1365. A promoter fragment of SEQ ID NO: 6 may have the nucleotide sequence of said sequence from position 1138 to position 1365 replaced by the nucleotide sequence of SEQ ID NO: 7 from nucleotide 1124 to nucleotide 1363. As another example, a promoter fragment of SEQ ID NO: 7 may have the nucleotide sequence of said sequence from position 1124 to position 1363 replaced by the nucleotide sequence of SEQ ID NO: 3 from nucleotide 1187 to nucleotide 1414. A promoter fragment of SEQ ID NO: 7 may have the nucleotide sequence of said sequence from position 1124 to position 1363 replaced by the nucleotide sequence of SEQ ID NO: 4 from nucleotide 1143 to nucleotide 1364. A promoter fragment of SEQ ID NO: 7 may have the nucleotide sequence of said sequence from position 1124 to position 1363 replaced by the nucleotide sequence of SEQ ID NO: 5 from nucleotide 1138 to nucleotide 1365. A promoter fragment of SEQ ID NO: 7 may have the nucleotide sequence of said sequence from position 1124 to position 1363 replaced by the nucleotide sequence of SEQ ID NO: 6 from nucleotide 1134 to nucleotide 1358.

A promoter fragment according to the invention may comprise its own intron comprising the nucleotide sequence of SEQ ID NO: 3 from nucleotide 1418 to nucleotide 2055, or comprising the nucleotide sequence of SEQ ID No: 4 from nucleotide 1368 to nucleotide 1650, or comprising the nucleotide sequence of SEQ ID No: 5 from nucleotide 1369 to nucleotide 2001, or comprising the nucleotide sequence of SEQ ID No: 6 from nucleotide 1362 to nucleotide 1647, or comprising the nucleotide sequence of SEQ ID No: 7 from nucleotide 1367 to nucleotide 2001. Alternatively, intron fragments from other *Brassica* SLP1 genes may be used. For example, a promoter fragment of SEQ ID NO: 3 may have the nucleotide sequence of said sequence from position 1418 to position 2055 replaced by the nucleotide sequence of SEQ ID NO: 4 from nucleotide 1368 to nucleotide 1650. A promoter fragment of SEQ ID NO: 3 may have the nucleotide sequence of said sequence from position 1418 to position 2055 replaced by the nucleotide sequence of SEQ ID NO: 5 from nucleotide 1369 to nucleotide 2001. A promoter fragment of SEQ ID NO: 3 may have the nucleotide sequence of said sequence from position 1418 to position 2055 replaced by the nucleotide sequence of SEQ ID NO: 6 from nucleotide 1362 to nucleotide 1647. A promoter fragment of SEQ ID NO: 3 may have the nucleotide sequence of said sequence from position 1418 to position 2055 replaced by the nucleotide sequence of SEQ ID NO: 7 from nucleotide 1367 to nucleotide 2001. As another example, a promoter fragment of SEQ ID NO: 4 may have the nucleotide sequence of said sequence from position 1368 to position 1650 replaced by the nucleotide sequence of SEQ ID NO: 3 from nucleotide 1418 to nucleotide 2055. A promoter fragment of SEQ ID NO: 4 may have the nucleotide sequence of said sequence from position 1368 to position 1650 replaced by the nucleotide sequence of SEQ ID NO: 5 from nucleotide 1369 to nucleotide 2001. A promoter fragment of SEQ ID NO: 4 may have the nucleotide sequence of said sequence from position 1368 to position 1650 replaced by the nucleotide sequence of SEQ ID NO: 6 from nucleotide 1362 to nucleotide 1647. A promoter fragment of SEQ ID NO: 4 may have the nucleotide sequence of said sequence from position 1368 to position 1650 replaced by the nucleotide sequence of SEQ ID NO: 7 from nucleotide 1367 to nucleotide 2001. As yet another example, a promoter fragment of SEQ ID NO: 5 may have the nucleotide sequence of said sequence from position 1369 to position 2001 replaced by the nucleotide sequence of SEQ ID NO: 3 from nucleotide 1418 to nucleotide 2055. A promoter fragment of SEQ ID NO: 5 may have the nucleotide sequence of said sequence from position 1369 to position 2001 replaced by the nucleotide sequence of SEQ ID NO: 4 from nucleotide 1368 to nucleotide 1650. A promoter fragment of SEQ ID NO: 5 may have the nucleotide sequence of said sequence from position 1369 to position 2001 replaced by the nucleotide sequence of SEQ ID NO: 6 from nucleotide 1362 to nucleotide 1647. A promoter fragment of SEQ ID NO: 5 may have the nucleotide sequence of said sequence from position 1369 to position 2001 replaced by the nucleotide sequence of SEQ ID NO: 7 from nucleotide 1367 to nucleotide 2001. As another example, a promoter fragment of SEQ ID NO: 6 may have the nucleotide sequence of said sequence from position 1362 to position 1647 replaced by the nucleotide sequence of SEQ ID NO: 3 from nucleotide 1418 to nucleotide 2055. A promoter fragment of SEQ ID NO: 6 may have the nucleotide sequence of said sequence from position 1362 to position 1647 replaced by the nucleotide sequence of SEQ ID NO: 4 from nucleotide 1368 to nucleotide 1650. A promoter fragment of SEQ ID NO: 6 may have the nucleotide sequence of said sequence from position 1362 to position 1647 replaced by the nucleotide sequence of SEQ ID NO: 5 from nucleotide 1369 to nucleotide 2001. A promoter fragment of SEQ ID NO: 6 may have the nucleotide sequence of said sequence from position 1362 to position 1647 replaced by the nucleotide sequence of SEQ ID NO: 7 from nucleotide 1367 to nucleotide 2001. As another example, a promoter fragment of SEQ ID NO: 7 may have the nucleotide sequence of said sequence from position 1367 to position 2001 replaced by the nucleotide sequence of SEQ ID NO: 3 from nucleotide 1418 to nucleotide 2055. A promoter fragment of SEQ ID NO: 7 may have the nucleotide sequence of said sequence from position 1367 to position 2001 replaced by the nucleotide sequence of SEQ ID NO: 4 from nucleotide 1368 to nucleotide 1650. A promoter fragment of SEQ ID NO: 7 may have the nucleotide sequence of said sequence from position 1367 to position 2001 replaced by the nucleotide sequence of SEQ ID NO: 5 from nucleotide 1369 to nucleotide 2001. A promoter fragment of SEQ ID NO: 7 may have the nucleotide sequence of said sequence from position 1367 to position 2001 replaced by the nucleotide sequence of SEQ ID NO: 6 from nucleotide 1362 to nucleotide 1647.

Such a promoter fragment may be at least about 400 bp, at least about 500 bp, at least about 600 bp, at least about 700 bp, at least about 800 bp, at least about 900 bp, at least about 1000 bp, at least about 1100 bp, at least about 1200 bp, or at least about 1300 bp upstream of the first ATG start codon of the SLP1 transcripts and have seed- and funiculus-preferential promoter activity. In combination with the above described promoter fragments, a promoter fragment according to the invention may thus comprise the nucleotide sequence of SEQ ID NO: 3 from the nucleotide at position 1014 to the nucleotide at position 1414, the nucleotide sequence of SEQ ID NO: 3 from the nucleotide at position 914 to the nucleotide at position 1414, the nucleotide sequence of SEQ ID NO: 3 from the nucleotide at position 814 to the nucleotide at position 1414, the nucleotide sequence of SEQ ID NO: 3 from the nucleotide at position 714 to the nucleotide at position 1414, the nucleotide sequence of SEQ ID NO: 3 from the nucleotide at position 614 to the nucleotide at position 1414, the nucleotide sequence of SEQ ID NO: 3 from the nucleotide at position 514 to the nucleotide at position 1414, the nucleotide sequence of SEQ ID NO: 3 from the nucleotide at position 414 to the nucleotide at position 1414, the nucleotide sequence of SEQ ID NO: 3 from the nucleotide at position 314 to the nucleotide at position 1414, the nucleotide sequence of SEQ ID NO: 3 from the nucleotide at position 214 to the nucleotide at position 1414, the nucleotide sequence of SEQ ID NO: 3 from the nucleotide at position 114 to the nucleotide at position 1414, the nucleotide sequence of SEQ ID NO: 3 from the nucleotide at position 14 to the nucleotide at position 1414, or the nucleotide sequence of SEQ ID NO: 3 from the nucleotide at position 1 to the nucleotide at position 1414. A promoter fragment according to the invention may also comprise the nucleotide sequence of SEQ ID No: 4 from the nucleotide at position 964 to the nucleotide at position 1364, the nucleotide sequence of SEQ ID No: 4 from the nucleotide at position 864 to the nucleotide at position 1364, the nucleotide sequence of SEQ ID No: 4 from the nucleotide at position 764 to the nucleotide at position 1364, the nucleotide sequence of SEQ ID No: 4 from the nucleotide at position 664 to the nucleotide at position 1364, the nucleotide sequence of SEQ ID No: 4 from the nucleotide at position 564 to the nucleotide at position 1364, the nucleotide sequence of SEQ ID No: 4 from the nucleotide at position 464 to the nucleotide at position 1364, the nucleotide sequence of SEQ ID No: 4 from the nucleotide at position 364 to the nucleotide at position 1364, the nucleotide sequence of SEQ ID No: 4 from the nucleotide at position 264 to the nucleotide at position 1364, the nucleotide sequence of SEQ ID No: 4 from the nucleotide at position 164 to the nucleotide at position 1364, the nucleotide sequence of SEQ ID No: 4 from the nucleotide at position 64 to the nucleotide at position 1364, or the nucleotide sequence of SEQ ID No: 4 from the nucleotide at position 1 to the nucleotide at position 1364. A promoter fragment according to the invention may also comprise the nucleotide sequence of SEQ ID No: 5 from the nucleotide at position 965 to the nucleotide at position 1365, the nucleotide sequence of SEQ ID No: 5 from the nucleotide at position 865 to the nucleotide at position 1365, the nucleotide sequence of SEQ ID No: 5 from the nucleotide at position 765 to the nucleotide at position 1365, the nucleotide sequence of SEQ ID No: 5 from the nucleotide at position 665 to the nucleotide at position 1365, the nucleotide sequence of SEQ ID No: 5 from the nucleotide at position 565 to the nucleotide at position 1365, the nucleotide sequence of SEQ ID No: 5 from the nucleotide at position 465 to the nucleotide at position 1365, the nucleotide sequence of SEQ ID No: 5 from the nucleotide at position 365 to the nucleotide at position 1365, the nucleotide sequence of SEQ ID No: 5 from the nucleotide at position 265 to the nucleotide at position 1365, the nucleotide sequence of SEQ ID No: 5 from the nucleotide at position 165 to the nucleotide at position 1365, the nucleotide sequence of SEQ ID No: 5 from the nucleotide at position 65 to the nucleotide at position 1365, or the nucleotide sequence of SEQ ID No: 5 from the nucleotide at position 1 to the nucleotide at position 1365. A promoter fragment according to the invention may also comprise the nucleotide sequence of SEQ ID No: 6 from the nucleotide at position 958 to the nucleotide at position 1358, the nucleotide sequence of SEQ ID No: 6 from the nucleotide at position 858 to the nucleotide at position 1358, the nucleotide sequence of SEQ ID No: 6 from the nucleotide at position 758 to the nucleotide at position 1358, the nucleotide sequence of SEQ ID No: 6 from the nucleotide at position 658 to the nucleotide at position 1358, the nucleotide sequence of SEQ ID No: 6 from the nucleotide at position 558 to the nucleotide at position 1358, the nucleotide sequence of SEQ ID No: 6 from the nucleotide at position 458 to the nucleotide at position 1358, the nucleotide sequence of SEQ ID No: 6 from the nucleotide at position 358 to the nucleotide at position 1358, the nucleotide sequence of SEQ ID No: 6 from the nucleotide at position 258 to the nucleotide at position 1358, the nucleotide sequence of SEQ ID No: 6 from the nucleotide at position 158 to the nucleotide at position 1358, the nucleotide sequence of SEQ ID No: 6 from the nucleotide at position 58 to the nucleotide at position 1358, or the nucleotide sequence of SEQ ID No: 6 from the nucleotide at position 1 to the nucleotide at position 1358. A promoter fragment according to the invention may also comprise the nucleotide sequence of SEQ ID No: 7 from the nucleotide at position 963 to the nucleotide at position 1363, the nucleotide sequence of SEQ ID No: 7 from the nucleotide at position 863 to the nucleotide at position 1363, the nucleotide sequence of SEQ ID No: 7 from the nucleotide at position 763 to the nucleotide at position 1363, the nucleotide sequence of SEQ ID No: 7 from the nucleotide at position 663 to the nucleotide at position 1363, the nucleotide sequence of SEQ ID No: 7 from the nucleotide at position 563 to the nucleotide at position 1363, the nucleotide sequence of SEQ ID No: 7 from the nucleotide at position 463 to the nucleotide at position 1363, the nucleotide sequence of SEQ ID No: 7 from the nucleotide at position 363 to the nucleotide at position 1363, the nucleotide sequence of SEQ ID No: 7 from the nucleotide at position 263 to the nucleotide at position 1363, the nucleotide sequence of SEQ ID No: 7 from the nucleotide at position 163 to the nucleotide at position 1363, the nucleotide sequence of SEQ ID No: 7 from the nucleotide at position 63 to the nucleotide at position 1363, or the nucleotide sequence of SEQ ID No: 7 from the nucleotide at position 1 to the nucleotide at position 1363.

Such a promoter fragment may be at least about 400 bp, at least about 500 bp, at least about 600 bp, at least about 700 bp, at least about 800 bp, at least about 900 bp, at least about 1000 bp, at least about 1100 bp, at least about 1200 bp, or at least about 1300 bp upstream of the first ATG start codon of the SLP1 transcripts and at least about 300 bp, at least about 400 bp, at least about 500 bp or at least about 600 bp of the intron downstream of the first ATG start codon of the SLP1 gene and have seed- and funiculus-preferential promoter activity. In such promoter fragments the first ATG start codon may optionally be present immediately before the intron fragment. In combination with the above described promoter fragments, a promoter fragment according to the invention may thus comprise the nucleotide sequence of SEQ ID NO: 3 from the nucleotide at position 1014 to the nucleotide at position 1414 and from the nucleotide position 1418 to the nucleotide position 1718, the nucleotide sequence of SEQ ID NO: 3 from the nucleotide at position 914 to the nucleotide at position 1414 and from the nucleotide at position 1418 to the nucleotide at position 1718, the nucleotide sequence of SEQ ID NO: 3 from the nucleotide at position 814 to the nucleotide at position 1414 and from the nucleotide at position 1418 to the nucleotide at position 1718, the nucleotide sequence of SEQ ID NO: 3 from the nucleotide at position 714 to the nucleotide at position 1414 and from the nucleotide at position 1418 to the nucleotide at position 1718, the nucleotide sequence of SEQ ID NO: 3 from the nucleotide at position 614 to the nucleotide at position 1414 and from the nucleotide at position 1418 to the nucleotide at position 1718, the nucleotide sequence of SEQ ID NO: 3 from the nucleotide at position 514 to the nucleotide at position 1414 and from the nucleotide at position 1418 to the nucleotide at position 1718, the nucleotide sequence of SEQ ID NO: 3 from the nucleotide at position 414 to the nucleotide at position 1414 and from the nucleotide at position 1418 to the nucleotide at position 1718, the nucleotide sequence of SEQ ID NO: 3 from the nucleotide at position 314 to the nucleotide at position 1414 and from the nucleotide at position 1418 to the nucleotide at position 1718, the nucleotide sequence of SEQ ID NO: 3 from the nucleotide at position 214 to the nucleotide at position 1414 and from the nucleotide at position 1418 to the nucleotide at the position 1718, the nucleotide sequence of SEQ ID NO: 3 from the nucleotide at position 114 to the nucleotide at position 1414 and from the nucleotide at position 1418 to the nucleotide at position 1718, the nucleotide sequence of SEQ ID NO: 3 from the nucleotide at position 14 to the nucleotide at position 1414 and from the nucleotide at position 1418 to the nucleotide at position 1718, the nucleotide sequence of SEQ ID NO: 3 from the nucleotide at position 1 to the nucleotide at position 1414 and from the nucleotide at position 1418 to the nucleotide at position 1718, the nucleotide sequence of SEQ ID NO: 3 from the nucleotide at position 1014 to the nucleotide at position 1414 and from the nucleotide at position 1418 to the nucleotide at position 1818, the nucleotide sequence of SEQ ID NO: 3 from the nucleotide at position 914 to the nucleotide at position 1414 and from the nucleotide at position 1418 to the nucleotide at position 1818, the nucleotide sequence of SEQ ID NO: 3 from the nucleotide at position 814 to the nucleotide at position 1414 and from the nucleotide at position 1418 to the nucleotide at position 1818, the nucleotide sequence of SEQ ID NO: 3 from the nucleotide at position 714 to the nucleotide at position 1414 and from the nucleotide at position 1418 to the nucleotide at position 1818, the nucleotide sequence of SEQ ID NO: 3 from the nucleotide at position 614 to the nucleotide at position 1414 and from the nucleotide at position 1418 to the nucleotide at position 1818, the nucleotide sequence of SEQ ID NO: 3 from the nucleotide at position 514 to the nucleotide at position 1414 and from the nucleotide at position 1418 to the nucleotide at position 1818, the nucleotide sequence of SEQ ID NO: 3 from the nucleotide at position 414 to the nucleotide at position 1414 and from the nucleotide at position 1418 to the nucleotide at position 1818, the nucleotide sequence of SEQ ID NO: 3 from the nucleotide at position 314 to the nucleotide at position 1414 and from the nucleotide at position 1418 to the nucleotide at position 1818, the nucleotide sequence of SEQ ID NO: 3 from the nucleotide at position 214 to the nucleotide at position 1414 and from the nucleotide at position 1418 to the nucleotide at position 1818, the nucleotide sequence of SEQ ID NO: 3 from the nucleotide at position 114 to the nucleotide at position 1414 and from the nucleotide at position 1418 to the nucleotide at position 1818, the nucleotide sequence of SEQ ID NO: 3 from the nucleotide at position 14 to the nucleotide at position 1414 and from the nucleotide at position 1418 to the nucleotide at position 1818, the nucleotide sequence of SEQ ID NO: 3 from the nucleotide at position 1 to the nucleotide at position 1414 and from the nucleotide at position 1418 to the nucleotide at position 1818, the nucleotide sequence of SEQ ID NO: 3 from the nucleotide at position 1014 to the nucleotide at position 1414 and from the nucleotide at position 1418 to the nucleotide at position 1918, the nucleotide sequence of SEQ ID NO: 3 from the nucleotide at position 914 to the nucleotide at position 1414 and from the nucleotide at position 1418 to the nucleotide at position 1918, the nucleotide sequence of SEQ ID NO: 3 from the nucleotide at position 814 to the nucleotide at position 1414 and from the nucleotide at position 1418 to the nucleotide at position 1918, the nucleotide sequence of SEQ ID NO: 3 from the nucleotide at position 714 to the nucleotide at position 1414 and from the nucleotide at position 1418 to the nucleotide at position 1918, the nucleotide sequence of SEQ ID NO: 3 from the nucleotide at position 614 to the nucleotide at position 1414 and from the nucleotide at position 1418 to the nucleotide at position 1918, the nucleotide sequence of SEQ ID NO: 3 from the nucleotide at position 514 to the nucleotide at position 1414 and from the nucleotide at position 1418 to the nucleotide at position 1918, the nucleotide sequence of SEQ ID NO: 3 from the nucleotide at position 414 to the nucleotide at position 1414 and from the nucleotide at position 1418 to the nucleotide at position 1918, the nucleotide sequence of SEQ ID NO: 3 from the nucleotide at position 314 to the nucleotide at position 1414 and from the nucleotide at position 1418 to the nucleotide at position 1918, the nucleotide sequence of SEQ ID NO: 3 from the nucleotide at position 214 to the nucleotide at position 1414 and from the nucleotide at position 1418 to the nucleotide at position 1918, the nucleotide sequence of SEQ ID NO: 3 from the nucleotide at position 114 to the nucleotide at position 1414 and from the nucleotide at position 1418 to the nucleotide at position 1918, the nucleotide sequence of SEQ ID NO: 3 from the nucleotide at position 14 to the nucleotide at position 1414 and from the nucleotide at position 1418 to the nucleotide at position 1918, the nucleotide sequence of SEQ ID NO: 3 from the nucleotide at position 1 to the nucleotide at position 1414 and from the nucleotide at position 1418 to the nucleotide at position 1918, the nucleotide sequence of SEQ ID NO: 3 from the nucleotide at position 1014 to the nucleotide at position 1414 and from the nucleotide at position 1418 to the nucleotide at position 2018, the nucleotide sequence of SEQ ID NO: 3 from the nucleotide at position 914 to the nucleotide at position 1414 and from the nucleotide at position 1418 to the nucleotide at position 2018, the nucleotide sequence of SEQ ID NO: 3 from the nucleotide at position 814 to the nucleotide at position 1414 and from the nucleotide at position 1418 to the nucleotide at position 2018, the nucleotide sequence of SEQ ID NO: 3 from the nucleotide at position 714 to the nucleotide at position 1414 and from the nucleotide at position 1418 to the nucleotide at position 2018, the nucleotide sequence of SEQ ID NO: 3 from the nucleotide at position 614 to the nucleotide at position 1414 and from the nucleotide at position 1418 to the nucleotide at position 2018, the nucleotide sequence of SEQ ID NO: 3 from the nucleotide at position 514 to the nucleotide at position 1414 and from the nucleotide at position 1418 to the nucleotide at position 2018, the nucleotide sequence of SEQ ID NO: 3 from the nucleotide at position 414 to the nucleotide at position 1414 and from the nucleotide at position 1418 to the nucleotide at position 2018, the nucleotide sequence of SEQ ID NO: 3 from the nucleotide at position 314 to the nucleotide at position 1414 and from the nucleotide at position 1418 to the nucleotide at position 2018, the nucleotide sequence of SEQ ID NO: 3 from the nucleotide at position 214 to the nucleotide at position 1414 and from the nucleotide at position 1418 to the nucleotide at position 2018, the nucleotide sequence of SEQ ID NO: 3 from the nucleotide at position 114 to the nucleotide at position 1414 and from the nucleotide at position 1418 to the nucleotide at position 2018, the nucleotide sequence of SEQ ID NO: 3 from the nucleotide at position 14 to the nucleotide at position 1414 and from the nucleotide at position 1418 to the nucleotide at position 2018, the nucleotide sequence of SEQ ID NO: 3 from the nucleotide at position 1 to the nucleotide at position 1414 and from the nucleotide at position 1418 to the nucleotide at position 2018, the nucleotide sequence of SEQ ID NO: 3 from the nucleotide at position 1014 to the nucleotide at position 1414 and from the nucleotide at position 1418 to the nucleotide at position 2055, the nucleotide sequence of SEQ ID NO: 3 from the nucleotide at position 914 to the nucleotide at position 1414 and from the nucleotide at the position 1418 to the nucleotide at position 2055, the nucleotide sequence of SEQ ID NO: 3 from the nucleotide at position 814 to the nucleotide at position 1414 and from the nucleotide at position 1418 to the nucleotide at position 2055, the nucleotide sequence of SEQ ID NO: 3 from the nucleotide at position 714 to the nucleotide at position 1414 and from the nucleotide at position 1418 to the nucleotide at position 2055, the nucleotide sequence of SEQ ID NO: 3 from the nucleotide at position 614 to the nucleotide at position 1414 and from the nucleotide at position 1418 to the nucleotide at position 2055, the nucleotide sequence of SEQ ID NO: 3 from the nucleotide at position 514 to the nucleotide at position 1414 and from the nucleotide at position 1418 to the nucleotide at position 2055, the nucleotide sequence of SEQ ID NO: 3 from the nucleotide at position 414 to the nucleotide at position 1414 and from the nucleotide at position 1418 to the nucleotide at position 2055, the nucleotide sequence of SEQ ID NO: 3 from the nucleotide at position 314 to the nucleotide at position 1414 and from the nucleotide at position 1418 to the nucleotide at position 2055, the nucleotide sequence of SEQ ID NO: 3 from the nucleotide at position 214 to the nucleotide at position 1414 and from the nucleotide at position 1418 to the nucleotide at position 2055, the nucleotide sequence of SEQ ID NO: 3 from the nucleotide at position 114 to the nucleotide at position 1414 and from the nucleotide at position 1418 to the nucleotide at position 2055, the nucleotide sequence of SEQ ID NO: 3 from the nucleotide at position 14 to the nucleotide at position 1414 and from the nucleotide at position 1418 to the nucleotide at position 2055, or the nucleotide sequence of SEQ ID NO: 3 from the nucleotide at position 1 to the nucleotide at position 1414 and from the nucleotide at position 1418 to the nucleotide at position 2055. A promoter fragment according to the invention may also comprise the nucleotide sequence of SEQ ID No: 4 from the nucleotide at position 964 to the nucleotide at position 1364 and from the nucleotide at position 1368 to the nucleotide at position 1650, the nucleotide sequence of SEQ ID No: 4 from the nucleotide at position 864 to the nucleotide at position 1364 and from the nucleotide at position 1368 to the nucleotide at position 1650, the nucleotide sequence of SEQ ID No: 4 from the nucleotide at position 764 to the nucleotide at position 1364 and from the nucleotide at position 1368 to the nucleotide at position 1650, the nucleotide sequence of SEQ ID No: 4 from the nucleotide at position 664 to the nucleotide at position 1650, the nucleotide sequence of SEQ ID No: 4 from the nucleotide at position 564 to the nucleotide at position 1364 and from the nucleotide at position 1368 to the nucleotide at position 1650, the nucleotide sequence of SEQ ID No: 4 from the nucleotide at position 464 to the nucleotide at position 1364 and from the nucleotide at position 1368 to the nucleotide at position 1650, the nucleotide sequence of SEQ ID No: 4 from the nucleotide at position 364 to the nucleotide at position 1364 and from the nucleotide at position 1368 to the nucleotide at position 1650, the nucleotide sequence of SEQ ID No: 4 from the nucleotide at position 264 to the nucleotide at position 1364 and from the nucleotide at position 1368 to the nucleotide at position 1650, the nucleotide sequence of SEQ ID No: 4 from the nucleotide at position 164 to the nucleotide at position 1364 and from the nucleotide 1368 to the nucleotide at position 1650, the nucleotide sequence of SEQ ID No: 4 from the nucleotide at position 64 to the nucleotide at position 1364 and from the nucleotide at position 1368 to the nucleotide at position 165, or the nucleotide sequence of SEQ ID No: 4 from the nucleotide at position 1 to the nucleotide at position 1364 and from the nucleotide at position 1368 to the nucleotide at position 1650. A promoter fragment according to the invention may also comprise the nucleotide sequence of SEQ ID No: 5 from the nucleotide at position 965 to the nucleotide at position 1365 and from the nucleotide sequence 1369 to the nucleotide position 1669, the nucleotide sequence of SEQ ID No: 5 from the nucleotide at position 865 to the nucleotide at position 1365 and from the nucleotide position 1369 to the nucleotide position 1669, the nucleotide sequence of SEQ ID No: 5 from the nucleotide at position 765 to the nucleotide at position 1365 and from the nucleotide position 1369 to the nucleotide position 1669, the nucleotide sequence of SEQ ID No: 5 from the nucleotide at position 665 to the nucleotide at position 1365 and from the nucleotide at position 1369 to the nucleotide at position 1669, the nucleotide sequence of SEQ ID No: 5 from the nucleotide at position 565 to the nucleotide at position 1365 and from the nucleotide at position1369 to the nucleotide at position 1669, the nucleotide sequence of SEQ ID No: 5 from the nucleotide at position 465 to the nucleotide at position 1365 and from the nucleotide at position 1369 to the nucleotide at position 1669, the nucleotide sequence of SEQ ID No: 5 from the nucleotide at position 365 to the nucleotide at position 1365 and from the nucleotide at position 1369 to the nucleotide at position 1669, the nucleotide sequence of SEQ ID No: 5 from the nucleotide at position 265 to the nucleotide at position 1365 and from the nucleotide at position 1369 to the nucleotide at position 1669, the nucleotide sequence of SEQ ID No: 5 from the nucleotide at position 165 to the nucleotide at position 1365 and from the nucleotide at position 1369 to the nucleotide at position 1669, the nucleotide sequence of SEQ ID No: 5 from the nucleotide at position 65 to the nucleotide at position 1365 and from the nucleotide at position 1369 to the nucleotide at position 1669, the nucleotide sequence of SEQ ID No: 5 from the nucleotide at position 1 to the nucleotide at position 1365 and from the nucleotide at position 1369 to the nucleotide at position 1669, the nucleotide sequence of SEQ ID No: 5 from the nucleotide at position 965 to the nucleotide at position 1365 and from the nucleotide at position 1369 to the nucleotide at position 1769, the nucleotide sequence of SEQ ID No: 5 from the nucleotide at position 865 to the nucleotide at position 1365 and from the nucleotide at position 1369 to the nucleotide at position 1769, the nucleotide sequence of SEQ ID No: 5 from the nucleotide at position 765 to the nucleotide at position 1365 and from the nucleotide at position 1369 to the nucleotide at position 1769, the nucleotide sequence of SEQ ID No: 5 from the nucleotide at position 665 to the nucleotide at position 1365 and from the nucleotide at position 1369 to the nucleotide at position 1769, the nucleotide sequence of SEQ ID No: 5 from the nucleotide at position 565 to the nucleotide at position 1365 and from the nucleotide at position 1369 and to the nucleotide at position 1769, the nucleotide sequence of SEQ ID No: 5 from the nucleotide at position 465 to the nucleotide at position 1365 and from the nucleotide at position 1369 to the nucleotide at position 1769, the nucleotide sequence of SEQ ID No: 5 from the nucleotide at position 365 to the nucleotide at position 1365 and from the nucleotide at position 1369 to the nucleotide at position 1769, the nucleotide sequence of SEQ ID No: 5 from the nucleotide at position 265 to the nucleotide at position 1365 and from the nucleotide at position 1369 to the nucleotide at position 1769, the nucleotide sequence of SEQ ID No: 5 from the nucleotide at position 165 to the nucleotide at position 1365 and from the nucleotide at position 1369 to the nucleotide at position 1769, the nucleotide sequence of SEQ ID No: 5 from the nucleotide at position 65 to the nucleotide at position 1365 and from the nucleotide at position 1369 to the nucleotide at position 1769, the nucleotide sequence of SEQ ID No: 5 from the nucleotide at position 1 to the nucleotide at position 1365 and from the nucleotide at position 1369 to the nucleotide at position 1769, the nucleotide sequence of SEQ ID No: 5 from the nucleotide at position 965 to the nucleotide at position 1365 and from the nucleotide at position 1369 to the nucleotide at position 1869, the nucleotide sequence of SEQ ID No: 5 from the nucleotide at position 865 to the nucleotide at position 1365 and from the nucleotide at position 1369 to the nucleotide at position 1869, the nucleotide sequence of SEQ ID No: 5 from the nucleotide at position 765 to the nucleotide at position 1365 and from the nucleotide at position 1369 to the nucleotide at position 1869, the nucleotide sequence of SEQ ID No: 5 from the nucleotide at position 665 to the nucleotide at position 1365 and from the nucleotide at position 1369 to the nucleotide at position 1869, the nucleotide sequence of SEQ ID No: 5 from the nucleotide at position 565 to the nucleotide at position 1365 and from the nucleotide at position 1369 to the nucleotide at position 1869, the nucleotide sequence of SEQ ID No: 5 from the nucleotide at position 465 to the nucleotide at position 1365 and from the nucleotide at position 1369 to the nucleotide at position 1869, the nucleotide sequence of SEQ ID No: 5 from the nucleotide at position 365 to the nucleotide at position 1365 and from the nucleotide at position 1369 to the nucleotide at position 1869, the nucleotide sequence of SEQ ID No: 5 from the nucleotide at position 265 to the nucleotide at position 1365 and from the nucleotide at position 1369 to the nucleotide at position 1869, the nucleotide sequence of SEQ ID No: 5 from the nucleotide at position 165 to the nucleotide at position 1365 and from the nucleotide at position 1369 to the nucleotide at position 1869, the nucleotide sequence of SEQ ID No: 5 from the nucleotide at position 65 to the nucleotide at position 1365 and from the nucleotide at position 1369 to the nucleotide at position 1869, the nucleotide sequence of SEQ ID No: 5 from the nucleotide at position 1 to the nucleotide at position 1365 and from the nucleotide at position 1369 to the nucleotide at position 1869, the nucleotide sequence of SEQ ID No: 5 from the nucleotide at position 965 to the nucleotide at position 1365 and from the nucleotide at position 1369 to the nucleotide at position 1969, the nucleotide sequence of SEQ ID No: 5 from the nucleotide at position 865 to the nucleotide at position 1365 and from the nucleotide at position 1369 to the nucleotide at position 1969, the nucleotide sequence of SEQ ID No: 5 from the nucleotide at position 765 to the nucleotide at position 1365 and from the nucleotide at position 1369 to the nucleotide at position 1969, the nucleotide sequence of SEQ ID No: 5 from the nucleotide at position 665 to the nucleotide at position 1365 and from the nucleotide at position 1369 to the nucleotide at position 1969, the nucleotide sequence of SEQ ID No: 5 from the nucleotide at position 565 to the nucleotide at position 1365 and from the nucleotide at position 1369 to the nucleotide at position 1969, the nucleotide sequence of SEQ ID No: 5 from the nucleotide at position 465 to the nucleotide at position 1365 and from the nucleotide at position 1369 to the nucleotide at position 1969, the nucleotide sequence of SEQ ID No: 5 from the nucleotide at position 365 to the nucleotide at position 1365 and from the nucleotide at position 1369 to the nucleotide at position 1969, the nucleotide sequence of SEQ ID No: 5 from the nucleotide at position 265 to the nucleotide at position 1365 and from the nucleotide at position 1369 to the nucleotide at position 1969, the nucleotide sequence of SEQ ID No: 5 from the nucleotide at position 165 to the nucleotide at position 1365 and from the nucleotide at position 1369 to the nucleotide at position 1969, the nucleotide sequence of SEQ ID No: 5 from the nucleotide at position 65 to the nucleotide at position 1365 and from the nucleotide at position 1369 to the nucleotide at position 1969, the nucleotide sequence of SEQ ID No: 5 from the nucleotide at position 1 to the nucleotide at position 1365 and from the nucleotide at position 1369 to the nucleotide at position 1969, the nucleotide sequence of SEQ ID No: 5 from the nucleotide at position 965 to the nucleotide at position 1365 and from the nucleotide at position 1369 to the nucleotide at position 2001, the nucleotide sequence of SEQ ID No: 5 from the nucleotide at position 865 to the nucleotide at position 1365 and from the nucleotide at position 1369 to the nucleotide at position 2001, the nucleotide sequence of SEQ ID No: 5 from the nucleotide at position 765 to the nucleotide at position 1365 and from the nucleotide at position 1369 to the nucleotide at position 2001, the nucleotide sequence of SEQ ID No: 5 from the nucleotide at position 665 to the nucleotide at position 1365 and from the nucleotide at position 1369 to the nucleotide at position 2001, the nucleotide sequence of SEQ ID No: 5 from the nucleotide at position 565 to the nucleotide at position 1365 and from the nucleotide at position 1369 to the nucleotide at position 2001, the nucleotide sequence of SEQ ID No: 5 from the nucleotide at position 465 to the nucleotide at position 1365 and from the nucleotide at position 1369 to the nucleotide at position 2001, the nucleotide sequence of SEQ ID No: 5 from the nucleotide at position 365 to the nucleotide at position 1365 and from the nucleotide at position 1369 to the nucleotide at position 2001, the nucleotide sequence of SEQ ID No: 5 from the nucleotide at position 265 to the nucleotide at position 1365 and from the nucleotide at position 1369 to the nucleotide at position 2001, the nucleotide sequence of SEQ ID No: 5 from the nucleotide at position 165 to the nucleotide at position 1365 and from the nucleotide at position 1369 to the nucleotide at position 2001, the nucleotide sequence of SEQ ID No: 5 from the nucleotide at position 65 to the nucleotide at position 1365 and from the nucleotide at position 1369 to the nucleotide at position 2001, or the nucleotide sequence of SEQ ID No: 5 from the nucleotide at position 1 to the nucleotide at position 1365 and from the nucleotide at position 1369 to the nucleotide at position 2001. A promoter fragment according to the invention may also comprise the nucleotide sequence of SEQ ID No: 6 from the nucleotide at position 958 to the nucleotide at position 1358 and from the nucleotide at position 1362 to the nucleotide at position 1647, the nucleotide sequence of SEQ ID No: 6 from the nucleotide at position 858 to the nucleotide at position 1358 and from the nucleotide at position 1362 to the nucleotide at position 1647, the nucleotide sequence of SEQ ID No: 6 from the nucleotide at position 758 to the nucleotide at position 1358 and from the nucleotide at position 1362 to the nucleotide at position 1647, the nucleotide sequence of SEQ ID No: 6 from the nucleotide at position 658 to the nucleotide at position 1358 and from the nucleotide at position 1362 to the nucleotide at position 1647, the nucleotide sequence of SEQ ID No: 6 from the nucleotide at position 558 to the nucleotide at position 1358 and from the nucleotide at position 1362 to the nucleotide at position 1647, the nucleotide sequence of SEQ ID No: 6 from the nucleotide at position 458 to the nucleotide at position 1358 and from the nucleotide at position 1362 to the nucleotide at position 1647, the nucleotide sequence of SEQ ID No: 6 from the nucleotide at position 358 to the nucleotide at position 1358 and from the nucleotide at position 1362 to the nucleotide at position 1647, the nucleotide sequence of SEQ ID No: 6 from the nucleotide at position 258 to the nucleotide at position 1358 and from the nucleotide at position 1362 to the nucleotide at position 1647, the nucleotide sequence of SEQ ID No: 6 from the nucleotide at position 158 to the nucleotide at position 1358 and from the nucleotide at position 1362 to the nucleotide at position 1647, the nucleotide sequence of SEQ ID No: 6 from the nucleotide at position 58 to the nucleotide at position 1358 and from the nucleotide at position 1362 to the nucleotide at position 1647, or the nucleotide sequence of SEQ ID No: 6 from the nucleotide at position 1 to the nucleotide at position 1358 and from the nucleotide at position 1362 to the nucleotide at position 1647. A promoter fragment according to the invention may also comprise the nucleotide sequence of SEQ ID No: 7 from the nucleotide at position 963 to the nucleotide at position 1363 and from the nucleotide at position 1367 to the nucleotide at position 1667, the nucleotide sequence of SEQ ID No: 7 from the nucleotide at position 863 to the nucleotide at position 1363 and from the nucleotide at position 1367 to the nucleotide at position 1667, the nucleotide sequence of SEQ ID No: 7 from the nucleotide at position 763 to the nucleotide at position 1363 and from the nucleotide at position 1367 to the nucleotide at position 1667, the nucleotide sequence of SEQ ID No: 7 from the nucleotide at position 663 to the nucleotide at position 1363 and from the nucleotide at position 1367 to the nucleotide at position 1667, the nucleotide sequence of SEQ ID No: 7 from the nucleotide at position 563 to the nucleotide at position 1363 and from the nucleotide at position 1367 to the nucleotide at position 1667, the nucleotide sequence of SEQ ID No: 7 from the nucleotide at position 463 to the nucleotide at position 1363 and from the nucleotide at position 1367 to the nucleotide at position 1667, the nucleotide sequence of SEQ ID No: 7 from the nucleotide at position 363 to the nucleotide at position 1363 and from the nucleotide at position 1367 to the nucleotide at position 1667, the nucleotide sequence of SEQ ID No: 7 from the nucleotide at position 263 to the nucleotide at position 1363 and from the nucleotide at position 1367 to the nucleotide at position 1667, the nucleotide sequence of SEQ ID No: 7 from the nucleotide at position 163 to the nucleotide at position 1363 and from the nucleotide at position 1367 to the nucleotide at position 1667, the nucleotide sequence of SEQ ID No: 7 from the nucleotide at position 63 to the nucleotide at position 1363 and from the nucleotide at position 1367 to the nucleotide at position 1667, the nucleotide sequence of SEQ ID No: 7 from the nucleotide at position 1 to the nucleotide at position 1363 and from the nucleotide at position 1367 to the nucleotide at position 1667, the nucleotide sequence of SEQ ID No: 7 from the nucleotide at position 963 to the nucleotide at position 1363 and from the nucleotide at position 1367 to the nucleotide at position 1767, the nucleotide sequence of SEQ ID No: 7 from the nucleotide at position 863 to the nucleotide at position 1363 and from the nucleotide at position 1367 to the nucleotide at position 1767, the nucleotide sequence of SEQ ID No: 7 from the nucleotide at position 763 to the nucleotide at position 1363 and from the nucleotide at position 1367 to the nucleotide at position 1767, the nucleotide sequence of SEQ ID No: 7 from the nucleotide at position 663 to the nucleotide at position 1363 and from the nucleotide at position 1367 to the nucleotide at position 1767, the nucleotide sequence of SEQ ID No: 7 from the nucleotide at position 563 to the nucleotide at position 1363 and from the nucleotide at position 1367 to the nucleotide at position 1767, the nucleotide sequence of SEQ ID No: 7 from the nucleotide at position 463 to the nucleotide at position 1363 and from the nucleotide at position 1367 to the nucleotide at position 1767, the nucleotide sequence of SEQ ID No: 7 from the nucleotide at position 363 to the nucleotide at position 1363 and from the nucleotide at position 1367 to the nucleotide at position 1767, the nucleotide sequence of SEQ ID No: 7 from the nucleotide at position 263 to the nucleotide at position 1363 and from the nucleotide at position 1367 to the nucleotide at position 1767, the nucleotide sequence of SEQ ID No: 7 from the nucleotide at position 163 to the nucleotide at position 1363 and from the nucleotide at position 1367 to the nucleotide at position 1767, the nucleotide sequence of SEQ ID No: 7 from the nucleotide at position 63 to the nucleotide at position 1363 and from the nucleotide at position 1367 to the nucleotide at position 1767, the nucleotide sequence of SEQ ID No: 7 from the nucleotide at position 1 to the nucleotide at position 1363 and from the nucleotide at position 1367 to the nucleotide at position 1767, the nucleotide sequence of SEQ ID No: 7 from the nucleotide at position 963 to the nucleotide at position 1363 and from the nucleotide at position 1367 to the nucleotide at position 1867, the nucleotide sequence of SEQ ID No: 7 from the nucleotide at position 863 to the nucleotide at position 1363 and from the nucleotide at position 1367 to the nucleotide at position 1867, the nucleotide sequence of SEQ ID No: 7 from the nucleotide at position 763 to the nucleotide at position 1363 and from the nucleotide at position 1367 to the nucleotide at position 1867, the nucleotide sequence of SEQ ID No: 7 from the nucleotide at position 663 to the nucleotide at position 1363 and from the nucleotide at position 1367 to the nucleotide at position 1867, the nucleotide sequence of SEQ ID No: 7 from the nucleotide at position 563 to the nucleotide at position 1363 and from the nucleotide at position 1367 to the nucleotide at position 1867, the nucleotide sequence of SEQ ID No: 7 from the nucleotide at position 463 to the nucleotide at position 1363 and from the nucleotide at position 1367 to the nucleotide at position 1867, the nucleotide sequence of SEQ ID No: 7 from the nucleotide at position 363 to the nucleotide at position 1363 and from the nucleotide at position 1367 to the nucleotide at position 1867, the nucleotide sequence of SEQ ID No: 7 from the nucleotide at position 263 to the nucleotide at position 1363 and from the nucleotide at position 1367 to the nucleotide at position 1867, the nucleotide sequence of SEQ ID No: 7 from the nucleotide at position 163 to the nucleotide at position 1363 and from the nucleotide at position 1367 to the nucleotide at position 1867, the nucleotide sequence of SEQ ID No: 7 from the nucleotide at position 63 to the nucleotide at position 1363 and from the nucleotide at position 1367 to the nucleotide at position 1867, the nucleotide sequence of SEQ ID No: 7 from the nucleotide at position 1 to the nucleotide at position 1363 and from the nucleotide at position 1367 to the nucleotide at position 1867, the nucleotide sequence of SEQ ID No: 7 from the nucleotide at position 963 to the nucleotide at position 1363 and from the nucleotide at position 1367 to the nucleotide at position 1967, the nucleotide sequence of SEQ ID No: 7 from the nucleotide at position 863 to the nucleotide at position 1363 and from the nucleotide at position 1367 to the nucleotide at position 1967, the nucleotide sequence of SEQ ID No: 7 from the nucleotide at position 763 to the nucleotide at position 1363 and from the nucleotide at position 1367 to the nucleotide at position 1967, the nucleotide sequence of SEQ ID No: 7 from the nucleotide at position 663 to the nucleotide at position 1363 and from the nucleotide at position 1367 to the nucleotide at position 1967, the nucleotide sequence of SEQ ID No: 7 from the nucleotide at position 563 to the nucleotide at position 1363 and from the nucleotide at position 1367 to the nucleotide at position 1967, the nucleotide sequence of SEQ ID No: 7 from the nucleotide at position 463 to the nucleotide at position 1363 and from the nucleotide at position 1367 to the nucleotide at position 1967, the nucleotide sequence of SEQ ID No: 7 from the nucleotide at position 363 to the nucleotide at position 1363 and from the nucleotide at position 1367 to the nucleotide at position 1967, the nucleotide sequence of SEQ ID No: 7 from the nucleotide at position 263 to the nucleotide at position 1363 and from the nucleotide at position 1367 to the nucleotide at position 1967, the nucleotide sequence of SEQ ID No: 7 from the nucleotide at position 163 to the nucleotide at position 1363 and from the nucleotide at position 1367 to the nucleotide at position 1967, the nucleotide sequence of SEQ ID No: 7 from the nucleotide at position 63 to the nucleotide at position 1363 and from the nucleotide at position 1367 to the nucleotide at position 1967, the nucleotide sequence of SEQ ID No: 7 from the nucleotide at position 1 to the nucleotide at position 1363 and from the nucleotide at position 1367 to the nucleotide at position 1967, the nucleotide sequence of SEQ ID No: 7 from the nucleotide at position 963 to the nucleotide at position 1363 and from the nucleotide at position 1367 to the nucleotide at position 2001, the nucleotide sequence of SEQ ID No: 7 from the nucleotide at position 863 to the nucleotide at position 1363 and from the nucleotide at position 1367 to the nucleotide at position 2001, the nucleotide sequence of SEQ ID No: 7 from the nucleotide at position 763 to the nucleotide at position 1363 and from the nucleotide at position 1367 to the nucleotide at position 2001, the nucleotide sequence of SEQ ID No: 7 from the nucleotide at position 663 to the nucleotide at position 1363 and from the nucleotide at position 1367 to the nucleotide at position 2001, the nucleotide sequence of SEQ ID No: 7 from the nucleotide at position 563 to the nucleotide at position 1363 and from the nucleotide at position 1367 to the nucleotide at position 2001, the nucleotide sequence of SEQ ID No: 7 from the nucleotide at position 463 to the nucleotide at position 1363 and from the nucleotide at position 1367 to the nucleotide at position 2001, the nucleotide sequence of SEQ ID No: 7 from the nucleotide at position 363 to the nucleotide at position 1363 and from the nucleotide at position 1367 to the nucleotide at position 2001, the nucleotide sequence of SEQ ID No: 7 from the nucleotide at position 263 to the nucleotide at position 1363 and from the nucleotide at position 1367 to the nucleotide at position 2001, the nucleotide sequence of SEQ ID No: 7 from the nucleotide at position 163 to the nucleotide at position 1363 and from the nucleotide at position 1367 to the nucleotide at position 2001, the nucleotide sequence of SEQ ID No: 7 from the nucleotide at position 63 to the nucleotide at position 1363 and from the nucleotide at position 1367 to the nucleotide at position 2001, or the nucleotide sequence of SEQ ID No: 7 from the nucleotide at position 1 to the nucleotide at position 1363 and from the nucleotide at position 1367 to the nucleotide at position 2001.

Promoter activity for a functional promoter fragment in seeds may be determined by those skilled in the art, for example using analysis of RNA accumulation produced from the nucleic acid which is operably linked to the promoter as described herein, whereby the nucleic acid which is operably linked to the promoter can be the nucleic acid which is naturally linked to the promoter, i.e. the endogenous gene of which expression is driven by the promoter.

The seed- and funiculus-preferential expression capacity of the identified or generated fragments of the promoters of the invention can be conveniently tested by determining levels of the transcript of which expression is naturally driven by the promoter of the invention, i.e. endogenous transcript levels, such as, for example, using the methods as described herein in the Examples. Further, the seed- and funiculus-preferential expression capacity of the identified or generated fragments of the promoters of the invention can be conveniently tested by operably linking such DNA molecules to a nucleotide sequence encoding an easy scorable marker, e.g. a beta-glucuronidase gene, introducing such a chimeric gene into a plant and analyzing the expression pattern of the marker in seeds and in the funiculus as compared with the expression pattern of the marker in other parts of the plant. Other candidates for a marker (or a reporter gene) are chloramphenicol acetyl transferase (CAT) and proteins with fluorescent properties, such as green fluorescent protein (GFP) from *Aequora victoria* or proteins with luminescent properties such as the *Renilla luciferase* or the bacterial lux operon. To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins, which are easily measured, including, but not limited to, chloramphenicol acetyl transferase (CAT), beta-glucuronidase (GUS), green fluorescent protein (GFP), beta-galactosidase (beta-GAL), and luciferase. The expression cassette containing the reporter gene under the control of the promoter can be introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography. The level of enzyme activity corresponds to the amount of enzyme that was made, which in turn reveals the level of expression and the seed-preferential functionality from the promoter or promoter fragment of interest. This level of expression can also be compared to other promoters to determine the relative strength of the promoter under study. Once activity and functionality is confirmed, additional mutational and/or deletion analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then again introduced in cells and their activity and/or functionality determined.

The activity or strength of a promoter may be measured in terms of the amount of mRNA or protein accumulation it specifically produces, relative to the total amount of mRNA or protein. The promoter preferably expresses an operably linked nucleic acid sequence at a level greater than about 0.001%, about 0.002%, more preferably greater than about 0.005% of the total mRNA. Alternatively, the activity or strength of a promoter may be expressed relative to a well-characterized promoter (for which transcriptional activity was previously assessed).

It will herein further be clear that equivalent seed- and funiculus-preferential promoters can be isolated from other plants. To this end, equivalent promoters can be isolated using the coding sequences of the genes driven by the promoters of any one of SEQ ID NOs: 3 to 7 to screen a genomic library (e.g. by hybridization or in silico) of a crop of interest. When sufficient identity between the coding sequences is obtained (for example, higher than 85% identity) then promoter regions can be isolated upstream of the orthologous genes.

Suitable to the invention are nucleic acids comprising seed- and funiculus-preferential promoter activity which comprise a nucleotide sequence having at least 40%, at least 50%, or at least 60%, or at least 70%, or at least 80%, or at least 85%, or at least 90%, or at least 95%, or at least 98% sequence identity to the herein described promoters and promoter regions or functional fragments thereof and are also referred to as variants. The term "variant" with respect to the transcription regulating nucleotide sequences SEQ ID NOs: 3 to 7 of the invention is intended to mean substantially similar sequences. Naturally occurring allelic variants such as these can be identified with the use of well-known molecular biology techniques, as, for example, with polymerase chain reaction (PCR) and hybridization techniques as herein outlined before. Variant nucleotide sequences also include synthetically derived nucleotide sequences, such as those generated, for example, by using site-directed mutagenesis of any one of SEQ ID NOs: 3 to 7. Generally, nucleotide sequence variants of the invention will have at least 40%, 50%, 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence or a functional fragment thereof. Derivatives of the DNA molecules disclosed herein may include, but are not limited to, deletions of sequence, single or multiple point mutations, alterations at a particular restriction enzyme site, addition of functional elements, or other means of molecular modification which may enhance, or otherwise alter promoter expression. Techniques for obtaining such derivatives are well-known in the art (see, for example, J. F. Sambrook, D. W. Russell, and N. Irwin (2000) Molecular Cloning: A Laboratory Manual, 3$^{rd}$ edition Volumes 1, 2, and 3. Cold Spring Harbor Laboratory Press). For example, one of ordinary skill in the art may delimit the functional elements within the promoters disclosed herein and delete any non-essential elements. Functional elements may be modified or combined to increase the utility or expression of the sequences of the invention for any particular application. Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules. As used herein, the term "percent sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman (Waterman, M. S. Introduction to Computational Biology: Maps, sequences and genomes. Chapman & Hall. London (1995), the homology alignment algorithm of Needleman and Wunsch (J. Mol. Biol., 48:443-453 (1970), the search for similarity method of Pearson and Lipman (Proc. Natl. Acad. Sci., 85:2444 (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

A nucleic acid comprising a nucleotide sequence having at least 80% sequence identity to any one of SEQ ID NO: 3 to 7 can thus be a nucleic acid comprising a nucleotide sequence having at least 80%, or at least 85%, or at least 90%, or at least 95%, or at least 98%, or 100% sequence identity to any one of SEQ ID NOs: 3 to 7.

A "functional fragment" of a nucleic acid comprising seed-preferential promoter denotes a nucleic acid comprising a stretch of the nucleic acid sequences of any one of SEQ ID NOs: 3 to 7, or of the nucleic acid having at least 80% sequence identity to any one of SEQ ID NOs: 3 to 7 which still exerts the desired function, i.e. which has seed-preferential promoter activity. Assays for determining seed-preferential promoter activity are provided herein. Preferably, the functional fragment of the seed-preferential promoter contains the conserved promoter motifs, such as, for example, conserved promoter motifs as described in DoOP (doop.abc.hu, databases of Orthologous Promoters, Barta E. et al (2005) *Nucleic Acids Research* Vol. 33, D86-D90). A functional fragment may be a fragment of at least about 400 bp, at least about 500 bp, at least about 600 bp, at least about 700 bp, at least about 800 bp, at least about 900 bp, at least about 1000 bp, at least about 1100 bp; at least about 1200 bp, or at least about 1300 bp upstream of the first ATG start codon of the SLP1 transcripts and at least about 300 bp, at least about 400 bp, at least about 500 bp or at least about 600 bp downstream of the first ATG start codon of the SLP1 gene and have seed- and funiculus-preferential promoter activity.

A nucleic acid comprising the nucleotide sequence of any one of SEQ ID NO: 3 to 7 which further comprises insertion, deletion, substitution of at least 1 nucleotide up to 20 nucleotides, at least 1 nucleotide up to 15 nucleotides, at least 1 nucleotide up to 10 nucleotides, at least 1 nucleotide up to 5 nucleotides, at least 1 nucleotide up to 4 nucleotides, at least 1 nucleotide up to 3 nucleotides, or even at least 1 nucleotide up to 2 nucleotides may cover at least about 300 bp, at least about 400 bp, at least about 500 bp, at least about 600 bp, at least about 700 bp, at least about 800 bp, at least about 900 bp, at least about 1000 bp, at least about 1100 bp; at least about 1200 bp, or at least about 1300 bp from the translation start site.

A number of highly conserved regions (consensus sequences) were identified on the promoter sequence disclosed herein.

Variants of the promoter described herein include those which comprise the identified consensus sequences—promoter consensus sequence (SEQ ID NO: 18), UTR consensus sequence 1 (SEQ ID NO: 19), UTR consensus sequence 2 (SEQ ID NO: 20), UTR consensus sequence 3 (SEQ ID NO: 21), intron consensus sequence 1 (SEQ ID NO: 22), intron consensus sequence 2 (SEQ ID NO: 23) and/or intron consensus sequence 3 (SEQ ID NO: 24)—, but have otherwise been modified to delete nucleotide stretches within the sequence which are not needed for the promoter to be functional in seed- and funiculus-preferential manner. For example, any nucleotide stretch located between the consensus sequences and/or between the transcriptional start and the first consensus sequence may be at least partially deleted to result in a shorter nucleotide sequence than the about 2 kb sequence of SEQ ID NOs: 3, 5 and 7, or than the about 1.7 kb of SEQ ID NOs: 4 and 6.

"Isolated nucleic acid", used interchangeably with "isolated DNA" as used herein refers to a nucleic acid not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

A further embodiment provides a recombinant gene comprising the nucleic acid according to the invention operably linked to a heterologous nucleic acid sequence encoding an expression product of interest, and optionally a transcription termination and polyadenylation sequence, preferably a transcription termination and polyadenylation region functional in plant cells. In a further embodiment, said expression product of interest an RNA capable of modulating the expression of a gene or is a protein.

The term "expression product" refers to a product of transcription. Said expression product can be the transcribed RNA. It is understood that the RNA which is produced is a biologically active RNA. Said expression product can also be a peptide, a polypeptide, or a protein, when said biologically active RNA is an mRNA and said protein is produced by translation of said mRNA.

Alternatively, the heterologous nucleic acid, operably linked to the promoters of the invention, may also code for an RNA capable of modulating the expression of a gene. Said RNA capable of modulating the expression of a gene can be an RNA which reduces expression of a gene. Said RNA can reduce the expression of a gene for example through the mechanism of RNA-mediated gene silencing.

Said RNA capable of modulating the expression of a gene can be a silencing RNA down-regulating expression of a target gene. As used herein, "silencing RNA" or "silencing RNA molecule" refers to any RNA molecule, which upon introduction into a plant cell, reduces the expression of a target gene. Such silencing RNA may e.g. be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having 95% sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference). The hpRNA may be classified as long hpRNA, having long, sense and antisense regions which can be largely complementary, but need not be entirely complementary (typically larger than about 200 bp, ranging between 200 and 1000 bp). hpRNA can also be rather small ranging in size from about 30 to about 42 bp, but not much longer than 94 bp (see WO04/073390, herein incorporated by reference). Silencing RNA may also be artificial micro-RNA molecules as described e.g. in WO2005/052170, WO2005/047505 or US 2005/0144667, or ta-siRNAs as described in WO2006/074400 (all documents incorporated herein by reference). Said RNA capable of modulating the expression of a gene can also be an RNA ribozyme.

Said RNA capable of modulating the expression of a gene can modulate, preferably down-regulate, the expression of other genes (i.e. target genes) comprised within the seeds or funiculus or even of genes present within a pathogen or pest that feeds upon the seeds of the transgenic plant such as a virus, fungus, insect, bacteria.

The nucleic acid sequence heterologous to the promoters according to the invention may generally be any nucleic acid sequence effecting increased, altered (e.g. in a different organ) or reduced level of transcription of a gene for which such expression modulation is desired. The nucleic acid sequence can for example encode a protein of interest. Exemplary genes for which an increased or reduced level of transcription may be desired in the seeds are e.g. nucleic acids that can provide an agriculturally or industrially important feature in seeds. Suitable heterologous nucleic acid sequences of interest include nucleic acids modulating expression of genes conferring resistance to diseases, stress tolerance genes, genes involved in at different stages of fatty acid biosynthesis or degradation, in acyl editing, in storage compound storage or breakdown, genes encoding epoxidases, hydroxylases, cytochrome P450 mono-oxygenases, desaturases, tocopherol biosynthetic enzymes, carotenoid biosynthesis enzymes, amino acid biosynthetic enzymes, steroid pathway enzymes, starch branching enzymes, genes encoding proteins involved in starch synthesis, glycolysis, carbon metabolism, oxidative pentose phosphate cycle, protein synthesis, organelle organization and biogenesis, DNA metabolism, DNA replication, cell cycle, cell organization and biogenesis, cell proliferation, chromosome organization and biogenesis, microtubule-based processes, microtubule-based movement, cytoskeleton-dependent intracellular transport, cytoskeleton organization and biogenesis, chromatin assembly or disassembly, DNA-dependent DNA replication, chromosome organization and biogenesis, DNA packaging, establishment and/or maintenance of chromatin architecture, regulation of progression through the cell cycle, regulation of the cell cycle, nucleobase, nucleoside, nucleotide and nucleic acid metabolism, chromatin assembly, macromolecule biosynthesis, intracellular transport, establishment of cellular localization, cellular localization, nucleosome assembly, macromolecule metabolism, or M-phase; genes involved in secondary metabolism or genes involved in seed and/or seed coat architecture.

Genes involved in the fatty acid biosynthesis or degradation include but are not limited to genes encoding an acyl-CoA synthetase, a glycerol-phosphate acyltransferase, an O-acyltransferase, a lyso-phosphatidic acid acyltransferase, a phosphatidic acid phosphatase, a diacylglycerol acyltransferase, an oleate desaturases, a linoleate desaturases, an acyl-CoA hydroxylase, an acyl-lipid hydroxylase, a fatty acid epoxidase, a phospholipid:sterol acyltransferase, a phospholipid: diacylglycerol acyltransferase, a diacylglycerol transacylase, a lysophosphatidylcholine acyltransferase, a phosphatidylcholine:diacylglycerol cholinephosphotransferase, an acyl-CoA elongase, an acyl-lipid elongase, a phosphatidylglycerol-phosphate synthetase, a phosphatidylglycerol-phosphate phosphatase, a CDP-diacylglycerol synthetase, a phosphatidylinositol synthase, a phosphatidylserine synthase, a choline kinase, an ethanolamine kinase, a CDP-choline synthetase, a CDP-ethanolamine synthetase, a phosphatidylserine decarboxylase, a lipoxygenase, a phospholipase, a lipase, a carboxylesterase, a fatty alcohol reductase, a wax ester synthase, a bifunctional acyltranferases/wax synthase, a ketoacyl-CoA synthase, a ketoacyl-CoA reductase, a hydroxylacyl-CoA dehydrase, an enoyl-CoA reductase, an alcohol-forming fatty acyl-CoA reductase, an aldehyde-forming fatty acyl-CoA reductase, an aldehyde decarbonylase, a wax ester hydrolase, a glycerol-3-P-dehydrogenase, a CDP-choline:1,2-diacylglycerol cholinephosphotransferase, an oxidase, a ketosphinganine reductase, a ceramide synthase, an acylglycerophosphorylcholine acyltransferase, an acylglycerol-phosphate acyltransferase, a phosphoethanolamine N-methyltransferase, a ceramide sphingobase desaturase, a glucosylceramide synthase, a acyl-ceramide synthase, a triacylglycerol lipase, a monoacylglycerol lipase, an acyl-CoA oxidase, an hydroxyacyl-CoA dehydrogenase, a dienoyl-CoA reductase, a fatty acid omega-alcohol oxidase, a monoacylglycerol lipase, an acyl-CoA oxidase, a hydroxyacyl-CoA dehydrogenase, a dienoyl-CoA reductase, a fatty acid omega-alcohol oxidase, a fatty acid/acyl-CoA transporter, a acyl-CoA dehydrogenase, a diacylglycerol-phosphate kinase, a lysophosphatidic acic phosphatase, a peroxygenase; a Δ4-desaturase; a Δ5-desaturase, a Δ6-desaturase; a Δ9-desaturase, a Δ12-desaturase or a Δ15-desaturase.

Genes involved in cell proliferation include but are not limited to genes encoding Da1 (Li et al., 2008, Genes Dev 22:1331, WO2015/067943), Da2, EOD1 or EOD3 (WO2015/022192, PCT/GB/2013/050072).

A "transcription termination and polyadenylation region" as used herein is a sequence that drives the cleavage of the nascent RNA, whereafter a poly(A) tail is added at the resulting RNA 3' end, functional in plant cells. Transcription termination and polyadenylation signals functional in plant cells include, but are not limited to, 3'nos, 3'35S, 3'his and 3'g7.

The term "protein" interchangeably used with the term "polypeptide" as used herein describes a group of molecules consisting of more than 30 amino acids, whereas the term "peptide" describes molecules consisting of up to 30 amino acids. Proteins and peptides may further form dimers, trimers and higher oligomers, i.e. consisting of more than one (poly)peptide molecule. Protein or peptide molecules forming such dimers, trimers etc. may be identical or non-identical. The corresponding higher order structures are, consequently, termed homo- or heterodimers, homo- or heterotrimers etc. The terms "protein" and "peptide" also refer to naturally modified proteins or peptides wherein the modification is effected e.g. by glycosylation, acetylation, phosphorylation and the like. Such modifications are well known in the art.

The term "heterologous" refers to the relationship between two or more nucleic acid or protein sequences that are derived from different sources. For example, a promoter is heterologous with respect to an operably linked DNA region, such as a coding sequence if such a combination is not normally found in nature. In addition, a particular sequence may be "heterologous" with respect to a cell or organism into which it is inserted (i.e. does not naturally occur in that particular cell or organism).

The term "recombinant gene" refers to any gene that contains: a) DNA sequences, including regulatory and coding sequences that are not found together in nature, or b) sequences encoding parts of proteins not naturally adjoined, or c) parts of promoters that are not naturally adjoined. Accordingly, a recombinant gene may comprise regulatory sequences and coding sequences that are derived from different sources, or comprise regulatory sequences, and coding sequences derived from the same source, but arranged in a manner different from that found in nature.

Any of the promoters and heterologous nucleic acid sequences described above may be provided in a recombinant vector. A recombinant vector typically comprises, in a 5' to 3' orientation: a promoter to direct the transcription of a nucleic acid sequence and a nucleic acid sequence. The recombinant vector may further comprise a 3' transcriptional terminator, a 3' polyadenylation signal, other untranslated nucleic acid sequences, transit and targeting nucleic acid sequences, selectable markers, enhancers, and operators, as desired. The wording "5' UTR" refers to the untranslated region of DNA upstream, or 5' of the coding region of a gene and "3' UTR" refers to the untranslated region of DNA downstream, or 3' of the coding region of a gene. Means for preparing recombinant vectors are well known in the art. Methods for making recombinant vectors particularly suited to plant transformation are described in U.S. Pat. Nos. 4,971,908, 4,940,835, 4,769,061 and 4,757,011. Typical vectors useful for expression of nucleic acids in higher plants are well known in the art and include vectors derived from the tumor-inducing (Ti) plasmid of *Agrobacterium tumefaciens*. One or more additional promoters may also be provided in the recombinant vector. These promoters may be operably linked, for example, without limitation, to any of the nucleic acid sequences described above. Alternatively, the promoters may be operably linked to other nucleic acid sequences, such as those encoding transit peptides, selectable marker proteins, or antisense sequences. These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity.

The recombinant vector may also contain one or more additional nucleic acid sequences. These additional nucleic acid sequences may generally be any sequences suitable for use in a recombinant vector. Such nucleic acid sequences include, without limitation, any of the nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e., a single operon).

Yet another embodiment provides a host cell, such as an *E. coli* cell, an *Agrobacterium* cell, a yeast cell, an algal cell, or a plant cell, comprising the isolated nucleic acid according to the invention, or the recombinant gene according to the invention.

Other nucleic acid sequences may also be introduced into the host cell along with the promoter and structural nucleic acid sequence, e. g. also in connection with the vector of the invention. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

In further embodiments, a plant and a plant cell are provided comprising the recombinant gene according to the invention. Yet a further embodiment provides seeds obtainable from the plant according to the invention. In another embodiment, the plants or seeds according to the invention are seed crop plants or seeds.

The plant cell or plant comprising the recombinant gene according to the invention can be a plant cell or a plant comprising a recombinant gene of which either the promoter, or the heterologous nucleic acid sequence operably linked to said promoter, are heterologous with respect to the plant cell. Such plant cells or plants may be transgenic plant in which the recombinant gene is introduced via transformation. Alternatively, the plant cell of plant may comprise the promoter according to the invention derived from the same species operably linked to a nucleic acid which is also derived from the same species, i.e. neither the promoter nor the operably linked nucleic acid is heterologous with respect to the plant cell, but the promoter is operably linked to a nucleic acid to which it is not linked in nature. A recombinant gene can be introduced in the plant or plant cell via transformation, such that both the promoter and the operably linked nucleotide are at a position in the genome in which they do not occur naturally. Alternatively, the promoter according to the invention can be integrated in a targeted manner in the genome of the plant or plant cell upstream of an endogenous nucleic acid encoding an expression product of interest, i.e. to modulate the expression pattern of an endogenous gene. The promoter that is integrated in a targeted manner upstream of an endogenous nucleic acid can be integrated in cells of a plant species from which it is originally derived, or in cells of a heterologous plant species. Alternatively, a heterologous nucleic acid can be integrated in a targeted manner in the genome of the plant or plant cell downstream of the promoter according to the invention, such that said heterologous nucleic acid is expressed seed-preferentially. Said heterologous nucleic acid is a nucleic acid which is heterologous with respect to the promoter, i.e. the combination of the promoter with said heterologous nucleic acid is not normally found in nature. Said heterologous nucleic acid may be a nucleic acid which is heterologous to said plant species in which it is inserted, but it may also naturally occur in said plant species at a different location in the plant genome. Said promoter or said heterologous nucleic acid can be integrated in a targeted manner in the plant genome via targeted sequence insertion, using, for example, the methods as described in WO2005/049842.

Plants comprising at least two recombinant genes according to the invention wherein the nucleic acid comprising seed- and funiculus-preferential promoter activity is different in each recombinant gene are, for example, plants comprising a first recombinant gene comprising a nucleotide sequence having at least 95% sequence identity to SEQ ID NO: 3 or a functional fragment thereof, and a second recombinant gene comprising a nucleotide sequence having at least 95% sequence identity to any one of SEQ ID NO: 4 to SEQ ID NO: 7 or a functional fragment thereof. It will be clear that, when the first recombinant gene comprises a nucleotide sequence having at least 95% sequence identity to SEQ ID NO: x or a functional fragment thereof, wherein SEQ ID NO: x is selected from any one of SEQ ID NO: 3 to SEQ ID NO: 7, the second recombinant gene may comprise a nucleotide sequence having at least 95% sequence identity to any one of the sequences according to the invention or a functional fragment thereof, except to SEQ ID NO: x. Said plants are suitable to express different genes with the same tissue-specificity, however without the negative features associated with the repeated use of one promoter, such as gene silencing or recombination of a vector comprising the recombinant genes. The at least two recombinant genes according to the invention may be present at one locus in the genome of said plant, and may be derived from the same transforming DNA molecule.

Plants according to the invention may comprise one or more recombinant genes according to the invention, but may in addition contain a recombinant gene comprising a nucleic acid comprising promoter activity which is preferential or specific to other plant tissues, such as apical meristem, flower buds, cotyledons, flowers, pods, roots, and leaves, operably linked to a nucleic acid sequence encoding an expression product of interest. The recombinant gene according to the invention and the recombinant gene comprising a nucleic acid comprising another promoter activity may be present at one locus and may be derived from the same transforming DNA molecule.

Yet another embodiment provides a method of producing a transgenic plant comprising the steps of (a) introducing or providing the recombinant gene according to the invention to a plant cell to create transgenic cells; and (b) regenerating transgenic plants from said transgenic cell.

"Introducing" in connection with the present application relates to the placing of genetic information in a plant cell or plant by artificial means. This can be effected by any method known in the art for introducing RNA or DNA into plant cells, protoplasts, calli, roots, tubers, seeds, stems, leaves, seedlings, embryos, pollen and microspores, other plant tissues, or whole plants. "Introducing" also comprises stably integrating into the plant's genome. Introducing the recombinant gene can be performed by transformation.

The term "transformation" herein refers to the introduction (or transfer) of nucleic acid into a recipient host such as a plant or any plant parts or tissues including plant cells, protoplasts, calli, roots, tubers, seeds, stems, leaves, seedlings, embryos and pollen. Plants containing the transformed nucleic acid sequence are referred to as "transgenic plants". Transformed, transgenic and recombinant refer to a host organism such as a plant into which a heterologous nucleic acid molecule (e.g. an expression cassette or a recombinant vector) has been introduced. The nucleic acid can be stably integrated into the genome of the plant.

As used herein, the phrase "transgenic plant" refers to a plant having an introduced nucleic acid stably introduced into a genome of the plant, for example, the nuclear or plastid genomes. In other words, plants containing transformed nucleic acid sequence are referred to as "transgenic plants". Transgenic and recombinant refer to a host organism such as a plant into which a heterologous nucleic acid molecule (e.g. the promoter, the chimeric gene or the vector as described herein) has been introduced. The nucleic acid can be stably integrated into the genome of the plant.

Transformation methods are well known in the art and include *Agrobacterium*-mediated transformation. *Agrobacterium*-mediated transformation of cotton has been described e.g. in U.S. Pat. No. 5,004,863, in U.S. Pat. No. 6,483,013 and WO2000/71733. Plants may also be transformed by particle bombardment: Particles of gold or tungsten are coated with DNA and then shot into young plant cells or plant embryos. This method also allows transformation of plant plastids. Viral transformation (transduction) may be used for transient or stable expression of a gene, depending on the nature of the virus genome. The desired genetic material is packaged into a suitable plant virus and the modified virus is allowed to infect the plant. The progeny of the infected plants is virus free and also free of the inserted gene. Suitable methods for viral transformation are described or further detailed e. g. in WO 90/12107, WO 03/052108 or WO 2005/098004. Further suitable methods well-known in the art are microinjection, electroporation of intact cells, polyethyleneglycol-mediated protoplast transformation, electroporation of protoplasts, liposome-mediated transformation, silicon-whiskers mediated transformation etc. Said transgene may be stably integrated into the genome of said plant cell, resulting in a transformed plant cell. The transformed plant cells obtained in this way may then be regenerated into mature fertile transformed plants.

Further provided is a method of effecting seed- and funiculus-preferential expression of a nucleic acid comprising introducing the recombinant gene according to the invention into the genome of a plant, or providing the plant according to the invention. Also provided is a method for altering seed properties of a plant or to produce a commercially relevant product in a plant, comprising introducing the recombinant gene according to the invention into the genome of a plant, or providing the plant according to the invention. In another embodiment, said plant is a seed crop plant.

"Seed properties" as used herein are properties of the seed. Seed properties can, for example, be seed yield, seed storage compound production, seed compound accumulation, seed nutrient accumulation; seed micronutrient accumulation; seed storage compound quality, seed compound composition, seed quality, biotic stress tolerance such as disease tolerance, abiotic stress tolerance, herbicide tolerance, seed dormancy, seed imbibition, seed germination, seed vigor. Seed storage compounds can, for example, be, seed oil, seed starch, or seed protein.

Seed properties may be modulated by modulating metabolic pathways, such as starch metabolism, sugar metabolism, inositol phosphate metabolism, glycolysis, amino acid biosynthesis, carbon metabolism, nucleotide metabolism, oxidative pentose phosphate cycle, fatty acid biosynthesis, protein synthesis, or phytate metabolism, and modulating secondary metabolism pathways. Another example is the methyl recycling metabolic activity impacting chromatin remodeling, phospholipid biosynthesis and cell wall lignification. Such metabolic pathways can be modulated by, for example, overexpressing or down-regulating a gene involved in one or more of the metabolic pathways using the seed- and funiculus-preferential promoter according to the invention.

Yield as used herein can comprise yield of the plant or plant part which is harvested, such as seed, including seed oil content, seed protein content, seed weight, seed number. Increased yield can be increased yield per plant, and increased yield per surface unit of cultivated land, such as yield per hectare. Yield can be increased by modulating, for example, by increasing seed size or oil content or indirectly by increasing the tolerance to biotic and abiotic stress conditions and decreasing seed abortion.

Quality as used herein can comprise quality of the seed or grain such as beneficial carbohydrate composition or level, beneficial amino acid composition or level, beneficial fatty acid composition or level, nutritional value, seed and fiber content.

Abiotic stress tolerance as used herein can comprise resistance to environmental stress factors such as drought, extreme (high or low) temperatures.

Biotic stress tolerance as used herein can comprise pest resistance, such as resistance or fungal, bacterial, bacterial or viral pathogens or insects.

Also provided is the use of the isolated nucleic acid according to the invention to regulate expression of an operably linked nucleic acid in a plant, and the use of the isolated nucleic acid according to the invention, or the recombinant gene according to the invention to alter seed properties of a plant or to produce a commercially relevant product in a plant. In a further embodiment, said plant is a trait as used herein refers to beneficial properties of the plant, such as commercially beneficial properties of a plant.

Also provided is the use of the isolated nucleic acid according to the invention to identify other nucleic acids comprising seed- and funiculus-preferential promoter activity.

The promoters according to the invention can further be used to create hybrid promoters, i.e. promoters containing (parts of) one or more of the promoters(s) of the current invention and (parts of) other promoter which can be newly identified or known in the art. Such hybrid promoters may have optimized tissue specificity or expression level.

Yet another embodiment provides a method of producing food, feed, or an industrial product comprising (a) obtaining the plant or a part thereof, according to the invention; and (b) preparing the food, feed or industrial product from the plant or part thereof. In another embodiment, said food or feed is oil, meal, grain, starch, flour or protein, or said industrial product is biofuel, fiber, industrial chemicals, a pharmaceutical or a nutraceutical.

A "seed crop" or "seed crop plant" as used herein is a crop grown for its seeds or material derived from the seeds. Examples of seed crops are rice, maize, wheat, barley, millet, rye, oats, camelina, crambe, *Linum*, castor bean, calendula, safflower, sunflower, soybean, cotton, or *Brassica* species, such as *Brassica napus, Brassica juncea, Brassica carinata, Brassica rapa, Brassica oleracea*, and *Brassica nigra*.

"Brassicaceae" or "Brassicaceae plant" as used herein refers to plants belonging to the family of Brassicaceae plants, also called Cruciferae or mustard family. Examples of Brassicaceae are, but are not limited to, *Brassica* species, such as *Brassica napus, Brassica oleracea, Brassica rapa, Brassica carinata, Brassica nigra*, and *Brassica juncea; Raphanus* species, such as *Raphanus caudatus, Raphanus raphanistrum*, and *Raphanus sativus; Matthiola* species; *Cheiranthus* species; *Camelina* species, such as *Camelina sativa; Crambe* species, such as *Crambe abyssinica* and *Crambe hispanica; Eruca* species, such as *Eruca vesicaria; Sinapis* species such as *Sinapis alba; Diplotaxis* species; *Lepidium* species; *Nasturtium* species; *Orychophragmus* species; *Armoracia* species, *Eutrema* species; *Lepidium* species; and *Arabidopsis* species.

Said Brassicaceae plant can be a *Brassica* plant. "*Brassica* plant" refers to allotetraploid or amphidiploid *Brassica napus* (MCC, 2n=38), *Brassica juncea* (AABB, 2n=36), *Brassica carinata* (BBCC, 2n=34), or to diploid *Brassica rapa* (syn. *B. campestris*) (AA, 2n=20), *Brassica oleracea* (CC, 2n=18) or *Brassica nigra* (BB, 2n=16).

Crop plants of the *Brassica* species are, for example, *Brassica napus, Brassica juncea, Brassica carinata, Brassica rapa* (syn. *B. campestris*), *Brassica oleracea* or *Brassica nigra*.

The plants according to the invention may additionally contain an endogenous or a transgene, which confers herbicide resistance, such as the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EPO 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylaminocarbonyltriazolinones, triazolopyrimidines or pyrimidyl(oxy/thio)benzoates, such as oilseed rape imidazolinone-tolerant mutants PM1 and PM2, currently marketed as Clearfield® canola. Further, the plants according to the invention may additionally contain an endogenous or a transgene which confers increased oil content or improved oil composition, such as a 12:0 ACP thioesterase increase to obtain high laureate, which confers pollination control, such as such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants or seeds of the plants according to the invention may be further treated with a chemical compound, such as a chemical compound selected from the following lists: Herbicides: Clethodim, Clopyralid, Diclofop, Ethametsulfuron, Fluazifop, Glufosinate, Glyphosate, Metazachlor, Quinmerac, Quizalofop, Tepraloxydim, Trifluralin. Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus*, *Bacillus firmus* strain I-1582, *Bacillus subtilis*, *Bacillus subtilis* strain GB03, *Bacillus subtilis* strain QST 713, *Bacillus pumulis*, *Bacillus. pumulis* strain GB34. Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram,Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluoroethyl)sulfinyl]phenyl}-3-(trifluoromethyl)-1H-1,2,4-triazol-5-amine, (1E)-N-[(6-chloropyridin-3-yl)methyl]-N''-cyano-N-(2,2-difluoroethyl)ethanimidamide, *Bacillus firmus*, *Bacillus firmus* strain 1-1582, *Bacillus subtilis*, *Bacillus subtilis* strain GB03, *Bacillus subtilis* strain QST 713, Metarhizium anisopliae F52.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents, such as seed obtained by selfing or crossing, e.g. hybrid seed (obtained by crossing two inbred parental lines), hybrid plants and plant parts derived there from are encompassed herein, unless otherwise indicated.

In some embodiments, the plant cells of the invention as well as plant cells generated according to the methods of the invention, may be non-propagating cells.

The obtained plants according to the invention can be used in a conventional breeding scheme to produce more plants with the same characteristics or to introduce the same characteristic in other varieties of the same or related plant species, or in hybrid plants. The obtained plants can further be used for creating propagating material. Plants according to the invention can further be used to produce gametes, seeds (including crushed seeds and seed cakes), seed oil, embryos, either zygotic or somatic, progeny or hybrids of plants obtained by methods of the invention. Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

Furthermore, the disclosed invention is expected to yield similar results in other seed crop plant species. Particularly, it is expected to drive seed- and funiculus-preferential expression in soybean. It is also expected to drive seed- and funiculus-preferential expression in wheat. The disclosed promoter may lead to a seed- and funiculus-preferential expression in cotton.

The sequence listing contained in the file named "BCS16-2003_ST25.txt", which is 45 kilobytes (size as measured in Microsoft Windows®), contains 24 sequences SEQ ID NO: 1 through SEQ ID NO: 24 is filed herewith by electronic submission and is incorporated by reference herein.

In the description and examples, reference is made to the following sequences:
SEQUENCES
  SEQ ID NO: 1: nucleotide sequence of the T-DNA PsIp1 BnA::GUS.
  SEQ ID NO: 2: nucleotide sequence of the T-DNA PsIp1 intron BnA::GUS.
  SEQ ID NO: 3: nucleotide sequence of the promoter region PsIp1 intron BnA.
  SEQ ID NO: 4: nucleotide sequence of the promoter region PsIp1 intron BnC.
  SEQ ID NO: 5: nucleotide sequence of the promoter region PsIp1 intron Br.
  SEQ ID NO: 6: nucleotide sequence of the promoter region PsIp1 intron Bo.
  SEQ ID NO: 7: nucleotide sequence of the promoter region PsIp1 intron BjA.
  SEQ ID NO: 8: amino acid sequence of SLP1 BnA.
  SEQ ID NO: 9: amino acid sequence of SLP1 BnC.
  SEQ ID NO: 10: amino acid sequence of SLP1 Br.
  SEQ ID NO: 11: amino acid sequence of SLP1 Bo.
  SEQ ID NO: 12: amino acid sequence of SLP1 BjA.
  SEQ ID NO: 13: nucleotide sequence of the coding sequence of SLP1 BnA.
  SEQ ID NO: 14: nucleotide sequence of the coding sequence of SLP1 BnC.
  SEQ ID NO: 15: nucleotide sequence of the coding sequence of SLP1 Br.
  SEQ ID NO: 16: nucleotide sequence of the coding sequence of SLP1 Bo.
  SEQ ID NO: 17: nucleotide sequence of the coding sequence of SLP1 BjA.

SEQ ID NO: 18: Promoter consensus sequence.
SEQ ID NO: 19: UTR consensus sequence 1.
SEQ ID NO: 20: UTR consensus sequence 2.
SEQ ID NO: 21: UTR consensus sequence 3.
SEQ ID NO: 22: Intron consensus sequence 1.
SEQ ID NO: 23: Intron consensus sequence 2.
SEQ ID NO: 24: Intron consensus sequence 3.

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1—Generation of Expression Constructs with the PsIp1BnA Promoter Fragments of *Brassica napus* Operably Linked to the GUS Reporter Gene (PsIp1 BnA:GUS and PsIp1 Intron BnA::GUS)

Because the SLP1 gene structure contains an intron immediately after the translation start (FIG. 1), it was hypothesized that this intron may be required for the promoter activity. Therefore expression constructs with or without this first intron were generated.

The promoter sequence of the *Brassica napus* PsIp1 BnA promoter (position 1 to 1414 of SEQ ID NO: 3 or 5' to 3' position 139 to 1552 of SEQ ID NO:1) isolated from an in house developed *Brassica napus* line, the GUS gene (β-glucuronidase) with intron (5' to 3' position 1553 to 3553 of SEQ ID NO: 1) and a fragment of the 3' untranslated region (UTR) of the TL-DNA gene 7 of *Agrobacterium tumefaciens* octopine (5' to 3' position 3610 to 3813 of SEQ ID NO: 1) were assembled in a vector which contains the bar selectable marker cassette (position 3894 to 6404 of SEQ ID NO: 1) to result in the T-DNA PsIp1 BnA::GUS (SEQ ID NO: 1).

The promoter sequence of the *Brassica napus* sIp1BnA promoter plus the first intron (SEQ ID NO: 3 or 5' to 3' position 139 to 2193 of SEQ ID NO: 2) isolated from an in house developed *Brassica napus* line, the GUS gene (β-glucuronidase) with intron (5' to 3' position 2194 to 4191 of SEQ ID NO: 2) and a fragment of the 3' untranslated region (UTR) of the TL-DNA gene 7 of *Agrobacterium tumefaciens* octopine (5' to 3' position 4248 to 4451 of SEQ ID NO: 2) were assembled in a vector which contains the bar selectable marker cassette (position 4532 to 7042 of SEQ ID NO: 2) to result in the T-DNA PsIp1 intron BnA::GUS (SEQ ID NO: 2).

Example 2—Generation of Transgenic Plants Comprising the PsIp1 BnA::GUS or PsIp1 Intron BnA::GUS In a next step the recombinant vectors comprising the expression cassettes of example 1, i. e. PsIp1 BnA::GUS and PsIp1 intron BnA::GUS, were used to stably transform *Brassica napus*.

Example 3—In Planta Expression Pattern of PsIp1BnA::GUS and PsIp1BnAintron::GUS in *Brassica napus*

The in planta expression pattern of PsIp1 BnA::GUS and PsIp1 intron BnA::GUS in the different tissues of *Brassica napus* seeds was monitored according to the method of Jasik et al. 2011.

Figure 2:
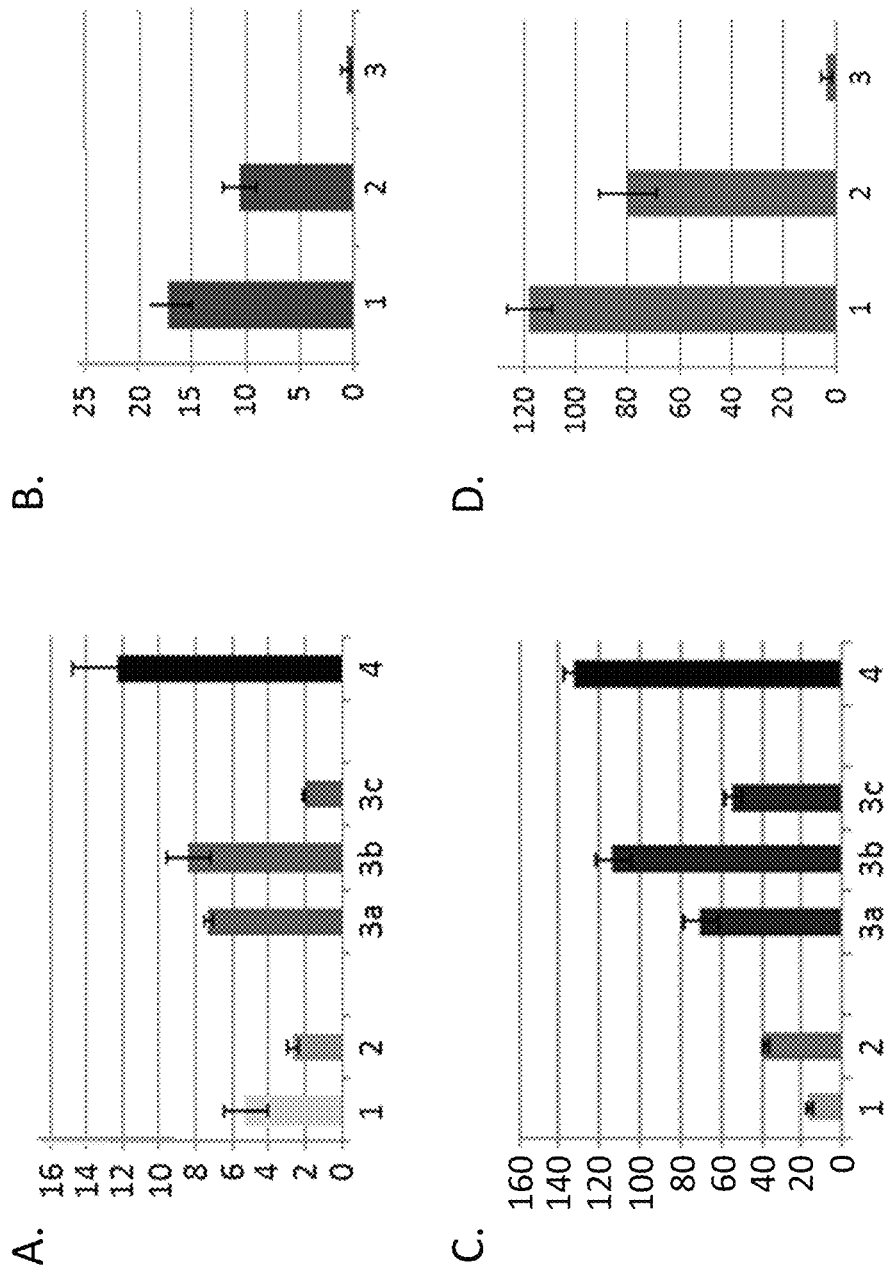
FIG. 2: Semi quantitative assessment of GUS labelling ($\mu U^*mg^{-1}$ fresh weight*h) in transgenic lines carrying a PsIp1BnA::GUS T-DNA (A and B) or a PsIp1BnAintron::GUS T-DNA (C and D). Embryos (A and C) and seed coats (B and D) were stained at the following stages: 1: 15 to 18 DAF, 2: 20 to 23 DAF, 3: 27 to 32 DAF, 4: 35 to 40 DAF. For the stages 1, 2 and 4 embryos, the stainings are assessed for the whole embryos while for the stage 3 embryos, the staining was quantified in the outer cotyledon (a), in the inner cotyledon (b) and in the hypocotyl (c) separately.

FIG. 2 provides the semi quantitative assessment of the GUS labelling in the seed coat and the embryo of transgenic lines carrying either the PsIp1 BnA::GUS or PsIp1 intron BnA::GUS T-DNAs. For both constructs, the GUS staining is detected in both embryos and seed coat. For both constructs, the intensity of the staining in the embryo increases as the embryo progresses through the developmental stages, in other words, the expression level is higher at late stage than at early stage. In contrast, in the seed coat, the labelling is the strongest at early stages and then decreases as it progresses towards maturation. Though both constructs confer the same expression pattern, lines carrying the T-DNA PsIp1 intron BnA::GUS have a moderate expression level while the lines carrying the T-DNA PsIp1BnA::GUS have a weak expression level. The presence of the intron after the translation start ATG increases the expression level by at least 3 fold, up to more than 10 fold.

Figure 3:
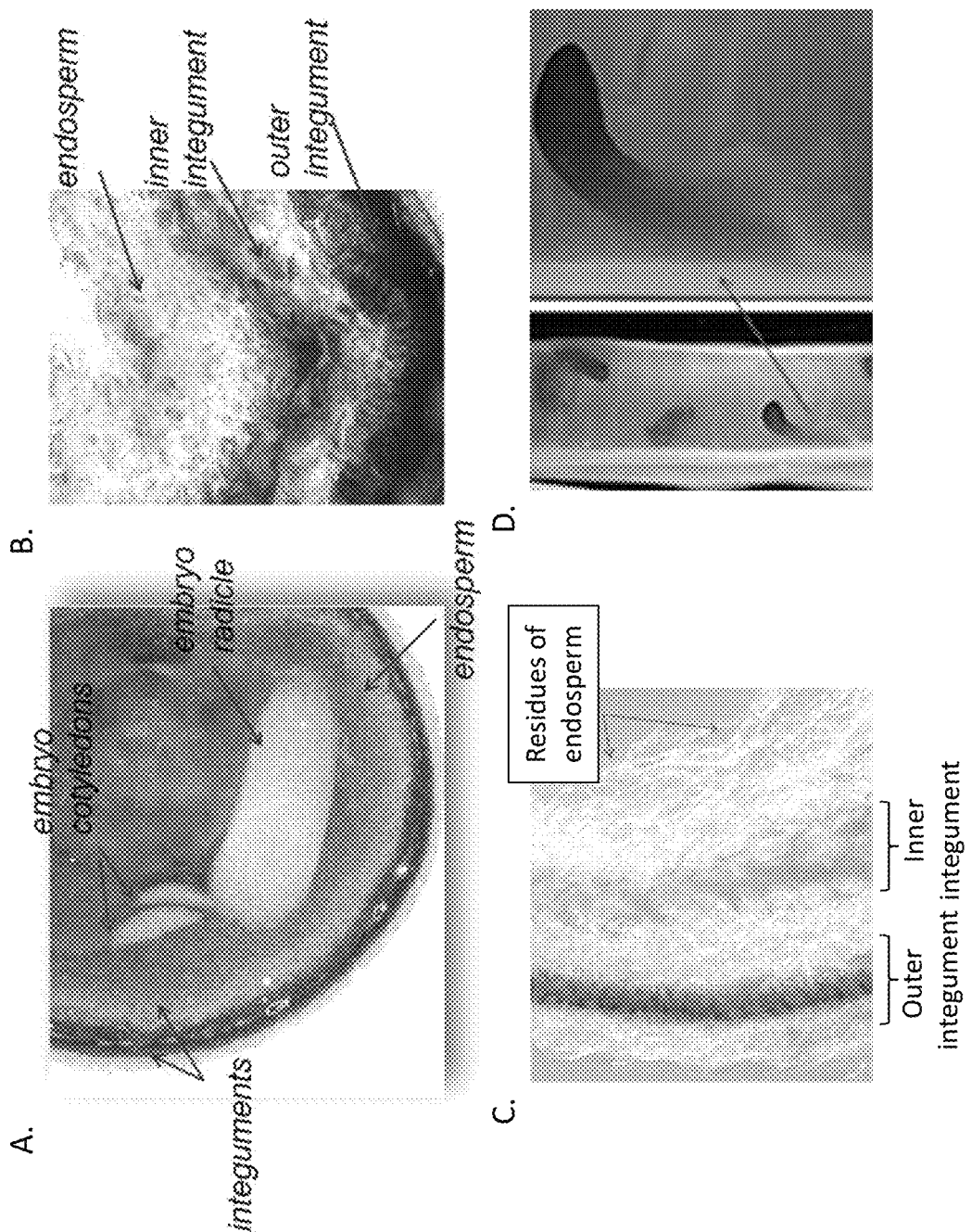
FIG. 3: Expression profile analysis in seeds carrying the T-DNA PsIp1 intron BnA::GUS. GUS labelling in the seed coat and endosperm at early stage (A, B) and at late stage (C), as well as in the funiculus (D). The right panel of D represent a close-up view of one of the funiculi shown in the left panel of D.

FIG. 3 shows the GUS labelling of the reporter gene in the endosperm and seed coat at early (panels A and B) and late (panel C) seed developmental stages. At early stage, both endosperm and seed coat are labelled, with about the same intensity. The close-up view shows that the outer integument of the seed coat is more intensely stained than the inner integument. The activity of the PsIp1 intron BnA promoter fragment is moderate in the endosperm and seed coat at early stage. The close up view on the seed coat and endosperm at late stage show that the GUS labelling occurs in the outer integument but not in the inner integument, nor in the endosperm residues. FIG. 3 further shows the GUS labelling of the reporter gene in the funiculus. The same result was obtained with the lines carrying the PsIp1 BnA::GUS T-DNA though with a weaker intensity.

Some GUS activity was also detected in the assessed non-seed tissues, namely stem, young pod, flowers (receptacle and peduncle) and leaves, though to a lower level, at least 2 fold weaker than in the seed and the funiculus tissues, thereby confirming the seed- and funiculus-preference of the promoter PsIp1 intron BnA.

Example 4—Identification of the Second *Brassica napus* Copy of SLP1 and of the Orthologues of SLP1 in *Brassica rapa, Brassica oleracea* and *Brassica juncea*

The sequences of the second *Brassica napus* copy of SLP1 as well as the orthologues in *Brassica rapa, Brassica oleracea* and *Brassica juncea* were obtained by blasting the coding sequence of the SLP1 BnA against an in-house database of *Brassica napus, Brassica rapa, Brassica oleracea* and *Brassica juncea* sequences.

The nucleotide sequences obtained in this way are given in SEQ ID NO: 13 to SEQ ID NO: 17. These nucleotide sequences were translated into amino acid sequences, given respectively in SEQ ID NO: 8 to SEQ ID NO: 12.

In *Brassica rapa*, the result indicated that 2 copies of SLP1 are present in the genome, on two different chromosomes. As the nucleotide sequences of the two genomic fragments comprising the promoter and the genes are 100% identical, the nucleotide and amino acid sequences are provided only once. In *Brassica juncea*, no start codon was identified for the B copy of SLP1. This copy was therefore considered a pseudogene and was not further studied.

FIG. 6 shows the alignment of the retrieved amino acid sequence. Any two of these sequences share at least 97% sequence identity.

Examples 5

RNA Isolation from Different *Brassica* Tissues

The following tissues were isolated from *Brassica napus*:
a. Apical meristem 33 days after sowing (DAS) (including smallest leaves) (AM33)
b. Big flower buds (>5 mm) 42 DAS (BFB42)
c. Cotyledons (with hypocotyl) 10 DAS (CTYL10)
d. Open flowers 52 DAS (OF52)
e. Pods 14-20 DAS (Pod2)
f. Pods 21-25 DAS (Pod3)
g. Roots 14 DAS (Ro2w)
h. Small flower buds ≤5 mm 42 DAS (SFB42)
i. Seeds 14-20 days after flowering (DAF) (Seed2)
j. Seeds 21-25 DAF (Seed3)
k. Seeds 26-30 DAF (Seed4)
l. Seeds 31-35 DAF (Seed5)
m. Seeds 42 DAF (Seed6)
n. Seeds 49 DAF (Seed7)
o. Stem 14 DAS (St2w)
p. Stem 33 DAS (St5w)
q. Young leaf 33 DAS (≤3 cm leaf next to apical meristem) (YL33)

The following tissues were isolated from *Brassica juncea*:
a. Apical meristem 22 days after sowing (DAS) (including smallest leaves) (AM22)
b. Big flower buds (>5 mm) 35 DAS (BFB35)
c. Cotyledons (with hypocotyl) 8 DAS (CTYL8)
d. Open flowers 35 DAS (OF35)
e. Pods 14-20 DAS (Pod2)
f. Pods 21-25 DAS (Pod3)
g. Pods 26-30 DAS (Pod4)
h. Pods 31-35 DAS (Pod5)
i. Roots 14 DAS (Ro2w)
j. Small flower buds ≤5 mm 35 DAS (SFB35)
k. Seeds 14-20 days after flowering (DAF) (Seed2)
l. Seeds 21-25 DAF (Seed3)
m. Seeds 26-30 DAF (Seed4)
n. Seeds 31-35 DAF (Seed5)
o. Seeds 42 DAF (Seed6)
p. Seeds 49 DAF (Seed7)
q. Stem 14 DAS (St2w)
r. Stem 22 DAS (St3w)
s. Young leaf 22 DAS (≤3 cm leaf next to apical meristem) (YL22)
t. Old leaf 22 DAS (OL22)

Total RNA from the different tissues was isolated according to standard methods.

In our growth conditions, the correspondence between embryo developmental stages and the selected time points is as follows:
a. Between 10 and 13 DAF: torpedo stage
b. Seed2 or between 14 and 20 DAF: "walking stick" cotyledon stage
c. Seed3 or between 21 and 25 DAF: curled cotyledon stage
d. Seed4 and Seed5 or between 26 and 35 DAF: green cotyledon stage
e. Seed6 and Seed7 or after 36 DAF: mature embryo Example 6—In Silico Expression Analyses of the Different Copies of SLP1 of *Brassica napus* and their Orthologues in *Brassica rapa, Brassica oleracea* and *Brassica juncea*

Figure 5:
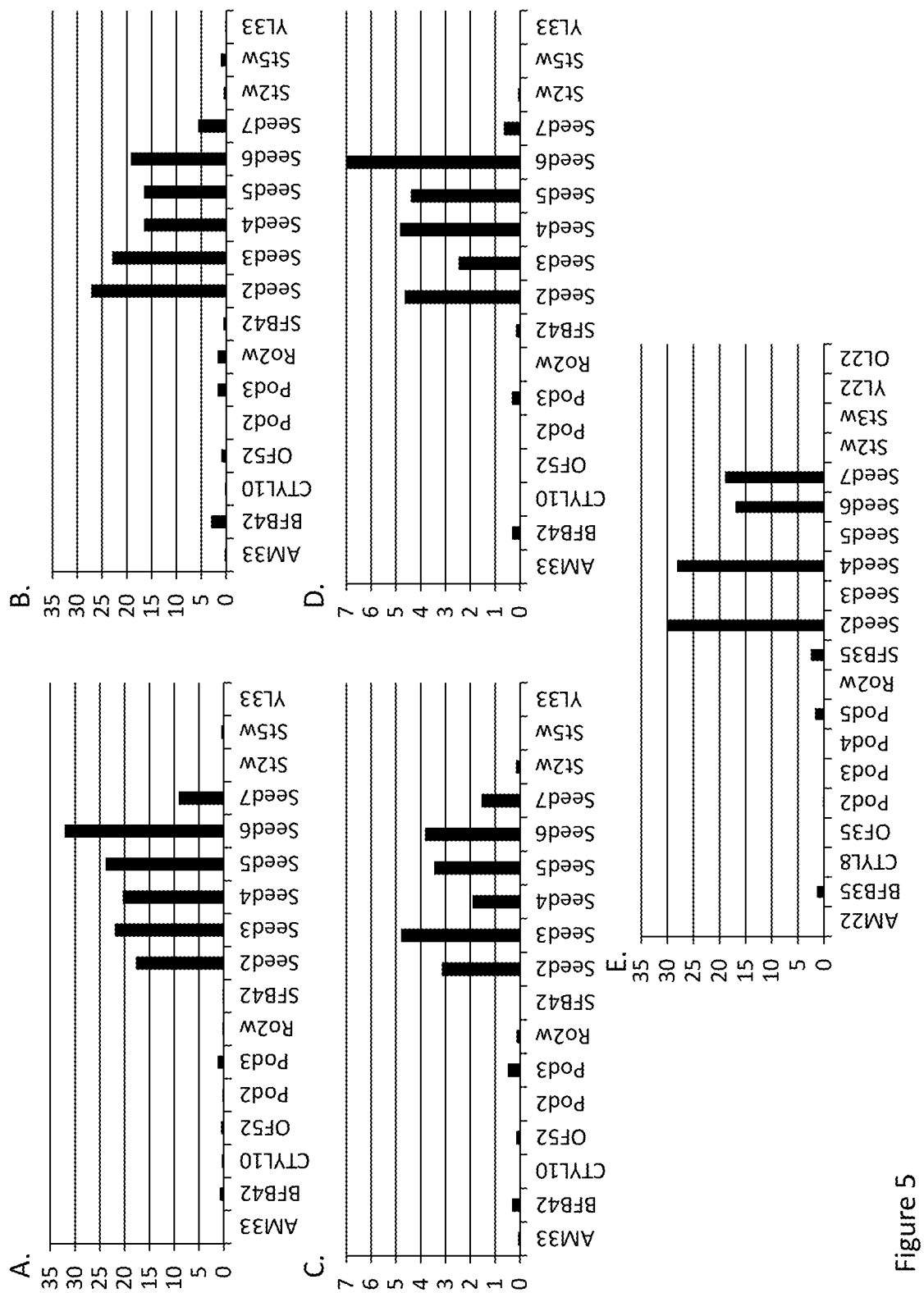
FIG. 5: Relative expression levels of different Brassica SLP1 transcripts in different plant tissues. A: SLP1 BnA; B: SLP1BnC; C: SPL1 Br; D: SLP1 Bo; E: SLP1 BjA. Different tissues for A to D: AM33: Apical meristem 33 days after sowing (DAS); BFB42: Big flower buds 42 DAS; CTYL10: Cotyledons 10 DAS; OF52: Open flowers 52 DAS; Pod2: Pods 14-20 DAS; Pod3: Pods 21-25 DAS; Ro2w: Roots 14 DAS; SFB42: Small flower buds 42 DAS; Seed2: Seeds 14-20 days after flowering (DAF); Seed3: Seeds 21-25 DAF; Seed4: Seeds 26-30 DAF; Seed5: Seeds 31-35 DAF; Seed6: Seeds 42 DAF; Seed7: Seeds 49 DAF; St2w: Stem 14 DAS; St5w: Stem 33 DAS; YL33: Young leaf 33 DAS. Different tissues for E: AM22: Apical meristem 22 days after sowing (DAS); BFB35: Big flower buds 35 DAS; CTYL8: Cotyledons 8 DAS; OF35: Open flowers 35 DAS; Pod2: Pods 14-20 DAS; Pod3: Pods 21-25 DAS; Pod4: Pods 26-30 DAS; Pod5: Pods 31-35 DAS; Ro2w: Roots 14 DAS; SFB35: Small flower buds 35 DAS; Seed2: Seeds 14-20 days after flowering (DAF); Seed3: Seeds 21-25 DAF; Seed4: Seeds 26-30 DAF; Seed5: Seeds 31-35 DAF; Seed6: Seeds 42 DAF; Seed7: Seeds 49 DAF; St2w: Stem 14 DAS; St3w: Stem 22 DAS; YL22: Young leaf 22 DAS; OL22: Old leaf 22 DAS.

FIG. 5 shows the relative expression levels of the endogenous transcripts of the different *Brassica napus* (A and B), *Brassica oleracea* (C), *Brassica rapa* (D) and *Brassica juncea* (E) copies of SLP1 in different tissues, as isolated in Example 5.

The SLP1 BnA transcript (panel A) is clearly detected in the seed tissues (Seed2 to Seed7) and only barely detectable in other tissues. This result confirms, as determined in planta, that PsIp1 intron BnA has seed-preferential promoter activity.

The SLP1 BnC transcript (panel B) is clearly detected in the seed tissues (Seed2 to Seed7) and only barely detectable in the other tissues. This result confirms, as determined in planta, that PsIp1 intron BnC has seed-preferential promoter activity.

The SLP1 Br transcript (panel C) is clearly detected in the seed tissues (Seed2 to Seed7) and only barely detectable in the other tissues. This result confirms, as determined in planta, that PsIp1 intron Br has seed-preferential promoter activity.

The SLP1 Bo transcript (panel D) is clearly detected in the seed tissues (Seed2 to Seed7) and only barely detectable in the other tissues. This result confirms, as determined in planta, that PsIp1 intron Bo has seed-preferential promoter activity.

The SLP1 BjA transcript (panel E) is clearly detected in the seed tissues (Seed2, Seed4, Seed6 and Seed7) and only barely detectable in the other tissues. This result confirms, as determined in planta, that PsIp1 intron BjA has seed-preferential promoter activity.

Example 7—Sequence Analysis of the Promoters and First Intron of the SLP1 Genes from *Brassica rapa, Brassica juncea, Brassica oleracea* and *Brassica napus*

For the different SLP1 gene identified, the genomic DNA sequence upstream of the translation start and including the first intron was retrieved from an in-house database of *Brassica napus, Brassica rapa, Brassica oleracea* and *Brassica juncea* sequences. The nucleotide sequences obtained in this way are given in SEQ ID NO: 4 to SEQ ID NO: 7.

FIG. 6 shows the alignment of the about 400 bp sequence upstream of the translation start of the promoter sequences (SEQ ID NO: 3 to SEQ ID NO: 7). These promoters share a surprisingly high level of conservation in this region. Four consensus sequences were identified. The promoters described herein each comprise the following consensus sequence:

a. Promoter consensus sequence is given in SEQ ID NO: 18;
b. UTR consensus sequence 1 is given in SEQ ID NO: 19;
c. UTR consensus sequence 2 is given in SEQ ID NO: 20;
d. UTR consensus sequence 3 is given in SEQ ID NO: 21.

The presence of these consensus sequences in all analyzed promoter sequences described herein indicate that these consensus sequences are required for the observed seed- and funiculus-preferential expression pattern.

Consequently, as PsIp1 BnC (position 1 to 1364 of SEQ ID NO: 4) sequence comprises the promoter consensus sequence and the 3 UTR consensus sequences, it can be concluded that it has seed- and funiculus-preferential promoter activity. As PsIp1 intron BnC (SEQ ID NO: 4) sequence comprises the promoter consensus sequence and the 3 UTR consensus sequences, it can also be concluded that it has seed- and funiculus-preferential promoter activity. As PsIp1 Br (position 1 to 1365 of SEQ ID NO: 5) sequence comprises the promoter consensus sequence and the 3 UTR consensus sequences, it can also be concluded that it has seed- and funiculus-preferential promoter activity. As PsIp1 intron Br (SEQ ID NO: 5) sequence comprises the promoter consensus sequence and the 3 UTR consensus sequences, it can also be concluded that it has seed- and funiculus-preferential promoter activity. As PsIp1 Bo (position 1 to 1358 of SEQ ID NO: 6) sequence comprises the promoter consensus sequence and the 3 UTR consensus sequences, it can be concluded that it has seed- and funiculus-preferential promoter activity. As PsIp1 intron Bo (SEQ ID NO: 6) sequence comprises the promoter consensus sequence and the 3 UTR consensus sequences, it can be concluded that it has seed- and funiculus-preferential promoter activity. As PsIp1 BjA (position 1 to 1363 of SEQ ID NO: 7) sequence comprises the promoter consensus sequence and the 3 UTR consensus sequences, it can be concluded that it has seed- and funiculus-preferential promoter activity. As PsIp1 intron BjA (SEQ ID NO: 7) sequence comprises the promoter consensus sequence and the 3 UTR consensus sequences, it can be concluded that it has seed- and funiculus-preferential promoter activity.

More generally, these results indicate that a *Brassica* promoter comprising the promoter consensus sequence and the 3 UTR consensus sequences would have seed- and funiculus-preferential promoter activity.

FIG. 7 shows the alignment of the first about 300 bp of the intron sequence of the promoter sequences (SEQ ID NO: 3 to SEQ ID NO: 7). This intron shares a surprisingly high level of conservation in this region. Three consensus sequences were identified in this first intron. The promoters described herein each comprise the following consensus sequence:
a. Intron consensus sequence 1 is given in SEQ ID NO: 22;
b. Intron consensus sequence 2 is given in SEQ ID NO: 23;
c. Intron consensus sequence 3 is given in SEQ ID NO: 24.

The presence of these consensus sequences in all analyzed intron sequences described herein indicates that these consensus sequences may be required for the observed increased expression level compared to the expression level achieved without the first intron.

Consequently, as the intron in PsIp1 intron BnC (position 1368 to 1650 of SEQ ID NO: 4) comprises the intron consensus sequences 1 to 3, it can be concluded that PsIp1 intron BnC has higher (at least 3 fold, up to 10 fold) seed- and funiculus-preferential promoter activity than PsIp1 BnC (position 1 to 1364 of SEQ ID NO: 4). As the intron in PsIp1 intron Br (position 1369 to 2001 of SEQ ID NO: 5) comprises the intron consensus sequences 1 to 3, it can be concluded that PsIp1 intron Br (SEQ ID NO: 5) has higher (at least 3 fold, up to 10 fold) seed- and funiculus-preferential promoter activity than PsIp1 Br (position 1 to 1365 of SEQ ID NO: 5). As the intron in PsIp1 intron Bo (position 1362 to 1647 of SEQ ID NO: 6) comprises the intron consensus sequences 1 to 3, it can be concluded that PsIp1 intron Bo (SEQ ID NO: 6) has higher (at least 3 fold, up to 10 fold) seed- and funiculus-preferential promoter activity than PsIp1 Bo (position 1 to 1358 of SEQ ID NO: 6). As the intron in PsIp1 intron BjA (position 1367 to 2001 of SEQ ID NO: 7) comprises the intron consensus sequences 1 to 3, it can be concluded that PsIp1 intron BjA (SEQ ID NO: 7) has higher (at least 3 fold, up to 10 fold) seed- and funiculus-preferential promoter activity than PsIp1 BjA (position 1 to 1363 of SEQ ID NO: 7).

More generally, these results indicate that a *Brassica* promoter comprising a intron comprising the intron consensus sequences 1 to 3 would have higher (at least 3 fold, up to 10 fold) promoter activity than the same *Brassica* promoter without such intron.

The invention claimed is:

1. A recombinant gene comprising a nucleic acid having seed- and funiculus-preferential promoter activity comprising:
   (a) a nucleic acid comprising: the nucleotide sequence from the nucleotide sequence position 1 to the nucleotide sequence position 1414 of SEQ ID NO: 3, or a functional fragment thereof of SEQ ID NO: 3 from the nucleotide sequence position 1 to the nucleotide sequence position 1414 of SEQ ID NO: 3, wherein said functional fragment comprises at least 400 contiguous nucleotides of the nucleotide sequence of SEQ ID NO: 3 from the nucleotide sequence position 1 to the nucleotide sequence position 1414 of SEQ ID NO: 3, wherein said functional fragment comprises SEQ ID NO: 18, and wherein said functional fragment has said seed- and funiculus-preferential promoter activity of the SEQ ID NO: 3 from the nucleotide sequence position 1 to the nucleotide sequence position 1414 of SEQ ID NO: 3, or
   (b) a nucleic acid comprising a nucleotide sequence having at least 99% nucleotide sequence identity to the SEQ ID NO: 3 from the nucleotide sequence position 1 to the nucleotide sequence position 1414 of SEQ ID NO: 3,
and wherein said nucleic acid of part (a) and said nucleic acid of part (b) are operably linked to a heterologous nucleic acid sequence encoding an expression product of interest, and a transcription termination and polyadenylation sequence.

2. The recombinant gene according to claim 1, wherein the expression product of interest is an RNA molecule capable of modulating the expression of a gene or is a protein.

3. A host cell comprising the recombinant gene according to claim 1.

4. The host cell of claim 3, wherein said host cell is an *E. coli* cell, an *Agrobacterium* cell, an algal cell, a yeast cell, or a plant cell.

5. A plant comprising the recombinant gene of claim 1.

6. A plant comprising at least two recombinant genes according to claim 1, and wherein the heterologous nucleic acid sequence is different in said recombinant genes.

7. A seeds obtained from the plant according to claim 5, wherein the seed has said recombinant gene.

8. A method of producing a transgenic plant comprising:
   (a) introducing or providing the recombinant gene according to claim 1 to a plant cell to create transgenic plant cells; and
   (b) regenerating a transgenic plants from said transgenic plant cells.

9. A method of effecting seed- and funiculus-preferential expression of a nucleic acid in a plant, comprising introducing and integrating stably the recombinant gene according to claim 1 into the genome of said plant.

10. A method of producing food, feed, or an industrial product comprising preparing food, feed or industrial product from the plant of claim 5 or a plant part thereof, and wherein said plant part and said food, said feed or said industrial product comprises said recombinant gene.

11. The method of claim 10, wherein said food or said feed comprises oil, meal, grain, starch, flour or protein; or wherein said industrial product comprises biofuel, fiber, industrial chemicals, a pharmaceutical or a nutraceutical.

12. The recombinant gene according to claim 1, wherein said nucleic acid of part (a) and said nucleic acid of part (b) having said seed- and funiculus-preferential promoter activity further comprise an intron comprising the nucleotide sequence from the nucleotide sequence position 1418 to the nucleotide sequence position 2055 of SEQ ID NO: 3.

13. The recombinant gene according to claim 12, wherein said nucleic acid of part (a) and said nucleic acids of part (b) having said seed- and funiculus-preferential promoter activity comprising said intron has higher seed- and funiculus-preferential promoter activity than said nucleic acid of part (a) and said nucleic acid of part (b) not comprising said intron.

* * * * *